United States Patent [19]

Androphy et al.

[11] Patent Number: 5,770,384
[45] Date of Patent: Jun. 23, 1998

[54] METHOD FOR DETERMINING COMPOUND INTERACTION WITH E2 BINDING PROTEINS

[75] Inventors: Elliot J. Androphy, Natick; David E. Breiding, Somerville, both of Mass.

[73] Assignee: New England Medical Center Hospitals, Inc, Boston, Mass.

[21] Appl. No.: 612,986

[22] Filed: Mar. 6, 1996

Related U.S. Application Data

[62] Division of Ser. No. 361,806, Dec. 22, 1994.

[51] Int. Cl.$^6$ .............................. C12Q 1/00; C12P 21/06; C07K 14/025

[52] U.S. Cl. ........................... 435/7.8; 435/7.93; 435/7.1; 435/5; 435/69.1; 435/69.7; 514/2; 536/23.72; 530/300; 530/350

[58] Field of Search ................................. 435/7.8, 7.1, 5, 435/7.21, 7.93, 69.1, 69.7; 530/350, 300; 514/2; 536/23.72

[56] References Cited

U.S. PATENT DOCUMENTS 5,219,990  6/1993  Androphy et al. ....................... 530/350
5,464,936  11/1995  Botchan et al. .......................... 530/350

OTHER PUBLICATIONS

Ushikai et al., "Trans activation by the full–length E2 proteins of human papillomavirus type 16 and bovine papillomavirus type 1 in vitro and in vivo: cooperation with activation domains of cellular transcription factors", *J. Virology* 68(10):6655–6666 (1994).

DelVecchio, A.M. et al. (1992) "Transient Replication of Human Papillomavirus DNAs" *J. Virol.* 66(10):5949–5958.

Thierry F. and Yaniv M. (1987) "The BPV1–E2 trans–acting protein can be either an activator or a repressor of the HPV–18 regulatory region" *The EMBO J* 6: 3391–3397.

Yang Y–C et al. (1985) "Dissociation of transforming and trans–activation functions for bovine papillomavirus type 1" *Nature* 318: 575–577.

McBride A.A. et al. (1991) "The papillomavirus E2 regulatory proteins" *J. Biol. Chem.* 266(26):18411–18414.

Hwang E–S et al. (1993) "Inhibition of cervical carcinoma cell line proliferation by the introduction of a bovine papillomavirus regulatory gene"*J. Virol.* 67(7): 3720–3729.

Giri I. and Yaniv M. (1988) "Structural and mutational analysis of E2 trans–activating proteins of papillomaviruses reveals three distinct functional domains" *The EMBO J.* 7(9): 2823–2829.

McBride A.A. et al. (1989) "E2 polypeptides encoded by bovine papillomavirus type 1 form dimers through the common carboxyl–terminal domain: Transactivation is mediated by the conserved amino–terminal domain" *PNAS USA* 86: 510–514.

Winokur P. and McBride A.A. (1992) "Separation of the transcriptional activation and replication functions of the bovine papillomavirus–1 E2 protein" *The EMBO J.* 11(11):4111–4118.

Adams et al., "3,400 new expressed sequence tags identify diversity of transcripts in human brain", Nature Genetics 4;256–267 (1993).

Androphy et al., "Isolation of human cDNAs that interact with the papillomavirus E2 transcription protein", J Investigative Dermatology 100(4): 526 (1993).

Breiding et al., "Isolation of a novel human gene that interacts with the papillomavirus E2 transcription/replication protein", J. Investigative Dermatology 102(4):452 (1994).

*Primary Examiner*—Karen C. Carlson
*Attorney, Agent, or Firm*—Louis Myers; Lahive & Cockfield, LLP

[57] ABSTRACT

E2-BP polypeptides, nucleic acids encoding E2-BP polypeptides, and uses thereof.

42 Claims, 5 Drawing Sheets

| IN VITRO BINDING ASSAY | IN VITRO BINDING TO 42A | TWO HYBRID INTERACTION | TWO HYBRID ASSAY IN YEAST |
|---|---|---|---|
| GST \| E2-286 (1–266) | YES | YES | E2 WILD TYPE (1–410) |
| GST \| E2-286 (87L, 131H) (1–286) | YES | YES | E2 87L, 131H (1–410) |
| GST \| E2 53-286 | YES | YES | E2 53-410 |
| GST \| E2 113-286 | YES | YES | E2 113-410 |
| GST \| E2 134-286 | YES | YES | E2 139-410 |
| GST \| E2 162-286 | NO | NO | E2 162-410 |
| GST \| E2 113-215 | YES | YES | E2 HINGE DELETION (1–218, 284–410) |
| GST | NO | | |
| GST \| VP16 (410–490) | NO | | |

FIG. 2

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1071 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1071

( x i ) SEQUENCE DESCRIPTION: SEQ ID NO:1:

```
AAG  AAT  TCC  CAT  TGT  GCT  CTA  AAG  GGC  AGT  CAG  AGA  CAG  CCG  GGC  GCC         48
Lys  Asn  Ser  His  Cys  Ala  Leu  Lys  Gly  Ser  Gln  Arg  Gln  Pro  Gly  Ala
 1                    5                        10                       15

CAC  GGC  CCG  AGC  GCC  CAC  GGC  AGC  ACC  ATG  CCC  GCA  CTC  CTG  GAG  CGC         96
His  Gly  Pro  Ser  Ala  His  Gly  Ser  Thr  Met  Pro  Ala  Leu  Leu  Glu  Arg
                     20                        25                       30

CCC  AAG  CTT  TCC  AAC  GCC  ATG  GCC  AGG  GGC  CTG  CAC  CGG  CAC  ATT  ATG        144
Pro  Lys  Leu  Ser  Asn  Ala  Met  Ala  Arg  Gly  Leu  His  Arg  His  Ile  Met
               35                        40                       45

ATG  GAG  CGG  GAG  CAA  GCG  CAG  GAG  GAA  GAA  GAG  GTG  GAT  AAG  ATG  ATG        192
Met  Glu  Arg  Glu  Gln  Ala  Gln  Glu  Glu  Glu  Glu  Val  Asp  Lys  Met  Met
          50                        55                       60

GAA  CAG  AAG  ATG  AAG  GAA  GAA  CAG  GAG  AGA  AGG  AAG  AAA  AAG  GAG  ATG        240
Glu  Gln  Lys  Met  Lys  Glu  Glu  Gln  Glu  Arg  Arg  Lys  Lys  Lys  Glu  Met
 65                       70                        75                       80

GAA  GAG  AGA  ATG  TCA  TTA  GAG  GAG  ACC  AAG  GAA  CAA  ATT  CTG  AAG  TTG        288
Glu  Glu  Arg  Met  Ser  Leu  Glu  Glu  Thr  Lys  Glu  Gln  Ile  Leu  Lys  Leu
                    85                        90                       95

GAG  GAG  AAG  CTT  TTG  GCT  CTA  CAG  GAA  GAG  AAG  CAC  CAG  CTT  TTC  CTG        336
Glu  Glu  Lys  Leu  Leu  Ala  Leu  Gln  Glu  Glu  Lys  His  Gln  Leu  Phe  Leu
              100                       105                      110

CAG  CTC  AAG  AAA  GTT  TTA  CAT  GAG  GAA  GAA  AAA  CGG  AGG  CGA  AAG  GAA        384
Gln  Leu  Lys  Lys  Val  Leu  His  Glu  Glu  Glu  Lys  Arg  Arg  Arg  Lys  Glu
```

|     |     |     | 115 |     |     |     |     | 120 |     |     |     |     | 125 |     |     |      |
| --- | --- | --- | --- | --- | --- | --- | --- | --- | --- | --- | --- | --- | --- | --- | --- | ---- |
| CAG | AGT | GAC | CTG | ACC | ACC | CTG | ACA | TCA | GCT | GCA | TAC | CAG | CAG | AGC | CTG | 432  |
| Gln | Ser | Asp | Leu | Thr | Thr | Leu | Thr | Ser | Ala | Ala | Tyr | Gln | Gln | Ser | Leu |      |
|     | 130 |     |     |     |     | 135 |     |     |     |     | 140 |     |     |     |     |      |
| ACT | GTT | CAC | ACA | GGA | ACT | CAT | CTC | CTC | AGC | ATG | CAG | GGG | AGC | CCT | GGA | 480  |
| Thr | Val | His | Thr | Gly | Thr | His | Leu | Leu | Ser | Met | Gln | Gly | Ser | Pro | Gly |      |
| 145 |     |     |     |     | 150 |     |     |     |     | 155 |     |     |     |     | 160 |      |
| GGA | CAC | AAT | CGC | CCA | GGC | ACC | CTC | ATG | GCA | GCT | GAC | AGA | GCC | AAA | CAA | 528  |
| Gly | His | Asn | Arg | Pro | Gly | Thr | Leu | Met | Ala | Ala | Asp | Arg | Ala | Lys | Gln |      |
|     |     |     |     | 165 |     |     |     |     | 170 |     |     |     |     | 175 |     |      |
| ATG | TTT | GGA | CCC | CAA | GTG | CTT | ACG | ACC | CGG | CAC | TAC | GTG | GGC | TCA | GCA | 576  |
| Met | Phe | Gly | Pro | Gln | Val | Leu | Thr | Thr | Arg | His | Tyr | Val | Gly | Ser | Ala |      |
|     |     |     | 180 |     |     |     |     | 185 |     |     |     |     | 190 |     |     |      |
| GCT | GCT | TTT | GCA | GGG | ACA | CCA | GAG | CAT | GGA | CAA | TTC | CAA | GGC | AGT | CCT | 624  |
| Ala | Ala | Phe | Ala | Gly | Thr | Pro | Glu | His | Gly | Gln | Phe | Gln | Gly | Ser | Pro |      |
|     |     | 195 |     |     |     |     | 200 |     |     |     |     | 205 |     |     |     |      |
| GGT | GGT | GCC | TAT | GGG | ACT | GCT | CAG | CCC | CCA | CCT | CAC | TAT | GGG | CCC | ACA | 672  |
| Gly | Gly | Ala | Tyr | Gly | Thr | Ala | Gln | Pro | Pro | Pro | His | Tyr | Gly | Pro | Thr |      |
|     | 210 |     |     |     |     | 215 |     |     |     |     | 220 |     |     |     |     |      |
| CAG | CCA | GCT | TAT | AGT | CCT | AGT | CAG | CAG | CTC | AGA | GCT | CCT | TCG | GCA | TTC | 720  |
| Gln | Pro | Ala | Tyr | Ser | Pro | Ser | Gln | Gln | Leu | Arg | Ala | Pro | Ser | Ala | Phe |      |
| 225 |     |     |     |     | 230 |     |     |     |     | 235 |     |     |     |     | 240 |      |
| CCT | GCA | GTG | CAG | TAC | CTA | TCT | CAG | CCA | CAG | CAC | CAG | CCC | TAT | GCT | GTG | 768  |
| Pro | Ala | Val | Gln | Tyr | Leu | Ser | Gln | Pro | Gln | His | Gln | Pro | Tyr | Ala | Val |      |
|     |     |     |     | 245 |     |     |     |     | 250 |     |     |     |     | 255 |     |      |
| CAT | GGC | CAC | TTT | CAG | CCC | ACT | CAG | ACA | GGT | TTC | CTC | CAG | CCT | GGT | GGT | 816  |
| His | Gly | His | Phe | Gln | Pro | Thr | Gln | Thr | Gly | Phe | Leu | Gln | Pro | Gly | Gly |      |
|     |     |     | 260 |     |     |     |     | 265 |     |     |     |     | 270 |     |     |      |
| GCC | CTG | TCC | TTG | CAA | AAG | CAG | ATG | GAA | CAT | GCT | AAC | CAG | CAG | ACT | GGC | 864  |
| Ala | Leu | Ser | Leu | Gln | Lys | Gln | Met | Glu | His | Ala | Asn | Gln | Gln | Thr | Gly |      |
|     |     | 275 |     |     |     |     | 280 |     |     |     |     | 285 |     |     |     |      |
| TTC | TCC | GAC | TCA | TCC | TCT | CTG | CGC | CCC | ATG | CAC | CCC | CAG | GCT | CTG | CAT | 912  |
| Phe | Ser | Asp | Ser | Ser | Ser | Leu | Arg | Pro | Met | His | Pro | Gln | Ala | Leu | His |      |
|     | 290 |     |     |     |     | 295 |     |     |     |     | 300 |     |     |     |     |      |
| CCA | GCC | CCT | GGA | CTC | CTT | GCT | TCC | CCC | CAG | CTC | CCT | GTG | CAG | ATG | CAG | 960  |
| Pro | Ala | Pro | Gly | Leu | Leu | Ala | Ser | Pro | Gln | Leu | Pro | Val | Gln | Met | Gln |      |
| 305 |     |     |     |     | 310 |     |     |     |     | 315 |     |     |     |     | 320 |      |
| CCA | GCA | GGA | AAG | TCG | GCG | TTT | GCA | GCT | ACC | AGC | CAA | CCT | GCG | CCT | CGG | 1008 |
| Pro | Ala | Gly | Lys | Ser | Ala | Phe | Ala | Ala | Thr | Ser | Gln | Pro | Ala | Pro | Arg |      |
|     |     |     |     | 325 |     |     |     |     | 330 |     |     |     |     | 335 |     |      |
| CTC | CCC | TTC | ATC | CAA | CAC | AGC | CAG | AAC | CCG | CAC | TTT | AGA | GCA | CAA | TGG | 1056 |
| Leu | Pro | Phe | Ile | Gln | His | Ser | Gln | Asn | Pro | His | Phe | Arg | Ala | Gln | Trp |      |
|     |     |     | 340 |     |     |     |     | 345 |     |     |     |     | 350 |     |     |      |
| CTG | CAG | ATC | GAT | TAN |     |     |     |     |     |     |     |     |     |     |     | 1071 |
| Leu | Gln | Ile | Asp | Xaa |     |     |     |     |     |     |     |     |     |     |     |      |
|     |     |     | 355 |     |     |     |     |     |     |     |     |     |     |     |     |      |

( 2 ) INFORMATION FOR SEQ ID NO:2:

( i ) SEQUENCE CHARACTERISTICS:
        ( A ) LENGTH: 885 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..884

( x i ) SEQUENCE DESCRIPTION: SEQ ID NO:2:

| GA | ATT | CCG | GTG | GTT | TAC | ACT | GGA | TAT | GGA | AAT | AGA | GAG | GAG | CAA | AAT | 47 |

```
            Ile Pro Val Val Tyr Thr Gly Tyr Gly Asn Arg Glu Glu Gln Asn
             1           5                  10                      15

CTG TCC GAT CTA CTT TCC CCA ATC TGT GAA GTA GCT AAT AAT ATA GAA              95
Leu Ser Asp Leu Leu Ser Pro Ile Cys Glu Val Ala Asn Asn Ile Glu
             20              25                      30

GAG AAT GCT CAA GAG AAT GAA AAT GAA AGC CAA GGT TCA ACA GAT GAA             143
Glu Asn Ala Gln Glu Asn Glu Asn Glu Ser Gln Gly Ser Thr Asp Glu
             35              40                      45

AGT GAG AAC TCC AGG TCT CCT GGA AAT AAA TCA GAT AAC ATC AAG CCC             191
Ser Glu Asn Ser Arg Ser Pro Gly Asn Lys Ser Asp Asn Ile Lys Pro
             50              55                      60

AAA TCT GCT CCA TGG AAC TCT TTT CTC CCT CCA CCC CCC ATG CCA                 239
Lys Ser Ala Pro Trp Asn Ser Phe Leu Pro Pro Pro Pro Met Pro
             65              70                      75

GGG CCA AGA CTG GGA CCA GGA AAG CCA GGT CTA AAA TTC AAT GGC CCA             287
Gly Pro Arg Leu Gly Pro Gly Lys Pro Gly Leu Lys Phe Asn Gly Pro
 80              85                      90                      95

CCA CCG CCA CCG CCA CCA CCA CCA CCC CAC TTA CTA TCA TGC TGG CTG             335
Pro Pro Pro Pro Pro Pro Pro Pro Pro His Leu Leu Ser Cys Trp Leu
                 100             105                     110

CCT CCA TTT CCT TCT GGA CCA CCA ATA ATT CCC CCA CCA CCT CCC ATA             383
Pro Pro Phe Pro Ser Gly Pro Pro Ile Ile Pro Pro Pro Pro Pro Ile
             115             120                     125

TGT CCA GAT TCT CTT GAT GAT GCT GAT GCT TTG GGA AGT ATG TTA ATT             431
Cys Pro Asp Ser Leu Asp Asp Ala Asp Ala Leu Gly Ser Met Leu Ile
             130             135                     140

TCA TGG TAC ATG AGT GGC TAT CAT ACT GGC TAT TAT ATG GGT TTT AGA             479
Ser Trp Tyr Met Ser Gly Tyr His Thr Gly Tyr Tyr Met Gly Phe Arg
             145             150                     155

CAA AAT CAA AAA GAA GGA AGG TGC TCA CAT TCC TTA AAT NNN GGA GAA             527
Gln Asn Gln Lys Glu Gly Arg Cys Ser His Ser Leu Asn Xaa Gly Glu
 160             165                     170                     175

ATG CTG GCA NNN AGC AGC ACT AAA NNN CAC CAC NNN AGA AAC GAT CAG             575
Met Leu Ala Xaa Ser Ser Thr Lys Xaa His His Xaa Arg Asn Asp Gln
             180                     185                     190

ACA GAT CTG GAA TGT GAA GCG TTA NNN AAG ATA ACT GGC CTC ATT TCT             623
Thr Asp Leu Glu Cys Glu Ala Leu Xaa Lys Ile Thr Gly Leu Ile Ser
             195                     200                     205

TCA AAA TAT CAA GTG TTG GGA AAG AAA AAA GGA AGT GGA ATG GGT AAC             671
Ser Lys Tyr Gln Val Leu Gly Lys Lys Lys Gly Ser Gly Met Gly Asn
             210                     215                     220

TCT TCT NNN TTA AAA GTT ATG NNN NNN CCA AAT GCA ATG NNN AAT ATT             719
Ser Ser Xaa Leu Lys Val Met Xaa Xaa Pro Asn Ala Met Xaa Asn Ile
             225                     230                     235

TTA CTG GAC TCT ATT TTG AAA AAC CAT CTG NNN AAG ACT GAG GTG GGG             767
Leu Leu Asp Ser Ile Leu Lys Asn His Leu Xaa Lys Thr Glu Val Gly
 240                     245                     250             255

GTG GGA GGC CAG CAC GGT GGT GAG GCA GTT NNN GAA AAT TTG AAT GTG             815
Val Gly Gly Gln His Gly Gly Glu Ala Val Xaa Glu Asn Leu Asn Val
                 260                     265                     270

GAT NNN ATT TTG AAT GAT ATT GGA NNN TTA TTG GTA ATT TTA ATG AGC             863
Asp Xaa Ile Leu Asn Asp Ile Gly Xaa Leu Leu Val Ile Leu Met Ser
             275                     280                     285

TGT GAG AAG GCT CTA AAG CTT T                                               885
Cys Glu Lys Ala Leu Lys Leu
 290
```

( 2 ) INFORMATION FOR SEQ ID NO:3:

( i ) SEQUENCE CHARACTERISTICS:

(A) LENGTH: 369 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 3..369

(xi) SEQUENCE DESCRIPTION: SEQ ID NO:3:

| CT | GGA | TTT | ACA | CTT | AGG | ATT | TAT | TGT | TAT | TGT | TGT | TGT | TGT | TGT | TTT | 47 |
|---|---|---|---|---|---|---|---|---|---|---|---|---|---|---|---|---|
|  | Gly | Phe | Thr | Leu | Arg | Ile | Tyr | Cys | Tyr | Cys | Cys | Cys | Cys | Cys | Phe |  |
|  | 1 |  |  |  | 5 |  |  |  |  | 10 |  |  |  |  | 15 |  |

| TTA | ATG | ATA | AGC | TAC | TTC | TGC | AAT | TTT | AAC | GTT | GTA | GAA | AAG | ATG | CTA | 95 |
|---|---|---|---|---|---|---|---|---|---|---|---|---|---|---|---|---|
| Leu | Met | Ile | Ser | Tyr | Phe | Cys | Asn | Phe | Asn | Val | Val | Glu | Lys | Met | Leu |  |
|  |  |  |  | 20 |  |  |  |  | 25 |  |  |  |  | 30 |  |  |

| CTA | GTC | TCC | TTT | CAC | CAC | NNN | GGT | GAG | NNN | AGT | GGG | AGG | AAA | TGG | GAA | 143 |
|---|---|---|---|---|---|---|---|---|---|---|---|---|---|---|---|---|
| Leu | Val | Ser | Phe | His | His | Xaa | Gly | Glu | Xaa | Ser | Gly | Arg | Lys | Trp | Glu |  |
|  |  |  | 35 |  |  |  |  | 40 |  |  |  |  | 45 |  |  |  |

| AAG | AGT | GAA | ATA | CTT | AAG | TGC | GAG | GAG | NNN | ACA | TCC | AAG | TGG | CTC | AAG | 191 |
|---|---|---|---|---|---|---|---|---|---|---|---|---|---|---|---|---|
| Lys | Ser | Glu | Ile | Leu | Lys | Cys | Glu | Glu | Xaa | Thr | Ser | Lys | Trp | Leu | Lys |  |
|  |  | 50 |  |  |  |  | 55 |  |  |  |  | 60 |  |  |  |  |

| TTT | TGT | GTC | AGA | AGG | TTT | CAT | TCT | TTA | CAT | TCA | ATG | ACA | AGT | NNN | CAT | 239 |
|---|---|---|---|---|---|---|---|---|---|---|---|---|---|---|---|---|
| Phe | Cys | Val | Arg | Arg | Phe | His | Ser | Leu | His | Ser | Met | Thr | Ser | Xaa | His |  |
|  | 65 |  |  |  |  | 70 |  |  |  |  | 75 |  |  |  |  |  |

| TTA | GGT | GAG | AGG | GAA | AAG | GAG | AAG | AAA | GTC | TGC | CAC | TCT | CCG | CTG | GAT | 287 |
|---|---|---|---|---|---|---|---|---|---|---|---|---|---|---|---|---|
| Leu | Gly | Glu | Arg | Glu | Lys | Glu | Lys | Lys | Val | Cys | His | Ser | Pro | Leu | Asp |  |
| 80 |  |  |  |  | 85 |  |  |  |  | 90 |  |  |  |  | 95 |  |

| CCA | CAA | ACA | TGC | AGA | CCA | GCT | TCT | GTT | AGC | AGA | ACT | CTT | CCA | CAG | NNN | 335 |
|---|---|---|---|---|---|---|---|---|---|---|---|---|---|---|---|---|
| Pro | Gln | Thr | Cys | Arg | Pro | Ala | Ser | Val | Ser | Arg | Thr | Leu | Pro | Gln | Xaa |  |
|  |  |  |  | 100 |  |  |  |  | 105 |  |  |  |  | 110 |  |  |

| GAG | CGC | TCC | TTC | CAG | TGT | AGG | NNN | GAA | NNN | GGT | T |  |  |  |  | 369 |
|---|---|---|---|---|---|---|---|---|---|---|---|---|---|---|---|---|
| Glu | Arg | Ser | Phe | Gln | Cys | Arg | Xaa | Glu | Xaa | Gly |  |  |  |  |  |  |
|  |  |  | 115 |  |  |  |  | 120 |  |  |  |  |  |  |  |  |

(2) INFORMATION FOR SEQ ID NO:4:

(i) SEQUENCE CHARACTERISTICS:
(A) LENGTH: 126 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 3..123

(xi) SEQUENCE DESCRIPTION: SEQ ID NO:4:

| AT | TTT | CTC | CGA | GTA | GAC | CCT | AAA | AGG | ACA | NNN | TTT | TGG | ATG | TCA | GCA | 47 |
|---|---|---|---|---|---|---|---|---|---|---|---|---|---|---|---|---|
|  | Phe | Leu | Arg | Val | Asp | Pro | Lys | Arg | Thr | Xaa | Phe | Trp | Met | Ser | Ala |  |
|  | 1 |  |  |  | 5 |  |  |  |  | 10 |  |  |  |  | 15 |  |

| GTA | CAA | GTA | GTG | AAG | ATA | GCG | ATG | AAG | AGA | ATG | AAG | AAC | NNN | ATA | AAT | 95 |
|---|---|---|---|---|---|---|---|---|---|---|---|---|---|---|---|---|
| Val | Gln | Val | Val | Lys | Ile | Ala | Met | Lys | Arg | Met | Lys | Asn | Xaa | Ile | Asn |  |
|  |  |  |  | 20 |  |  |  |  | 25 |  |  |  |  | 30 |  |  |

| TGC | AGG | CAT | TAC | AGA | AAA | AAG | AAT | AAA | NNN | A |  |  |  |  |  | 126 |
|---|---|---|---|---|---|---|---|---|---|---|---|---|---|---|---|---|
| Cys | Arg | His | Tyr | Arg | Lys | Lys | Asn | Lys | Xaa |  |  |  |  |  |  |  |
|  |  |  | 35 |  |  |  |  | 40 |  |  |  |  |  |  |  |  |

(2) INFORMATION FOR SEQ ID NO:5:

(i) SEQUENCE CHARACTERISTICS:

(A) LENGTH: 357 amino acids
(B) TYPE: amino acid
(D) TOPOLOGY: linear (ii) MOLECULE TYPE: protein (xi) SEQUENCE DESCRIPTION: SEQ ID NO:5:

| Lys | Asn | Ser | His | Cys | Ala | Leu | Lys | Gly | Ser | Gln | Arg | Gln | Pro | Gly | Ala |
|---|---|---|---|---|---|---|---|---|---|---|---|---|---|---|---|
| 1 | | | | 5 | | | | | 10 | | | | | 15 | |
| His | Gly | Pro | Ser | Ala | His | Gly | Ser | Thr | Met | Pro | Ala | Leu | Leu | Glu | Arg |
| | | | 20 | | | | | 25 | | | | | 30 | | |
| Pro | Lys | Leu | Ser | Asn | Ala | Met | Ala | Arg | Gly | Leu | His | Arg | His | Ile | Met |
| | | | 35 | | | | 40 | | | | | 45 | | | |
| Met | Glu | Arg | Glu | Gln | Ala | Gln | Glu | Glu | Glu | Val | Asp | Lys | Met | Met | |
| | 50 | | | | | 55 | | | | | 60 | | | | |
| Glu | Gln | Lys | Met | Lys | Glu | Gln | Glu | Arg | Arg | Lys | Lys | Lys | Glu | Met | |
| 65 | | | | | 70 | | | | 75 | | | | | 80 | |
| Glu | Glu | Arg | Met | Ser | Leu | Glu | Glu | Thr | Lys | Glu | Gln | Ile | Leu | Lys | Leu |
| | | | | 85 | | | | | 90 | | | | | 95 | |
| Glu | Glu | Lys | Leu | Leu | Ala | Leu | Gln | Glu | Glu | Lys | His | Gln | Leu | Phe | Leu |
| | | | 100 | | | | | 105 | | | | | 110 | | |
| Gln | Leu | Lys | Lys | Val | Leu | His | Glu | Glu | Lys | Arg | Arg | Arg | Lys | Glu | |
| | | | 115 | | | | 120 | | | | | 125 | | | |
| Gln | Ser | Asp | Leu | Thr | Thr | Leu | Thr | Ser | Ala | Ala | Tyr | Gln | Gln | Ser | Leu |
| | | 130 | | | | 135 | | | | | 140 | | | | |
| Thr | Val | His | Thr | Gly | Thr | His | Leu | Leu | Ser | Met | Gln | Gly | Ser | Pro | Gly |
| 145 | | | | | 150 | | | | | 155 | | | | | 160 |
| Gly | His | Asn | Arg | Pro | Gly | Thr | Leu | Met | Ala | Ala | Asp | Arg | Ala | Lys | Gln |
| | | | | 165 | | | | | 170 | | | | | 175 | |
| Met | Phe | Gly | Pro | Gln | Val | Leu | Thr | Thr | Arg | His | Tyr | Val | Gly | Ser | Ala |
| | | | 180 | | | | | 185 | | | | | 190 | | |
| Ala | Ala | Phe | Ala | Gly | Thr | Pro | Glu | His | Gly | Gln | Phe | Gln | Gly | Ser | Pro |
| | | 195 | | | | | 200 | | | | | 205 | | | |
| Gly | Gly | Ala | Tyr | Gly | Thr | Ala | Gln | Pro | Pro | Pro | His | Tyr | Gly | Pro | Thr |
| | 210 | | | | | 215 | | | | | 220 | | | | |
| Gln | Pro | Ala | Tyr | Ser | Pro | Ser | Gln | Gln | Leu | Arg | Ala | Pro | Ser | Ala | Phe |
| 225 | | | | | 230 | | | | | 235 | | | | | 240 |
| Pro | Ala | Val | Gln | Tyr | Leu | Ser | Gln | Pro | Gln | His | Gln | Pro | Tyr | Ala | Val |
| | | | | 245 | | | | | 250 | | | | | 255 | |
| His | Gly | His | Phe | Gln | Pro | Thr | Gln | Thr | Gly | Phe | Leu | Gln | Pro | Gly | Gly |
| | | | 260 | | | | | 265 | | | | | 270 | | |
| Ala | Leu | Ser | Leu | Gln | Lys | Gln | Met | Glu | His | Ala | Asn | Gln | Gln | Thr | Gly |
| | | 275 | | | | | 280 | | | | | 285 | | | |
| Phe | Ser | Asp | Ser | Ser | Ser | Leu | Arg | Pro | Met | His | Pro | Gln | Ala | Leu | His |
| | 290 | | | | | 295 | | | | | 300 | | | | |
| Pro | Ala | Pro | Gly | Leu | Leu | Ala | Ser | Pro | Gln | Leu | Pro | Val | Gln | Met | Gln |
| 305 | | | | | 310 | | | | | 315 | | | | | 320 |
| Pro | Ala | Gly | Lys | Ser | Ala | Phe | Ala | Ala | Thr | Ser | Gln | Pro | Ala | Pro | Arg |
| | | | | 325 | | | | | 330 | | | | | 335 | |
| Leu | Pro | Phe | Ile | Gln | His | Ser | Gln | Asn | Pro | His | Phe | Arg | Ala | Gln | Trp |
| | | | 340 | | | | | 345 | | | | | 350 | | |
| Leu | Gln | Ile | Asp | Xaa | | | | | | | | | | | |
| | | | 355 | | | | | | | | | | | | |

(2) INFORMATION FOR SEQ ID NO:6:

(i) SEQUENCE CHARACTERISTICS:
(A) LENGTH: 294 amino acids
(B) TYPE: amino acid
(D) TOPOLOGY: linear (ii) MOLECULE TYPE: protein (xi) SEQUENCE DESCRIPTION: SEQ ID NO:6:

| Ile | Pro | Val | Val | Tyr | Thr | Gly | Tyr | Gly | Asn | Arg | Glu | Glu | Gln | Asn | Leu |
|---|---|---|---|---|---|---|---|---|---|---|---|---|---|---|---|
| 1 | | | | 5 | | | | | 10 | | | | | 15 | |
| Ser | Asp | Leu | Leu | Ser | Pro | Ile | Cys | Glu | Val | Ala | Asn | Asn | Ile | Glu | Glu |
| | | | 20 | | | | 25 | | | | | 30 | | | |
| Asn | Ala | Gln | Glu | Asn | Glu | Asn | Glu | Ser | Gln | Gly | Ser | Thr | Asp | Glu | Ser |
| | | | 35 | | | | 40 | | | | | 45 | | | |
| Glu | Asn | Ser | Arg | Ser | Pro | Gly | Asn | Lys | Ser | Asp | Asn | Ile | Lys | Pro | Lys |
| | 50 | | | | | 55 | | | | | 60 | | | | |
| Ser | Ala | Pro | Trp | Asn | Ser | Phe | Leu | Pro | Pro | Pro | Pro | Met | Pro | Gly |
| 65 | | | | | 70 | | | | | 75 | | | | 80 |
| Pro | Arg | Leu | Gly | Pro | Gly | Lys | Pro | Gly | Leu | Lys | Phe | Asn | Gly | Pro | Pro |
| | | | | 85 | | | | | 90 | | | | | 95 | |
| Pro | Pro | Pro | Pro | Pro | Pro | Pro | Pro | His | Leu | Leu | Ser | Cys | Trp | Leu | Pro |
| | | | 100 | | | | | 105 | | | | | 110 | | |
| Pro | Phe | Pro | Ser | Gly | Pro | Pro | Ile | Ile | Pro | Pro | Pro | Pro | Pro | Ile | Cys |
| | | 115 | | | | | 120 | | | | | 125 | | | |
| Pro | Asp | Ser | Leu | Asp | Asp | Ala | Asp | Ala | Leu | Gly | Ser | Met | Leu | Ile | Ser |
| | 130 | | | | | 135 | | | | | 140 | | | | |
| Trp | Tyr | Met | Ser | Gly | Tyr | His | Thr | Gly | Tyr | Tyr | Met | Gly | Phe | Arg | Gln |
| 145 | | | | | 150 | | | | | 155 | | | | | 160 |
| Asn | Gln | Lys | Glu | Gly | Arg | Cys | Ser | His | Ser | Leu | Asn | Xaa | Gly | Glu | Met |
| | | | | 165 | | | | | 170 | | | | | 175 | |
| Leu | Ala | Xaa | Ser | Ser | Thr | Lys | Xaa | His | His | Xaa | Arg | Asn | Asp | Gln | Thr |
| | | | 180 | | | | | 185 | | | | | 190 | | |
| Asp | Leu | Glu | Cys | Glu | Ala | Leu | Xaa | Lys | Ile | Thr | Gly | Leu | Ile | Ser | Ser |
| | | 195 | | | | | 200 | | | | | 205 | | | |
| Lys | Tyr | Gln | Val | Leu | Gly | Lys | Lys | Lys | Gly | Ser | Gly | Met | Gly | Asn | Ser |
| | 210 | | | | | 215 | | | | | 220 | | | | |
| Ser | Xaa | Leu | Lys | Val | Met | Xaa | Xaa | Pro | Asn | Ala | Met | Xaa | Asn | Ile | Leu |
| 225 | | | | | 230 | | | | | 235 | | | | | 240 |
| Leu | Asp | Ser | Ile | Leu | Lys | Asn | His | Leu | Xaa | Lys | Thr | Glu | Val | Gly | Val |
| | | | | 245 | | | | | 250 | | | | | 255 | |
| Gly | Gly | Gln | His | Gly | Gly | Glu | Ala | Val | Xaa | Glu | Asn | Leu | Asn | Val | Asp |
| | | | 260 | | | | | 265 | | | | | 270 | | |
| Xaa | Ile | Leu | Asn | Asp | Ile | Gly | Xaa | Leu | Leu | Val | Ile | Leu | Met | Ser | Cys |
| | | 275 | | | | | 280 | | | | | 285 | | | |
| Glu | Lys | Ala | Leu | Lys | Leu |
| | 290 | | | | |

(2) INFORMATION FOR SEQ ID NO:7:

(i) SEQUENCE CHARACTERISTICS:
(A) LENGTH: 122 amino acids
(B) TYPE: amino acid
(D) TOPOLOGY: linear (ii) MOLECULE TYPE: protein (xi) SEQUENCE DESCRIPTION: SEQ ID NO:7:

| Gly | Phe | Thr | Leu | Arg | Ile | Tyr | Cys | Tyr | Cys | Cys | Cys | Cys | Cys | Phe | Leu |
|---|---|---|---|---|---|---|---|---|---|---|---|---|---|---|---|
| 1 | | | | 5 | | | | | 10 | | | | | 15 | |

Met Ile Ser Tyr Phe Cys Asn Phe Asn Val Val Glu Lys Met Leu Leu
        20                  25                  30

Val Ser Phe His His Xaa Gly Glu Xaa Ser Gly Arg Lys Trp Glu Lys
        35                  40                  45

Ser Glu Ile Leu Lys Cys Glu Xaa Thr Ser Lys Trp Leu Lys Phe
    50                  55                  60

Cys Val Arg Arg Phe His Ser Leu His Ser Met Thr Ser Xaa His Leu
65                      70                  75                  80

Gly Glu Arg Glu Lys Glu Lys Lys Val Cys His Ser Pro Leu Asp Pro
                85                  90                  95

Gln Thr Cys Arg Pro Ala Ser Val Ser Arg Thr Leu Pro Gln Xaa Glu
            100                 105                 110

Arg Ser Phe Gln Cys Arg Xaa Glu Xaa Gly
            115                 120

( 2 ) INFORMATION FOR SEQ ID NO:8:

( i ) SEQUENCE CHARACTERISTICS:
       ( A ) LENGTH: 41 amino acids
       ( B ) TYPE: amino acid
       ( D ) TOPOLOGY: linear ( i i ) MOLECULE TYPE: protein ( x i ) SEQUENCE DESCRIPTION: SEQ ID NO:8:

Phe Leu Arg Val Asp Pro Lys Arg Thr Xaa Phe Trp Met Ser Ala Val
 1               5                  10                  15

Gln Val Val Lys Ile Ala Met Lys Arg Met Lys Asn Xaa Ile Asn Cys
            20                  25                  30

Arg His Tyr Arg Lys Lys Asn Lys Xaa
            35                  40

( 2 ) INFORMATION FOR SEQ ID NO:9:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:9:

ACCGNNNNCG GT                                                                12

( 2 ) INFORMATION FOR SEQ ID NO:10:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:10:

CTCGGATCCC ATGGAGACAG CATG                                                   24

( 2 ) INFORMATION FOR SEQ ID NO:11:

( i ) SEQUENCE CHARACTERISTICS:
       ( A ) LENGTH: 16 base pairs
       ( B ) TYPE: nucleic acid
       ( C ) STRANDEDNESS: single ( D ) TOPOLOGY: linear ( i i ) MOLECULE TYPE: cDNA ( x i ) SEQUENCE DESCRIPTION: SEQ ID NO:11:

GCTGCCAGCC GTCCTC                                                              16

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

TCGTCACCAA AGCGAG                                                              16

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GCAGATGTTT ACCGATGCCC                                                          20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TACATTAGGT CCTTTGTAGC                                                          20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

GGCGTGAATG TAAGCGTGAC                                                          20

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CCAGGGTGGT AGAGGTG                                                                                        17

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CCTTCGCTAG CGACCCAGAC TC                                                                                  22

( 2 ) INFORMATION FOR SEQ ID NO:18:

( i ) SEQUENCE CHARACTERISTICS:
        ( A ) LENGTH: 404 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..403

( x i ) SEQUENCE DESCRIPTION: SEQ ID NO:18:

```
G GAA CAG AGT GAC CTG ACC ACC CTA ACA TCA GCT GCA TAC CAG CAG        46
  Glu Gln Ser Asp Leu Thr Thr Leu Thr Ser Ala Ala Tyr Gln Gln
  1               5                   10                  15

AGC CTG ACT GTT CAC ACA GGA ACT CAT CTC CTC AGC ATG CAG GGG AGC      94
Ser Leu Thr Val His Thr Gly Thr His Leu Leu Ser Met Gln Gly Ser
                20                  25                  30

CCT GGA GGA CAC AAT CGC CCA GGC ACC CTC ATG GCA GCT GAC AGA GCC     142
Pro Gly Gly His Asn Arg Pro Gly Thr Leu Met Ala Ala Asp Arg Ala
            35                  40                  45

AAA CAA ATG TTT GGA CCC CAA GTG CTT ACG ACC CGG CAC TAC GTG GGC     190
Lys Gln Met Phe Gly Pro Gln Val Leu Thr Thr Arg His Tyr Val Gly
        50                  55                  60

TCA GCA GCT GCT TTT GCA GGG ACA CCA GAG CAT GGA CAA TTC CAA GGC     238
Ser Ala Ala Ala Phe Ala Gly Thr Pro Glu His Gly Gln Phe Gln Gly
    65                  70                  75

AGT CCT GGT GGT GCC TAT GGG ACT GCT CAG CCC CCA CCT CAC TAT GGG     286
Ser Pro Gly Gly Ala Tyr Gly Thr Ala Gln Pro Pro Pro His Tyr Gly
80                  85                  90                  95

CCC ACA CAG CCA GCT TAT AGT CCT AGT CAG CAG CTC AGA GCT CCT TCG     334
Pro Thr Gln Pro Ala Tyr Ser Pro Ser Gln Gln Leu Arg Ala Pro Ser
                100                 105                 110

GCA TTC CCT GCA GTG CAG TTA CCT ATC TTC AGC CAC AGC CAC AGG CCT     382
Ala Phe Pro Ala Val Gln Leu Pro Ile Phe Ser His Ser His Arg Pro
            115                 120                 125

ATT GCT GTG CAT GGG CCA TTT T                                       404
Ile Ala Val His Gly Pro Phe
            130
```

( 2 ) INFORMATION FOR SEQ ID NO:19:

( i ) SEQUENCE CHARACTERISTICS:
        ( A ) LENGTH: 134 amino acids
        ( B ) TYPE: amino acid
        ( D ) TOPOLOGY: linear (ii) MOLECULE TYPE: protein (xi) SEQUENCE DESCRIPTION: SEQ ID NO:19:

```
Glu Gln Ser Asp Leu Thr Thr Leu Thr Ser Ala Ala Tyr Gln Gln Ser
 1               5                  10                 15
Leu Thr Val His Thr Gly Thr His Leu Leu Ser Met Gln Gly Ser Pro
             20                  25                 30
Gly Gly His Asn Arg Pro Gly Thr Leu Met Ala Ala Asp Arg Ala Lys
         35                  40                 45
Gln Met Phe Gly Pro Gln Val Leu Thr Thr Arg His Tyr Val Gly Ser
     50                  55                 60
Ala Ala Ala Phe Ala Gly Thr Pro Glu His Gly Gln Phe Gln Gly Ser
65                  70                  75                 80
Pro Gly Gly Ala Tyr Gly Thr Ala Gln Pro Pro Pro His Tyr Gly Pro
             85                  90                 95
Thr Gln Pro Ala Tyr Ser Pro Ser Gln Gln Leu Arg Ala Pro Ser Ala
             100                 105                110
Phe Pro Ala Val Gln Leu Pro Ile Phe Ser His Ser His Arg Pro Ile
             115                 120                125
Ala Val His Gly Pro Phe
             130
```

METHOD FOR DETERMINING COMPOUND INTERACTION WITH E2 BINDING PROTEINS

This application is a divisional application of U.S. Ser. No. 08/361,806 filed on Dec. 22, 1994, pending. The contents of all of the aforementioned application are hereby incorporated by reference.

GOVERNMENT FUNDING

Work described herein was supported in part by funding from the National Institute of Health, Grant number RO1CA58376. The United States Government has certain rights in the invention.

BACKGROUND OF THE INVENTION

Papillomaviruses (PV) have been linked to widespread, serious human diseases, especially carcinomas of the genital and oral mucosa. Tens of millions of women suffer from human papilloma virus (HPV) infection of the genital tract. Significant number of these women eventually develop cancer of the cervix. It has been estimated that perhaps twenty percent (20%) of all cancer deaths in women worldwide are from cancers which are associated with HPV. As many as 90% of all cervical cancer maybe linked to HPV.

Papillomaviruses also induce benign, dysplastic and malignant hyperproliferations of skin and mucosal epithelium (see, for example, Mansur and Androphy, (1993) Biochim Biophys Acta 1155:323–345; Pfister (1984) Rev. Physiol. Biochem. Pharmacol. 99:111–181; and Broker et al. (1986) Cancer Cells 4:17–36, for reviews of the molecular, cellular, and clinical aspects of the papillomaviruses).

HPV's are a heterogeneous group of DNA tumor viruses associated with hyperplastic (warts, condylomata), pre-malignant and malignant lesions (carcinomas) of squamous epithelium. Almost 70 HPV types have been identified, and different papillomavirus types are known to cause distinct diseases, Pfister, (1987) Adv. Cancer Res., 48:113–147, Syrjanen, (1984) Obstet. GynecoL Survey 39:252–265. For example, HPV types 1 and 2 cause common warts, and types 6 and 11 cause warts of the external genitalia, anus and cervix. HPV's can be isolated from the majority of cervical cancers. Types 16, 18, 31 and 33 are particularly common; HPV-16 is present in about 50 percent of all cervical cancers. These HPV's are referred to as "high risk" HPV's. While HPV 6 and 11 are common isolates for cervical papillomas, these infections rarely progress to invasive cancer, and therefore these HPV's are referred to as "low risk" HPV's.

The biological life cycle of the papillomaviruses appears to differ from most other viral pathogens. These viruses are believed to infect the basal or germ cells of the epithelium. Rather than proceeding to a lytic infection in which viral replication kills the cell, viral DNA transcription and replication are maintained at very low levels until higher strata of the epithelium are achieved. There, presumably in response to differentiation-specific signals, viral transcription accelerates, DNA synthesis begins and virions assemble. It is within this terminally differentiating cellular environment that the virus must recruit the panoply of cellular factors necessary for its reproduction.

The product of the E2 open reading frame plays an important role in the complex transcriptional pattern of the HPV's. The E2 transcriptional activation protein ("the E2 protein") is a trans-acting factor that activates transcription through specific binding to cisacting E2 enhancer sequences in viral DNA (Androphy et al., (1987) Nature, 324:70–73), and has been shown to induce promoter expression in a classical enhancer mechanism (Spalholz et al., (1985) Cell 42:183–91). The E2 gene product exerts trans-regulatory effects in the upstream regulatory region ("URR") of the viral genome and disruption of E2 is thought to alter regulation of expression of E6 and E7 genes. The upstream regulatory region is found immediately 5' to the early genes of bovine papilloma viruses (BPV's) and other papillomaviruses. The URR contains cis-acting regulatory signals, including an origin of DNA replication and several promoters that function in early transcription. The URR also contains enhancer elements that activate transcription from the URR promoters and heterologous promoters (Sousa et al., (1990) Biochemica et Biophysica Acta 1032: 19–37).

The E2 enhancer elements are conditional, in that they stimulate transcription only when activated by a protein encoded by the E2 open reading frame. As with other transcription factors, the functions of E2 protein appear to be localized to discrete modular domains (Giri et al., (1988) EMBO J., 7:2923–29). Gene products from the E2 gene include the full-length transcriptional activator E2 protein and at least two truncated versions of the E2 protein BPV1 that function as transcriptional repressors. Transcriptional activation and repression of viral genes by E2 gene products constitute critical regulatory circuits in papillomavirus gene expression and DNA replication.

Within the URR, transcriptional regulation by the E2 protein depends on its direct binding to the nucleotide sequence 5'ACC(G)NNNN(C)GGT3'(SEQ ID NO:9) (Androphy et al., supra; Dartmann et al., (1986) Virology, 151:124–30; Hirochika et al., (1987) J. Virol, 61:2599–606; P. Hawley-Nelson et al., (1988) EMBO J., 7:525–31; McBride et al., (1988) EMBO J., 7:533–39). In that sequence, N represents any nucleotide; X is any nucleotide, but is usually G; and Y represents any nucleotide, but is usually C. E2 binding sites appear to be positioned in close proximity to the viral promoters, with multiple E2 binding sites present throughout the papillomavirus genome (R. Li et al., (1989) Genes Dev., 3: 510–26), in the URR's of all papillomaviruses, as well as in other sites near promoters throughout the viral genome. Moreover, E2 binding sites may fuction as an element in viral DNA replication, as well as a classical transcriptional enhancer element.

SUMMARY OF THE INVENTION

The present invention relates, in part, to the discovery in eukaryotic cells, particularly human cells, of novel protein-protein interactions between the papillomavirus regulatory protein E2 and certain cellular proteins, referred to hereinafter as "E2-binding proteins" or "E2-BP", some of which, e.g., E2-BP$^{42A}$, E2-BP$^{23}$, E2-BP$^{24}$, and E2-BP$^{2-7}$ are themselves novel proteins.

Accordingly, the invention features, a E2-BP$^{42A}$ polypeptide, preferably a substantially pure preparation of an E2-BP$^{42A}$ polypeptide, or a recombinant E2-B$^{42A}$ polypeptide. In preferred embodiments: the polypeptide has biological activity, e.g., it specifically binds a papillomavirus E2 protein; the polypeptide has an amino acid sequence at least 60%, 80%, 90% or 95% homologous to the amino acid sequence in SEQ ID NO:5; the polypeptide has an amino acid sequence essentially the same as the amino acid sequence in SEQ ID NO:5; the polypeptide is at least 5, 10, 20, 50, 100, or 150 amino acids in length; the polypeptide includes at least 5, preferably at least 10, more preferably at least 20, more preferably at least 50, 100, or 150 contiguous amino acids from SEQ ID NO:5; the E2-BP$^{42A}$ polypeptide is either, an agonist or an antagonist, of a biological activity of a naturally occurring E2-binding protein. For example, the E2-BP$^{42A}$ polypeptide is an agonist or antagonist of the regulation of E2 function, e.g. of E2-mediated transcription of PV oncogenes. (As described in the examples below, an exemplary E2-BP which is antagonistic of E2 transcriptional activation is the portion of the 42A clone initially isolated, 357 amino acid fragment, in the E2-mediated two hybrid assay. (When expressed without the VP16 domain (i.e. not as a VP16/42A fusion protein), the 42A polypeptide was able to inhibit transactivation of the reporter construct by the wild-type E2 protein.)

In preferred embodiments: the E2-BP42A polypeptide is encoded by the nucleic acid in SEQ ID NO:1, or by a nucleic acid having at least 60%, 70%, 80%, 90% or 95% homology with the nucleic acid of SEQ ID NO:1.

In a preferred embodiment, the subject E2-BP$^{42A}$ polypeptide differs in amino acid sequence at 1, 2, 3, 5, 10 or more residues, from the sequence in SEQ ID NO:5. The differences, however, are such that: the E2-BP polypeptide exhibits an E2-BP biological activity, e.g., the E2-BP$^{42A}$ polypeptide retains a biological activity of a naturally occurring E2-BP$^{42A}$, e.g., the E2-BP$^{42A}$ of SEQ ID NO:5.

In yet other preferred embodiments, the E2-binding protein is a recombinant fusion protein having a first E2-BP portion and a second polypeptide portion, e.g., a second polypeptide portion having an amino acid sequence unrelated to E2-BP$^{42A}$. The second polypeptide portion can be any of glutathione-S-transferase, a DNA binding domain, or a polymerase activating domain. In preferred embodiment the fusion protein can be used in a two-hybrid assay.

In a preferred embodiment the E2-BP polypeptide encodes amino acid residues 40–259 of SEQ ID NO:5.

In preferred embodiments the E2-binding polypeptide has antagonistic activity, and is capable of: suppressing tumor growth, e.g. in a tumor cell in which endogenous E2-BP is misexpressed; suppressing growth of papillomavirus-infected cells, e.g. HPV-infected cells; inhibiting growth of a papillomavirus-infected cell, e.g., an HPV-infected cell, e.g., a low-risk or a high-risk HPV-infected cell, e.g., and HPV-16, -18, -31 infected cell, e.g., a bovine papillomavirus (BPV); inhibiting infection of a cell by a papillomavirus, e.g., an HPV, e.g., a high-risk HPV, e.g., and HPV-16, -18, -31, or 33, e.g. a bovine papillomavirus (BPV); inhibiting transformation of a cell by a papillomavirus, e.g., an HPV, e.g., a high-risk HPV, e.g., and HPV-16, -18, -31, or 33, e.g. a human cell, by a papillomavirus, e.g., an HPV, e.g., a high-risk HPV, e.g., and HPV-16,-18, -31, or 33, e.g. a bovine papillomavirus; inhibiting the growth of, or diminishing the size of a wart.

In a preferred embodiment, the E2-BP polypeptide is a fragment of E2-BP$^{42A}$ which inhibits the E2 transcriptional activation.

The invention includes an immunogen which includes an E2-BP$^{42A}$ polypeptide in an immunogenic preparation, the immunogen being capable of eliciting an immune response specific for said E2-BP$^{42A}$ polypeptide, e.g., a humoral response, an antibody response, or a cellular response. In preferred embodiments, the immunogen comprising an antigenic determinant, e.g., a unique determinant, from a protein represented by SEQ ID NO:5.

The present invention also includes an antibody preparation specifically reactive with an epitope of the E2-BP$^{42A}$ immunogen or generally of an E2-BP$^{42A}$ polypeptide.

In a preferred embodiment the E2-BP polypeptide differs in amino acid sequence from the amino acid sequence of residues 130–262 of SEQ ID NO:5.

In yet a further preferred embodiment, the E2-BP polypeptide is other than the amino acid sequence 130–262 of SEQ ID NO:5, e.g., it differs from residues 130–262 of SEQ ID NO:5 by at least one amino acid residue, e.g., the E2-BP polypeptide is at least one amino acid residue shorter, one amino acid residue longer, differs in sequence at least at one position, has a different N terminus, or has a different C terminus, as compared with residues 130–262 of SEQ ID NO:5. In preferred embodiments, the E2-BP polypeptide is encoded by a nucleic acid which hybridizes to a nucleic acid corresponding to a sequence encoding at least 4 consecutive amino acids, more preferably at least 10 consecutive amino acid residues, and even more preferably at least 20 amino acid residues between residues 1 and 129, or between residues 263 and 357, of SEQ ID NO:5. In a preferred embodiment: the E2-BP polypeptide includes at least 1, 2, 3 or 5, and preferably at least 10, 20, or 50 amino acid residues from the region of SEQ ID NO:5 which encodes amino acid residues 1–129, or between residues 263–357.

In a preferred embodiment the E2-BP polypeptide differs in amino acid sequence from the amino acid sequence of residues 1–134 of SEQ ID NO:19.

In yet a further perferred embodiment, the E2-BP polypeptide is other than the amino acid sequence 1–134 of SEQ ID NO:19, e.g., it differs from residues 1–134 of SEQ ID NO:19 by at least one amino acid residue, e.g., the E2-BP polypeptide is at least one amino acid residue shorter, one amino acid residue longer, differs in sequence at least at one position, has a different N terminus, or has a different C terminus, as compared with residues 1–134 of SEQ ID NO:19.

In a preferred embodiment the E2-BP polypeptide differs in amino acid sequence from the amino acid sequence encoded by vector EST 01427 described in WO 93/00353 and deposited with the American Type Culture Collection under the designation EST 01427 and subsequently assigned ATCC deposit number 78895

In yet a further preferred embodiment, the E2-BP polypeptide is other than the amino acid sequence encoded by vector EST 01427, e.g., it differs from the amino acid sequence encoded by vector EST 01427 by at least one amino acid residue, e.g., the E2-BP polypeptide is at least one amino acid residue shorter, one amino acid residue longer, differs in sequence at least at one position, has a different N terminus, or has a different C terminus, as compared with the amino acid sequence encoded by vector EST 01427.

In another aspect, the invention features, a E2-BP$^{SD-23}$ polypeptide, preferably a substantially pure preparation of an E2-BP$^{SD-23}$ polypeptide, or a recombinant E2-BP$^{SD-23}$ polypeptide. In preferred embodiments: the polypeptide has biological activity, e.g., it specifically binds a papillomavirus E2 protein; the polypeptide has an amino acid sequence at least 60%, 80%, 90% or 95% homologous to the amino acid sequence in SEQ ID NO:7; the polypeptide has an amino acid sequence essentially the same as the amino acid sequence in SEQ ID NO:7; the polypeptide is at least 5, 10, 20, 50, 100, or 150 amino acids in length; the polypeptide includes at least 5, preferably at least 10, more preferably at least 20, more preferably at least 50, 100, or 150 contiguous amino acids from SEQ ID NO:7; the E2-BP$^{SD23}$ polypeptide is either, an agonist or an antagonist, of a biological activity of a naturally occurring E2-BP. For example, the E2-BP$^{SD-23}$ polypeptide is an agonist or antagonist of the regulation of E2 function, e.g. of E2-mediated transcription of PV oncogenes.

In preferred embodiments: the E2-BP$^{SD-23}$ polypeptide is encoded by the nucleic acid in SEQ ID NO:3, or by a nucleic acid having at least 60%, 70%, 80%, 90% or 95% homology with the nucleic acid of SEQ ID NO:3.

In a preferred embodiment, a subject E2-BP$^{SD-23}$ polypeptide differs in amino acid sequence at 1, 2, 3, 5, 10 or more residues, from the sequence in SEQ ID NO:7. The differences, however, are such that: the E2-BP polypeptide exhibits an E2-BP biological activity, e.g., the E2-BP$^{SD-23}$ polypeptide retains a biological activity of a naturally occurring E2-BP$^{23}$, e.g., the E2-BP$^{SD-23}$ of SEQ ID NO:7.

In yet other preferred embodiments, the E2-binding protein is a recombinant fusion protein having a first E2-BP portion and a second polypeptide portion, e.g., a second polypeptide portion having an amino acid sequence unrelated to E2-BP$^{SD-23}$. The second polypeptide portion can be any of glutathione-S-transferase; a DNA binding domain; or a polymerase activating domain. In preferred embodiments the fusion protein can be used in a two-hybrid assay.

In preferred embodiments the E2-binding polypeptide has antagonistic activity, and is capable of: suppressing tumor growth, e.g., in a tumor cell in which endogenous E2-BP is misexpressed; suppressing growth of papillomavirus-infected cells, e.g., HPV-infected cells; inhibiting growth of a papillomavirus-infected cell, e.g., an HPV-infected cell, e.g., a low-risk or a high-risk HPV-infected cell, e.g., and HPV-16, -18, -31 infected cell, e.g., a bovine papillomavirus (BPV); inhibiting infection of a cell by a papillomavirus, e.g., an HPV, e.g., a high-risk HPV, e.g., and HPV-16, -18, -31, or 33, e.g., a bovine papillomavirus (BPV); inhibiting transformation of a cell by a papillomavirus, e.g., an HPV, e.g., a high-risk HPV, e.g., and HPV-16, -18, -31, or 33, e.g., a human cell, by a papillomavirus, e.g., an HPV, e.g., a high-risk HPV, e.g., and HPV-16, -18, -31, or 33, e.g., a bovine papillomavirus; inhibiting the growth of, or diminishing the size of a wart.

The invention includes an immunogen which includes an E2-BP$^{SD-23}$ polypeptide in an immunogenic preparation, the immunogen being capable of eliciting an immune response specific for said E2-BP$^{SD-23}$ polypeptide, e.g., a humoral response, an antibody response, or a cellular response. In preferred embodiments, the immunogen includes an antigenic determinant, e.g., a unique determinant, from a protein represented by SEQ ID NO:7.

The invention also includes an antibody preparation specifically reactive with an epitope of the E2-BP$^{SD-23}$ immunogen or generally of an E2-BP$^{SD-23}$ polypeptide.

In another aspect, the invention features, a E2-BP$^{SD-24}$ polypeptide, preferably a substantially pure preparation of an E2-BP$^{SD-24}$ polypeptide, or a recombinant E2-BP$^{SD-24}$ polypeptide. In preferred embodiments: the polypeptide has biological activity, e.g., it specifically binds a papillomavirus E2 protein; the polypeptide has an amino acid sequence at least 60%, 80%, 90% or 95% homologous to the amino acid sequence in SEQ ID NO:8; the polypeptide has an amino acid sequence essentially the same as the amino acid sequence in SEQ ID NO:8; the polypeptide is at least 5, 10, 20, 50, 100, or 150 amino acids in length; the polypeptide includes at least 5, preferably at least 10, more preferably at least 20, more preferably at least 50, 100, or 150 contiguous amino acids from SEQ ID NO:8; the E2-BP$^{SD-24}$ polypeptide is either, an antagonist or an antagonist, of a biological activity of a naturally occurring E2-BP. For example, the E2-BP$^{SD-24}$ polypeptide is an agonist or antagonist of the regulation of E2 function, e.g., of E2-mediated transcription of PV oncogenes.

In preferred embodiments: the E2-BP$^{SD-24}$ polypeptide is encoded by the nucleic acid in SEQ ID NO:4, or by a nucleic acid having at least 60%, 70%, 80%, 90% or 95% homology with the nucleic acid of SEQ ID NO:4.

In a preferred embodiment, the subject E2-BP$^{SD-24}$ polypeptide differs in amino acid sequence at 1, 2, 3, 5, 10 or more residues, from the sequence in SEQ ID NO:8. The differences, however, are such that: the E2-BP polypeptide exhibits an E2-BP biological activity, e.g., the E2-BP$^{SD-24}$ polypeptide retains a biological activity of a naturally occurring E2-BP$^{SD-24}$, e.g., the E2-BP$^{SD-24}$ of SEQ ID NO:8.

In yet other preferred embodiments, the subject E2-binding protein is a recombinant fusion protein having a first E2-BP portion and a second polypeptide portion, e.g., a second polypeptide portion having an amino acid sequence unrelated to the E2-BP$^{SD-24}$. The second polypeptide portion can be, e.g., any of: glutathione-S-transferase; a DNA domain; or a polymerase activating domain. In preferred embodiments the fusion protein is finctional in a two-hybrid assay.

The invention includes an immunogen which includes an E2-BP$^{SD-24}$ polypeptide in an immunogenic preparation, the immunogen being capable of eliciting an immune response specific for the E2-BP$^{SD-24}$ polypeptide, e.g., a humoral response; an antibody response; or a cellular response. In preferred embodiments, the immunogen comprising an antigenic determinant, e.g., a unique determinant, from a protein represented by SEQ ID NO:8.

The invention also includes an antibody preparation specifically reactive with an epitope of the E2-BP$^{SD-24}$ immunogen or generally of an E2-BP$^{SD-24}$ polypeptide.

In preferred embodiments the E2-binding polypeptide has antagonistic activity, and is capable of: suppressing tumor growth, e.g., in a tumor cell in which endogenous E2-BP is misexpressed; suppressing growth of papillomavirus-infected cells, e.g., HPV-infected cells; inhibiting growth of a papillomavirus-infected cell, e.g., an HPV-infected cell, e.g., a low-risk or a high-risk HPV-infected cell, e.g., and HPV-16, -18, -31 infected cell, e.g., a bovine papillomavirus (BPV); inhibiting infection of a cell by a papillomavirus, e.g., an HPV, e.g., a high-risk HPV, e.g., and HPV-16, -18, -31, or 33, e.g., a bovine papillomavirus (BPV); inhibiting transformation of a cell by a papillomavirus, e.g., an HPV, e.g., a high-risk HPV, e.g., and HPV-16, -18, -31, or 33, e.g., a human cell, by a papillomavirus, e.g., an HPV, e.g., a high-risk HPV, e.g., and HPV-16, -18, -31, or 33, e.g., a bovine papillomavirus; inhibiting the growth of, or diminishing the size of a wart.

In another aspect, the invention features, a E2-BP$^{SD2-7}$ polypeptide, preferably a substantially pure preparation of an E2-BP$^{SD2-7}$ polypeptide, or a recombinant E2-BP$^{SD2-7}$ polypeptide. In preferred embodiments: the polypeptide has biological activity, e.g., it specifically binds a papillomavirus E2 protein; the polypeptide has an amino acid sequence at least 60%, 80%, 90% or 95% homologous to the amino acid sequence in SEQ ID NO:6; the polypeptide has an amino acid sequence essentially the same as the amino acid sequence in SEQ ID NO:6; the polypeptide is at least 5, 10, 20, 50, 100, or 150 amino acids in length; the polypeptide includes at least 5, preferably at least 10, more preferably at least 20, more preferably at least 50, 100, or 150 contiguous amino acids from SEQ ID NO:6; the E2-BP$^{SD2-7}$ polypeptide is either, an antagonist or an antagonist, of a biological activity of a naturally occurring E2-BP. For example, the E2-BP$^{SD2-7}$ polypeptide is an agonist or antagonist of the regulation of E2 function, e.g. of E2-mediated transcription of PV oncogenes.

In preferred embodiments: the E2-BP$^{SD2-7}$ polypeptide is encoded by the nucleic acid in SEQ ID NO:2, or by a nucleic acid having at least 60%, 70%, 80%, 90% or 95% homology with the nucleic acid of SEQ ID NO:2.

In a preferred embodiment, the subject E2-BP$^{SD2-7}$ polypeptide differs in amino acid sequence at 1, 2, 3, 5, 10 or more residues, from the sequence in SEQ ID NO:6. The differences, however, are such that: the E2-BP polypeptide exhibits an E2-BP biological activity, e.g., the E2-BP$^{SD2-7}$ polypeptide retains a biological activity of a naturally occurring E2-BP$^{SD2-7}$, e.g., the E2-BP$^{SD2-7}$ of SEQ ID NO:2.

In yet other preferred embodiments, the subject E2-binding protein is a recombinant fusion protein having a first E2-BP portion and a second polypeptide portion, e.g., a second polypeptide portion having an amino acid sequence unrelated to the E2-BP$^{SD2-7}$. The second polypeptide portion can be e.g., any of: glutathione-S-transferase; a DNA domain; or a polymerase activating domain. In preferred embodiments the fusion protein is functional in a two-hybrid assay.

The invention includes an immunogen which includes an E2-BP$^{SD2-7}$ polypeptide in an immunogenic preparation, the immunogen being capable of eliciting an immune response specific for the E2-BP$^{SD2-7}$ polypeptide, e.g., a humoral response; an antibody response; or a cellular response. In preferred embodiments, the immunogen comprising an antigenic determinant, e.g., a unique determinant, from a protein represented by SEQ ID NO:6.

The invention also includes an antibody preparation specifically reactive with an epitope of the E2-BP$^{SD2-7}$ immunogen or generally of an E2-BP$^{SD2-7}$ polypeptide.

In preferred embodiments the E2-binding polypeptide has antagonistic activity, and is capable of: suppressing tumor growth, e.g., in a tumor cell in which endogenous E2-BP is misexpressed; suppressing growth of papillomavirus-infected cells, e.g., HPV-infected cells; inhibiting growth of a papillomavirus-infected cell, e.g., an HPV-infected cell, e.g., a low-risk or a high-risk HPV-infected cell, e.g., and HPV-16, -18, -31 infected cell, e.g., a bovine papillomavirus (BPV); inhibiting infection of a cell by a papillomavirus, e.g., an HPV, e.g., a high-risk HPV, e.g., and HPV-16, -18, -31, or 33, e.g., a bovine papillomavirus (BPV); inhibiting transformation of a cell by a papillomavirus, e.g., an HPV, e.g., a high-risk HPV, e.g., and HPV-16, -18, -31, or 33, e.g. a human cell, by a papillomavirus, e.g., an HPV, e.g., a high-risk HPV, e.g., and HPV-16, -18, -31, or 33, e.g., a bovine papillomavirus; inhibiting the growth of, or diminishing the size of a wart.

Another aspect of the present invention provides a substantially pure nucleic acid having a nucleotide sequence which encodes an E2-BP$^{42A}$ polypeptide. In preferred embodiments: the encoded polypeptide has biological activity, e.g., it specifically binds a papillomavirus E2 protein; the encoded polypeptide has an amino acid sequence at least 60%, 80%, 90% or 95% homologous to the amino acid sequence in SEQ ID NO:5; the encoded polypeptide has an amino acid sequence essentially the same as the amino acid sequence in SEQ ID NO:5; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:5; the encoded E2-BP$^{42A}$ polypeptide is either, an agonist or an antagonist, of a biological activity of a naturally occurring E2-BP. For example, the encoded E2-BP$^{42A}$ polypeptide is an agonist or antagonist of the regulation of E2 function, e.g. of E2-mediated transcription of PV oncogenes. (As described in the examples below, an exemplary E2-BP which is antagonistic of E2 transcriptional activation is the portion of the 42A clone initially isolated, 357 amino acid residues long, in the E2-mediated two hybrid assay. (When expressed without the VP16 domain (i.e. not as a VP16/42A fusion protein), the 42A polypeptide was able to inhibit transactivation of the reporter construct by the wild-type E2 protein.)

In preferred embodiments: the nucleic acid is that of SEQ ID NO:1; the nucleic acid is at least 60%, 70%, 80%, 90% or 95% homologous with the nucleic acid sequence of SEQ ID NO:1.

In preferred embodiments the encoded polypeptide has antagonistic activity, and is preferably capable of: suppressing tumor growth, e.g., in a tumor cell in which endogenous E2-BP is misexpressed; suppressing growth of papillomavirus-infected cells, e.g., HPV-infected cells; inhibiting growth of a papillomavirus-infected cell, e.g., an HPV-infected cell, e.g., a low-risk or a high-risk HPV infected cell, e.g., and HPV-16, -18, -31, or -33 infected cell, e.g., a bovine papillomavirus (BPV)-infected cell; inhibiting infection of a cell by a papillomavirus, e.g., an HPV, e.g., a high-risk HPV, e.g., and HPV-16, -18, -31, or -33, e.g. a bovine papillomavirus (BPV); inhibiting transformation of a cell by a papillomavirus, e.g., an HPV, e.g., a high-risk HPV, e.g., and HPV-16, -18, -31, or -33, e.g., a bovine papillomavirus; or inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; inhibiting the growth of, or diminishing the size of a wart.

In a preferred embodiment, the encoded E2-BP$^{42A}$ polypeptide differs in amino acid sequence at 1, 2, 3, 5, 10 or more residues, from the sequence in SEQ ID NO:5. The differences, however, are such that: the E2-BP encoded polypeptide exhibits an E2-BP biological activity, e.g., the encoded E2-BP$^{42A}$ polypeptide retains a biological activity of a naturally occurring E2-BP$^{42A}$, e.g., the E2-BP$^{42A}$ of SEQ ID NO:5.

In yet other preferred embodiments, the encoded polypeptide is a recombinant fusion protein having a first E2-BP portion and a second polypeptide portion, e.g., a second polypeptide portion having an amino acid sequence unrelated to the E2-BP$^{42A}$. The second polypeptide portion can be glutathione-S-transferase; a DNA binding domain; or a polymerase activating domain. In preferred embodiments the fusion protein can be used in a two-hybrid assay.

In preferred embodiments, the subject E2-BP$^{42A}$ nucleic acid will include a transcriptional regulatory sequence, e.g. at least one of a transcriptional promoter or transcriptional enhancer sequence, operably linked to the E2-BP$^{42A}$ gene sequence, e.g., to render the E2-BP$^{42A}$ gene sequence suitable for use as an expression vector.

In yet a further preferred embodiment, the nucleic acid which encodes an E2-BP$^{42A}$ polypeptide of the invention, hybridizes under stringent conditions to a nucleic acid probe corresponding to at least 12 consecutive nucleotides of SEQ ID NO:1; more preferably to at least 20 consecutive nucleotides of SEQ ID NO:1; more preferably to at least 40 consecutive nucleotides of SEQ ID NO:1.

In a preferred embodiment the E2-BP encoding nucleic acid sequence encodes amino acid residues 40–259 of SEQ ID NO:5.

In a preferred embodiment, the nucleic acid encodes a peptide which differs by at least one amino acid residue from the region of 130–262 of SEQ ID NO:5.

In a preferred embodiment, the nucleic acid differs by at least one nucleotide from the nucleotide sequence which encodes amino acids 130–262 of SEQ ID NO:5.

In yet a further preferred embodiment, the E2-BP encoding nucleic acid is other than a nucleic acid sequence which encodes the amino acid sequence 130–262 of SEQ ID NO:5, e.g., it differs from a sequence which encodes residues 130–262 of SEQ ID NO:5 by at least one nucleotide, e.g., the E2-BP encoding nucleic acid is at least one nucleotide shorter, one nucleotide longer, differs in sequence at least one position, has a different 5' terminus, or has a different 3' terminus, as compared with a sequence which encodes residues 130–262 of SEQ ID NO:5. In preferred embodiments, the E2-BP encoding nucleic acid hybridizes to a nucleic acid corresponding to a sequence encoding at least 4 consecutive amino acids, more preferably at least 10 consecutive amino acid residues, and even more preferably at least 20 amino acid residues between residues 1 and 129, or between residues 263 and 357, of SEQ ID NO:5. In a preferred embodiment: the E2-BP encoding nucleic acid sequence includes at least 1, 2, 3 or 5, and preferably at least 10, 20, 50, or 100 nucleotides from the region of SEQ ID NO:5 which encodes amino acid residues 1–129, or between residues 263–357, of SEQ ID NO:5.

In a preferred embodiment, the nucleic acid encodes a peptide which differs by at least one amino acid residue from the region of 1–134 of SEQ ID NO:19.

In a preferred embodiment, the nucleic acid differs by at least one nucleotide from the nucleotide sequence which encodes amino acids 1–134 of SEQ ID NO:19.

In yet a further preferred embodiment, the E2-BP encoding nucleic acid is other than a nucleic acid sequence which encodes the amino acid sequence 1–134 of SEQ ID NO:19, e.g., it differs from a sequence which encodes residues 1–134 of SEQ ID NO:19 by at least one nucleotide, e.g., the E2-BP encoding nucleic acid is at least one nucleotide shorter, one nucleotide longer, differs in sequence at least one position, has a different 5' terminus, or has a different 3' terminus, as compared with a sequence which encodes residues 1–134 of SEQ ID NO:19.

In a preferred embodiment, the nucleic acid encodes a peptide which differs by at least one amino acid residue from the amino acid sequence encoded by vector EST 01427 described in WO 93/00353 and deposited with the American Type Culture Collection under the designation ESR 01427 and subsequently assigned ATCC deposit number 78895.

In a preferred embodiment, the nucleic acid differs by at least one nucleotide from the nucleotide sequence in vector EST 01427 described in WO 93/00353 and deposited with the American Type Culture Collection under the designation EST 01427 and subsequently assigned ATCC deposit number 78895.

In yet a further preferred embodiment, the E2-BP encoding nucleic acid is other than a nucleic acid sequence which encodes the amino acid sequence encoded by vector EST 01427, e.g., it differs from the sequence encoded by vector EST 01427 by at least one nucleotide, e.g., the E2-BP encoding nucleic acid is at least one nucleotide shorter, one nucleotide longer, differs in sequence at least one position, has a different 5' terminus, or has a different 3' terminus, as compared with a sequence encoded by vector EST 01427.

Another aspect of the present invention provides a substantially pure nucleic acid having a nucleotide sequence which encodes an E2-BP$^{SD-23}$ polypeptide. In preferred embodiments: the encoded polypeptide has biological activity, e.g., it specifically binds a papillomavirus E2 protein; the encoded polypeptide has an amino acid sequence at least 60%, 80%, 90% or 95% homologous to the amino acid sequence in SEQ ID NO:7, the encoded polypeptide has an amino acid sequence essentially the same as the amino acid sequence in SEQ ID NO:7; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:7; the encoded E2-BP$^{SD-23}$ polypeptide is either, an agonist or an antagonist, of a biological activity of a naturally occurring E2-BP. For example, the encoded E2-BP$^{SD-23}$ polypeptide is an agonist or antagonist of the regulation of E2 function, e.g. of E2-mediated transcription of PV oncogenes.

In preferred embodiments: the nucleic acid is that of SEQ ID NO:3; the nucleic acid is at least 60%, 70%, 80%, 90% or 95% homologous with the nucleic acid sequence of SEQ ID NO:3.

In preferred embodiments the encoded polypeptide has antagonistic activity, and is preferably capable of: suppressing tumor growth, e.g., in a tumor cell in which endogenous E2-BP is misexpressed; suppressing growth of papillomavirus-infected cells, e.g., HPV-infected cells; inhibiting growth of a papillomavirus-infected cell, e.g., an HPV-infected cell, e.g., a low-risk or a high-risk HPV infected cell, e.g., and HPV-16, -18, -31, or -33 infected cell, e.g., a bovine papillomavirus (BPV)-infected cell; inhibiting infection of a cell by a papillomavirus, e.g., an HPV, e.g., a high-risk HPV, e.g., and HPV-16, -18, -31, or -33, e.g. a bovine papillomavirus (BPV); inhibiting transformation of a cell by a papillomavirus, e.g., an HPV, e.g., a high-risk HPV, e.g., and HPV-16, -18, -31, or -33, e.g., a bovine papillomavirus; or inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; inhibiting the growth of, or diminishing the size of a wart.

In a preferred embodiment, the encoded E2-BP$^{SD-23}$ polypeptide differs in amino acid sequence at 1, 2, 3, 5, 10 or more residues, from the sequence in SEQ ID NO:7. The differences, however, are such that: the encoded E2-BP polypeptide exhibits an E2-BP biological activity, e.g., the encoded E2-BP$^{SD-23}$ polypeptide retains a biological activity of a naturally occurring E2-BP$^{SD-23}$, e.g., the E2-BP$^{SD-23}$ of SEQ ID NO:7.

In yet other preferred embodiments, the encoded polypeptide is a recombinant fusion protein having a first E2-BP portion and a second polypeptide portion, e.g., a second polypeptide portion having an amino acid sequence unrelated to the E2-BP$^{SD-23}$. The second polypeptide portion can be glutathione-S-transferase; a DNA binding domain; or a polymerase activating domain. In preferred embodiments the fusion protein can be used in a two-hybrid assay.

In preferred embodiments, the subject E2-BP$^{SD-23}$ nucleic acid will include a transcriptional regulatory sequence, e.g. at least one of a transcriptional promoter or transcriptional enhancer sequence, operably linked to the E2-BP$^{SD-23}$ gene sequence, e.g., to render the E2-BP$^{SD-23}$ gene sequence suitable for use as an expression vector.

In yet a further preferred embodiment, the nucleic acid which encodes an E2-BP polypeptide of the invention, hybridizes under stringent conditions to a nucleic acid probe corresponding to at least 12 consecutive nucleotides of SEQ ID NO:3; more preferably to at least 20 consecutive nucleotides of SEQ ID NO:3; more preferably to at least 40 consecutive nucleotides of SEQ ID NO:3.

Another aspect of the present invention provides a substantially pure nucleic acid having a nucleotide sequence which encodes an E2-BP$^{SD-24}$ polypeptide. In preferred embodiments: the encoded polypeptide has biological activity, e.g., it specifically binds a papillomavirus E2 protein; the encoded polypeptide has an amino acid sequence at least 60%, 80%, 90% or 95% homologous to the amino acid sequence in SEQ ID NO:8; the encoded polypeptide has an amino acid sequence essentially the same as the amino acid sequence in SEQ ID NO:8; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:8; the encoded E2-BP$^{SD-24}$ polypeptide is either, an agonist or an antagonist, of a biological activity of a naturally occurring E2-BP. For example, the encoded E2-BP$^{SD-24}$ polypeptide is an agonist or antagonist of the regulation of E2 function, e.g. of E2-mediated expression of PV oncogenes.

In preferred embodiments: the nucleic acid is that of SEQ ID NO:4; the nucleic acid is at least 60%, 70%, 80%, 90% or 95% homologous with the nucleic acid sequence of SEQ ID NO:4.

In preferred embodiments the encoded polypeptide has antagonistic activity, and is preferably capable of: suppressing tumor growth, e.g., in a tumor cell in which endogenous E2-BP is misexpressed; suppressing growth of papillomavirus-infected cells, e.g., HPV-infected cells; inhibiting growth of a papillomavirus-infected cell, e.g., an HPV-infected cell, e.g., a low-risk or a high-risk HPV infected cell, e.g., and HPV-16, -18, -31, or -33 infected cell, e.g., a bovine papillomavirus (BPV)-infected cell; inhibiting infection of a cell by a papillomavirus, e.g., an HPV, e.g., a high-risk HPV, e.g., and HPV-16, -18, -31, or -33, e.g., a bovine papillomavirus (BPV); inhibiting transformation of a cell by a papillomavirus, e.g., an HPV, e.g., a high-risk HPV, e.g., and HPV-16, -18, -31, or -33, e.g., a bovine papillomavirus; or inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; inhibiting the growth of, or diminishing the size of a wart.

In a preferred embodiment, the encoded E2-BP$^{SD-24}$ polypeptide differs in amino acid sequence at 1, 2, 3, 5, 10 or more residues, from the sequence in SEQ ID NO:8. The differences, however, are such that: the encoded E2-PB polypeptide exhibits an E2-BP biological activity, e.g., the encoded E2-BP$^{SD-24}$ polypeptide retains a biological activity of a naturally occurring E2-BP$^{SD-24}$, e.g., the E2-BP$^{SD-24}$ of SEQ ID NO:4.

In yet other preferred embodiments, the encoded polypeptide is a recombinant fusion protein having a first E2-BP portion and a second polypeptide portion, e.g., a second polypeptide portion having an amino acid sequence unrelated to the E2-BP$^{SD-24}$. The second polypeptide portion can be glutathione-S-transferase; a DNA binding domain; or a polymerase activating domain. In preferred embodiments the fusion protein can be used in a two-hybrid assay.

In preferred embodiments, the subject E2-BP$^{SD-24}$ nucleic acid will include a transcriptional regulatory sequence, e.g. at least one of a transcriptional promoter or transcriptional enhancer sequence, operably linked to the E2-BP$^{SD-24}$ gene sequence, e.g., to render the E2-BP$^{SD-24}$ gene sequence suitable for use as an expression vector.

In yet a further preferred embodiment, the nucleic acid which encodes an E2-BP polypeptide of the invention, hybridizes under stringent conditions to a nucleic acid probe corresponding to at least 12 consecutive nucleotides of SEQ ID NO:4; more preferably to at least 20 consecutive nucleotides of SEQ ID NO:4; more preferably to at least 40 consecutive nucleotides of SEQ ID NO:4.

Another aspect of the present invention provides a substantially pure nucleic acid having a nucleotide sequence which encodes an E2-BP$^{SD2-7}$ polypeptide. In preferred embodiments: the encoded polypeptide has biological activity, e.g., it specifically binds a papillomavirus E2 protein; the encoded polypeptide has an amino acid sequence at least 60%, 80%, 90% or 95% homologous to the amino acid sequence in SEQ ID NO:6; the encoded polypeptide has an amino acid sequence essentially the same as the amino acid sequence in SEQ ID NO:6; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:6; the encoded E2-BP$^{SD2-7}$ polypeptide is either, an agonist or an antagonist, of a biological activity of a naturally occurring E2-BP. For example, the encoded E2-Bp$^{SD2-7}$ polypeptide is an agonist or antagonist of the regulation of E2 function, e.g. of E2-mediated expression of PV oncogenes.

In preferred embodiments: the nucleic acid is that of SEQ ID NO:2; the nucleic acid is at least 60%, 70%, 80%, 90% or 95% homologous with the nucleic acid sequence of SEQ ID NO:2.

In preferred embodiments the encoded polypeptide has antagonistic activity, and is preferably capable of: suppressing tumor growth, e.g., in a tumor cell in which endogenous E2-BP is misexpressed; suppressing growth of papillomavirus-infected cells, e.g., HPV-infected cells; inhibiting growth of a papillomavirus-infected cell, e.g., an HPV-infected cell, e.g., a low-risk or a high-risk HPV infected cell, e.g., and HPV-16, -18, -31, or -33 infected cell, e.g., a bovine papillomavirus (BPV)-infected cell; inhibiting infection of a cell by a papillomavirus, e.g., an HPV, e.g., a high-risk HPV, e.g., and HPV-16, -18, -31, or -33, e.g., a bovine papillomavirus (BPV); inhibiting transformation of a cell by a papillomavirus, e.g., an HPV, e.g., a high-risk HPV, e.g., and HPV-16, -18, -31, or -33, e.g., a bovine papillomavirus; or inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; inhibiting the growth of, or diminishing the size of a wart.

In a preferred embodiment, the encoded E2-BP$^{SD2-7}$ polypeptide differs in amino acid sequence at 1, 2, 3, 5, 10 or more residues, from the sequence in SEQ ID NO:6. The differences, however, are such that: the encoded E2-BP polypeptide exhibits an E2-BP biological activity, e.g., the encoded E2-BP$^{SD2-7}$ polypeptide retains a biological activity of a naturally occurring E2-BP$^{SD2-7}$, e.g., the E2-BP$^{SD2-7}$ of SEQ ID NO:6.

In yet other preferred embodiments, the encoded polypeptide is a recombinant fusion protein having a first E2-BP portion and a second polypeptide portion, e.g., a second polypeptide portion having an amino acid sequence unrelated to the E2-BP$^{SD2-7}$. The second polypeptide portion can be glutathione-S-transferase; a DNA binding domain; or a polymerase activating domain. In preferred embodiments the fusion protein can be used in a two-hybrid assay.

In preferred embodiments, the subject E2-BP$^{SD2-7}$ nucleic acid will include a transcriptional regulatory sequence, e.g. at least one of a transcriptional promoter or transcriptional enhancer sequence, operably linked to the E2-BP$^{SD2-7}$ gene sequence, e.g., to render the E2-BP$^{SD2-7}$ gene sequence suitable for use as an expression vector.

In yet a further preferred embodiment, the nucleic acid which encodes an E2-BP polypeptide of the invention, hybridizes under stringent conditions to a nucleic acid probe corresponding to at least 12 consecutive nucleotides of SEQ ID NO:2; more preferably to at least 20 consecutive nucleotides of SEQ ID NO:2; more preferably to at least 40 consecutive nucleotides of SEQ ID NO:2.

The invention also provides a probe or primer which includes a substantially purified oligonucleotide. The oligonucleotide includes a region of nucleotide sequence which hybridizes under stringent conditions to at least 10 consecutive nucleotides of sense or antisense sequence of one of SEQ ID NOS: 1–4, or naturally occurring mutants thereof. In preferred embodiments, the probe or primer further includes a label group attached thereto. The label group can be, e.g., a radioisotope, a fluorescent compound, an enzyme, and/or an enzyme co-factor. Probes of the invention can be used as a part of a diagnostic test kit for identifying transformed cells, such as for measuring in a sample of cells isolated from a patient, a level of a nucleic acid encoding one of the subject E2-binding proteins; e.g. measuring the E2-BP mRNA level in a cell; e.g. determining whether the genomic E2-BP gene has been mutated or deleted. Preferably the oligonucleotide is at least 10 and less than 20, 30, 50, 100, or 150 nucleotides in length.

In another aspect, the invention features a purified preparation of cells, e.g., cells having an E2-BP transgene, or cells which misexpress an E2-BP. The cell preparation can consist of human or non human cells, e.g., rodent cells, e.g., mouse or rat cells, rabbit cells, or pig cells, having an E2-BP transgene, e.g., a cell which includes (and preferably express) a heterologous form of one of the E2-BP genes described herein, e.g. a gene derived from humans (in the case of a non-human cell), or a gene which misexpress an endogenous E2-BP gene, e.g., a cell in which expression of one or more of the subject E2-BP's is disrupted. Such a transgenic cell can serve as a model for studying.cellular disorders which are related to mutated or mis-expressed E2-BP alleles or for use in drug screening.

For example, the invention includes a method of evaluating the effect of the expression or misexpression of an E2-BP on any of: a parameter related to the viral life cycle, e.g., transcription, translation, infectivity; a parameter related to transformation, e.g., cell growth; a parameter related to immortalization, e.g., cell growth; a parameter related to unwanted cell proliferation, e.g., the formation of warts or tumors. The method includes: providing a transgenic cell having an E2-BP transgene; contacting the cell with a PV, e.g., an HPV; and evaluating the effect of the transgene on the parameter (e.g., by comparing the value of the parameter for a transgenic cell with the value for a control, e.g., a wild type cell).

In another aspect, invention features, a transgenic non-human animal, e.g., a rodent, e.g., a mouse or a rat, a rabbit, or a pig, having an E2-BP transgene, e.g., an animal which includes (and preferably express) a heterologous form of one of the E2-BP genes described herein, e.g., a gene derived from humans, or a gene which misexpress an endogenous E2-BP gene, e.g., an animal in which expression of one or more of the subject E2-BP's is disrupted. Such a transgenic animal can serve as a model for studying cellular disorders which are related to mutated or mis-expressed E2-BP alleles or for use in drug screening.

For example, the invention includes a method of evaluating the effect of the expression or misexpression of an E2-BP on any of: a parameter related to the viral life cycle, e.g., transcription, translation, infectivity; a parameter related to transformation, e.g., cell growth; a parameter related to immortalization, e.g., cell growth; a parameter related to unwanted cell proliferation, e.g., the formation of warts or tumors. The method includes: providing a transgenic animal having an E2-BP transgene; contacting the animal with a PV, e.g., an HPV; and evaluating the effect of the transgene on the parameter (e.g., by comparing the value of the parameter for a transgenic animal with the value for a control, e.g., a wild type animal).

In yet another aspect, the invention features a method for evaluating a test compound, e.g., for the ability to modulate an interaction, e.g., to inhibit an interaction of an E2-BP polypeptide with a papillomavirus E2 protein. The method includes the steps of (i) combining a viral E2 protein (or preferably a purified preparation thereof), an E2-BP(or preferably a purified preparation thereof), e.g., an E2-BP of the invention (e.g., a protein expressed from one of the clones selected from the group 42A, SD-23, SD-24 or SD2-7), and a test compound, e.g., under conditions wherein in the absence of the test compound the E2 protein and the E2-binding protein are able to interact, e.g., to form a complex; and (ii) detecting the interaction, e.g., detecting the formation (or dissolution) of a complex which includes the E2 protein and the E2-binding protein. A change, e.g., a decrease or increase, in the formation of the complex in the presence of a test compound (relative to what is seen in the absence of the test compound) is indicative of a modulation, e.g., an inhibition or promotion, of the interaction between the E2 protein and the E2-binding protein. In preferred embodiments: the E2 protein is an HPV E2 protein, e.g. from a high-risk HPV, e.g. from HPV-16, -18, -31 or -33; the E2 protein is a BPV E2 protein; the E2 protein and the E2binding protein are combined in a cell-free system and contacted with the test compound; i.e. the cell-free system is selected from a group consisting of a cell lysate and a reconstituted protein mixture; the E2-binding protein are simultaneously expressed in a cell, and the cell is contacted with the test compound, e.g. the E2-binding protein comprise an interaction trap assay (e.g., a two-hybrid assay).

In yet another aspect, the invention features a two-phase method (having an in vitro and an in vivo phase) for evaluating a test compound, e.g., for the ability to modulate, e.g., to inhibit or promote, an interaction of an E2-BP polypeptide with a papillomavirus E2 protein. The method includes: (i) combining, in vitro, a viral E2 protein (or preferably a purified preparation thereof), an E2-BP (or preferably a purified preparation thereof), e.g., an E2-BP of the invention (e.g., a protein expressed from one of the clones selected from the group 42A, SD-23, SD-24 or SD2-7), and a test compound, e.g., under conditions wherein in the absence of the test compound the E2 protein and the E2-binding protein are able to interact, e.g., form a complex; (ii) detecting an interaction, e.g., the formation (or dissolution) of a complex which includes the E2 protein and the E2-binding protein (a change, e.g., a decrease, in the interaction, e.g., the formation of the complex in the presence of a test compound (relative to what is seen in the absence of the test compound) being indicative of a modulation, e.g., an inhibition, of the interaction between the E2 protein and the E2-binding protein); (iii) determining if the test compound modulates the interaction in vitro and if so; (iv) administering the test compound to a cell or animal; and (v) evaluating the in vivo effect of the compound on an interaction, e.g., inhibition, of an E2-BP polypeptide with a papillomavirus E2 protein, e.g., by the effect on cell growth or by the effect on the expression of a PV gene or a reporter gene.

In preferred embodiments: the E2 protein is an HPV E2 protein, e.g. from a high-risk HPV, e.g. from HPV-16, -18, -31 or -33; the E2 protein is a BPV E2 protein.

In yet another aspect, the invention features a method of evaluating the ability of a compound to modulate any of: the viral life cycle, e.g., transcription, translation, infectivity; the ability of a PV to effect transformation of a cell; the ability of a PV to effect immortalization of a cell; or unwanted cell proliferation, e.g., the formation of warts or tumors. The method includes the steps of (i) combining a viral E2 protein (or preferably a purified preparation thereof), an E2-BP (or preferably a purified preparation thereof), e.g., an E2-BP of the invention (e.g., a protein expressed from one of the clones selected from the group 42A, SD-23, SD-24 or SD2-7), and a test compound, e.g., under conditions wherein in the absence of the test compound, the E2 protein and the E2-binding protein are able to interact; and (ii) detecting the interaction, e.g., the formation (or dissolution) of a complex which includes the E2 protein and the E2-binding protein. A change, e.g., a decrease, in the formation of the complex in the presence of a test compound (relative to what is seen in the absence of the test compound) is indicative of the ability to modulate one of: the viral life cycle, e.g., transcription, translation, infectivity; the ability of a PV to effect transformation of a cell; the ability of a PV to effect immortalization of a cell; or unwanted cell proliferation, e.g., the formation of warts or tumors. In preferred embodiments: the E2 protein is an HPV E2 protein, e.g. from a high-risk HPV, e.g. from HPV-16, -18, -31 or -33; the E2 protein is a BPV E2 protein; the E2 protein and the E2-binding protein are combined in a cell-free system and contacted with the test compound; i.e. the cell-free system is selected from a group consisting of a cell lysate and a reconstituted protein mixture; the E2-binding protein are simultaneously expressed in a cell, and the cell is contacted with the test compound, e.g. the E2-binding protein comprise an interaction trap assay (e.g., a two hybrid assay). Contacting cells with agents that alter the formation of one or more E2-BP/E2 complexes can inhibit pathological progression of papillomavirus infection, such as preventing or reversing the formation of warts, e.g. Plantar warts (verruca plantaris), common warts (verruca plana), Butcher's common warts, flat warts, genital warts (condyloma acuminatum), or epidermodysplasia verruciformis; as well as treating papillomavirus cells which have become, or are at risk of becoming, transformed and/or immortalized, e.g. cancerous, e.g. a laryngeal papilloma, a focal epithelial, a cervical carcinoma.

In yet another aspect, the invention features a two-phase method (having an in vitro and an in vivo phase) of evaluating the ability of a compound to modulate on any of: the viral life cycle, e.g., transcription, translation, infectivity; the ability of a PV to effect transformation of a cell; the ability of a PV to effect immortalization of a cell; or unwanted cell proliferation, e.g., the formation of warts or tumors. The method includes (i) combining, in vitro, a viral E2 protein (or preferably a purified preparation thereof), an E2-BP (or preferably a purified preparation thereof), e.g., an E2-BP of the invention (e.g. a protein expressed from one of the clones selected from the group 42A, SD-23, SD-24 or SD2-7), and a test compound, e.g., under conditions wherein in the absence of the test compound the E2protein and the E2-binding protein are able to interact; (ii) detecting the formation (or dissolution) of a complex which includes the E2 protein and the E2-binding protein and if the compound has an effect on formation or dissolution; (iii) administering the test compound to a cell or animal; and (iv) evaluating the in vivo effect of the compound on any of: the viral life cycle, e.g., transcription, translation, infectivity; the ability of a PV to effect transformation of a cell; the ability of a PV to effect immortalization of a cell; or unwanted cell proliferation, e.g., the formation of warts or tumors, e.g., by the effect on cell growth or by the effect on the expression of a PV gene.

In preferred embodiments: the E2 protein is an HPV E2 protein, e.g. from a high-risk HPV, e.g. from HPV-16, -18, -31 or -33; the E2 protein is a BPV E2 protein.

In yet another aspect, the invention features a method of evaluating the ability of an E2-BP peptide to modulate propagation of a virus including: (i) providing a cell; (ii) administering an E2-BP to the cell; and (ii) contacting the cell with a PV; and (iii) determining the effect of the E2-BP on a a parameter related to the propagation of a virus, e.g., viral replication, transcription, translation, transformation, or immortalization.

In preferred embodiments the E2-BP is: $E2\text{-}BP^{42A}$, $E2\text{-}BP^{SD-23}$, $E2BP^{SD-24}$ or $E2\text{-}BP^{SD2-7}$.

In another aspect, the invention features a method of evaluating the ability of a compound to interact with, e.g., to bind, an E2-BP, e.g., $E2\text{-}BP^{42A}$, $B2\text{-}BP^{SD-23}$, $E2\text{-}BP^{SD-24}$ or $BP^{SD2-7}$. The method includes: providing the E2-BP (preferably in purified form); contacting the E2-BP with the compound; and determining whether the compound can interact with, e.g, bind to the E2-BP. The method can be used to identify compounds which interrupt the interaction of E2 with an E2-BP. The ability of the compound to interact with the E2-BP can be evaluated in a variety of ways, e.g., by determining the ability of the compound to bind to immobilized E2-BP, or by determining the ability of the compound to prevent or disrupt binding of a ligand, e.g., and anti E2-BP antibody or E2, to the E2-BP.

In preferred embodiments, E2-BP proteins are thought to interact with cellular and/or viral components, thus compounds which interact with E2-BP's maybe useful for studying or modulating, e.g., inhibiting or promoting, viral related processes, e.g., compounds maybe useful for studying or modulating unwanted cell proliferation; compounds maybe useful for studying or treating the formation of warts or tumors, or for studying the effect on cell growth, or the effect on the expression of a PV gene.

In another aspect, the invention features, a method of determining the presence of, or evaluating the stage of an E2-BP related disorder in a subject mammal, e.g., a primate, e.g., a human. The method includes: evaluating expression of an E2-BP in the subject, e.g., by obtaining a sample from the subject, e.g., a blood sample, and evaluating that sample for the expression of an E2-BP, e.g., an $E2\text{-}BP^{42A}$, an $E2\text{-}BP^{SD-23}$, an $E2\text{-}BP^{SD-24}$ or an $BP^{SD2-7}$. Non-wild type expression of E2-BP is indicative of an E2-BP related disorder.

Another aspect of the present invention provides a method of determining if a subject mammal, e.g., a primate, e.g., a human, is at risk for a disorder characterized by unwanted cell proliferation. The method includes detecting, in a tissue of the subject, the presence or absence of a genetic lesion characterized by at least one of: (i) a mutation of a gene encoding a protein represented by one of SEQ ID NOS:5–8, or a homolog thereof; or (ii) the mis-expression of a gene encoding a protein represented by one of SEQ ID NOS:5–8 or a homolog thereof. In preferred embodiments: detecting the genetic lesion includes ascertaining the existence of at least one of: a deletion of one or more nucleotides from the E2-BP gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include: (i) providing a probe/primer including an oligonucleotide containing a region of nucleotide sequence which hybridizes to a sense or antisense sequence of one of SEQ ID NOS: 1–4, or naturally occurring mutants thereof or 5' or 3' flanking sequences naturally associated with the E2-BP gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the E2-BP gene and, optionally, of the flanking nucleic acid sequences; e.g. wherein detecting the lesion comprises utilizing the probe/primer in a polymerase chain reaction (PCR); e.g. wherein detecting said lesion comprises utilizing the probe/primer in a ligation chain reaction (LCR). In alternate embodiments, the level of said protein is detected in an immunoassay using an antibody which is specifically immunoreactive with, e.g., a protein represented by one of SEQ ID NOS:5–8.

The invention also provides a method for treating a subject mammal, e.g., a primate, e.g., a human, having unwanted cell growth characterized by a loss of wild-type function of one or more of the subject E2-binding proteins. The method includes: administering a therapeutically effective amount of an agent able to inhibit the interaction of the E2-binding protein with other cellular or viral proteins. In one embodiment, the method comprises administering a nucleic acid construct encoding a polypeptides represented in one of SEQ ID NOS:5–8, under conditions wherein the construct is incorporated by cells deficient in that E2-binding protein, and under conditions wherein the recombinant gene is expressed, e.g., by gene therapy techniques.

In another aspect, the invention features, a mutant E2 polypeptide, preferably a substantially pure preparation of a mutant E2 polypeptide, or a recombinant mutant E2polypeptide, which can bind E2 responsive elements in the PV genome, but which is defective in the activation of the transcription of genes which are under transcriptional control of E2. In preferred embodiments: the mutant E2 results in a reduction of at least 25%, more preferably 50%, and even more preferably 75% or 90% of the activation of a PV ordinarily under the control of an E2 polypeptide. In preferred embodiments: the mutation is a point mutation; the mutation is in the first 10, 20, 50, 100, 150, or 250 amino acids of a naturally occurring E2; the E2 mutant has an amino acid change, preferably a non conservative amino acid change, at a residue between amino acid residues 15 and 208 of E2, inclusive; the mutation is at any of the following amino acid residues: Q 15 H, D 24 A, K 25 E, E 39 G, A 46 E, F 87 S, W 92 R, W 99 C, P 106 S, N 127 Y, Y 138 H,W 145 R, or R 208 G;the mutant E2 polypeptide is other than a truncation mutant, e.g., other than a truncation in which the first 10, 20, 50, or 100 N-terminal amino acids of a naturally occurring E2 are deleted; the mutant E2 polypeptide is encoded by nucleic acid which can hybridize under stringent conditions to nucleic acid which encodes first 10, 20, 50, or 100 amino acids of a naturally occurring E2.

In preferred embodiments the mutant E2 polypeptide is a deletion mutant, wherein, preferably less than 10 nucleotides, more preferably less than 5 nucleotides, even more preferably less than 3 nucleotides of a naturally occurring E2 are deleted. In preferred embodiments the polypeptide has an amino acid sequence at least 60%, 80%, 90% or 95% homologous to the amino acid sequence of a naturally occurring E2 polypeptide; the polypeptide is at least 5, 10, 20, 50, 100, or 150 amino acids in length; the polypeptide includes at least 5, preferably at least 10, more preferably at least 20, more preferably at least 50, 100, or 150 contiguous amino acids from sequence of the naturally occurring E2 polypeptide; the mutant E2 polypeptide disrupts the biological activity of a naturally occurring E2 polypeptide. For example, the mutant E2 polypeptide can exert an antiviral effect by interfering with E2-mediated transcription of PV oncogenes.

In preferred embodiments: the mutant E2 polypeptide is encoded by the nucleic acid of a wild type E2, or by a nucleic acid having at least 60%, 70%, 80%, 90% or 95% homology with the nucleic acid of the wild type E2.

In preferred embodiments the mutant E2 polypeptide competes with wild type E2 for binding to E2 responsive elements in the PV genome, and is capable of: suppressing tumor growth, e.g., in a tumor cell in which endogenous E2 is expressed; suppressing growth of papillomavirus-infected cells, e.g., HPV-infected cells; inhibiting growth of a papillomavirus infected cell, e.g., an HPV-infected cell, e.g., a high-risk HPV-infected cell, e.g., and HPV-16, -18, -31 infected cell, e.g., a bovine papillomavirus (BPV); inhibiting infection of a cell by a papillomavirus, e.g., an HPV, e.g., a high-risk HPV, e.g., and HPV-16, -18, -31, or 33, e.g., a bovine papillomavirus (BPV); inhibiting transformation of a cell by a papillomavirus, e.g., an HPV, e.g., ahigh-risk HPV, e.g., and HPV-16, -18, -31, or 33, e.g., ahuman cell, by a papillomavirus, e.g., an HPV, e.g., a high-risk HPV, e.g., and HPV-16, -18, -31, or 33, e.g., a bovine papillomavirus; inhibiting the growth of, or diminishing the size of a wart.

The invention includes an immunogen which includes a mutant E2 polypeptide in an immunogenic preparation, the immunogen being capable of eliciting an immune response specific for said mutant E2 polypeptide, e.g., a humoral response, an antibody response, or a cellular response. In preferred embodiments, the immunogen comprising an antigenic determinant, e.g., a unique determinant, from a protein represented by mutant E2 polypeptide.

The present invention also includes an antibody preparation specifically reactive with an epitope of a mutant E2 immunogen, or generally of a mutant E2 polypeptide. In a preferred embodiment the antibody does not cross react with a wild type E2 polypeptide or with the E2 truncation polypeptide referred to herein.

In another aspect, the invention features, a substantially pure nucleic acid, or a recombinant nucleic acid, which encodes a mutant E2 polypeptide which can bind E2 responsive elements in the PV genome, but which is defective in the activation of the transcription of genes which are under transcriptional control of E2. In preferred embodiments: the mutant E2 results in a reduction of at least 25%, more preferably 50%, and even more preferably 75% or 90% of the activation of a PV ordinarily under the control of an E2 polypeptide. In preferred embodiments: the mutation is a point mutation; the mutation is in the first 10, 20, 50, 100, 150, or 250 amino acids of a naturally occurring E2; the E2 mutant has an amino acid change, preferably a non conservative amino acid change, at a residue between amino acid residues 15 and 208 of E2, inclusive; the mutation is at any of the following amino acid residues: Q 15 H, D 24 A, K 25 E, E 39 G, A 46 E, F 87 S, W 92 R, W 99 C, P 106 S, N 127 Y, Y 138 H, W 145 R, or R 208 G; the mutant E2 encoded polypeptide is other than a truncation mutant, e.g., other than a truncation in which the first 10, 20, 50, or 100 N terminal amino acids of a naturally occurring E2are deleted; the mutant E2 encoded polypeptide is encoded by nucleic acid which can hybridize under stringent conditions to nucleic acid which encodes first 10, 20, 50, or 100 amino acids of a naturally occurring E2.

In preferred embodiments the mutant E2 encoded polypeptide is a deletion mutant, wherein, preferably less than 10 nucleotides, more preferably less than 5 nucleotides, even more preferably less than 3 nucleotides of a naturally occurring E2 are deleted. In preferred embodiments the encoded polypeptide has an amino acid sequence at least 60%, 80%, 90% or 95% homologous to the amino acid sequence of a naturally occurring E2 polypeptide; the encoded polypeptide is at least 5, 10, 20, 50, 100, or 150 amino acids in length; the encoded polypeptide includes at least 5, preferably at least 10, more preferably at least 20, more preferably at least 50, 100, or 150 contiguous amino acids from sequence of the naturally occurring E2 polypeptide; the mutant E2 encoded polypeptide disrupts the biological activity of a naturally occurring E2 polypeptide. For example, the mutant E2 polypeptide can exert an antiviral effect by interfering with E2-mediated transcription of PV oncogenes.

In preferred embodiments: the nucleic acid is that of naturally occurring E2; the nucleic acid is at least 60%, 70%, 80%, 90% or 95% homologous with the nucleic acid sequence of naturally occurring E2.

In preferred embodiments the encoded polypeptide competes with wild type E2 for binding to E2responsive elements in the PV genome, and is preferably capable of: suppressing tumor growth, e.g., in a tumor cell in which endogenous E2 is expressed; suppressing growth of papillomavirus-infected cells, e.g., HPV-infected cells; inhibiting growth of a papillomavirus-infected cell, e.g., an HPV-infected cell, e.g., a high-risk HPV infected cell, e.g., and HPV-16, -18, -31, or -33 infected cell, e.g., a bovine papillomavirus (BPV)-infected cell; inhibiting infection of a cell by a papillomavirus, e.g., an HPV, e.g., a high-risk HPV, e.g., and HPV-16, -18, -31, or -33, e.g., a bovine papillomavirus (BPV); inhibiting transformation of a cell by a papillomavirus, e.g., an HPV, e.g., a high-risk HPV, e.g., and HPV-16, -18, -31, or -33, e.g., a bovine papillomavirus; or inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; inhibiting the growth of, or diminishing the size of a wart.

In preferred embodiments, the subject mutant E2 nucleic acid will include a transcriptional regulatory sequence, e.g., at least one of a transcriptional promoter or transcriptional enhancer sequence, operably linked to the mutant E2 gene sequence, e.g., to render the mutant E2 gene sequence suitable for use as an expression vector.

The invention also provides a method for treating a subject mammal, e.g., a primate, e.g., a human, having a disorder characterized by the presence of PV, e.g., a disorder characterized by unwanted cell proliferation; or by the interaction of an E2 protein with the PV genome. The method includes: administering a therapeutically effective amount of the mutant E2 polypeptide, or a fragment thereof, to a subject mammal, e.g., a primate, e.g., a human. In one embodiment, the method comprises administering a nucleic acid construct encoding a mutant E2 polypeptide, under conditions wherein the construct is incorporated by cells in which PV genes are under transcriptional control of a wild type E2, and under conditions wherein the recombinant gene is expressed, e.g. by gene therapy techniques.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular CloningA Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DESCRIPTION OF THE DRAWING

FIG. 2 is a schematic diagram illustrating the interaction of E2 and E2 variants with 42A as defined by in vivo and in vitro binding assays.

DETAILED DESCRIPTION OF THE INVENTION

Overview: The Papillomaviruses and E2-BP's

Figure 1:
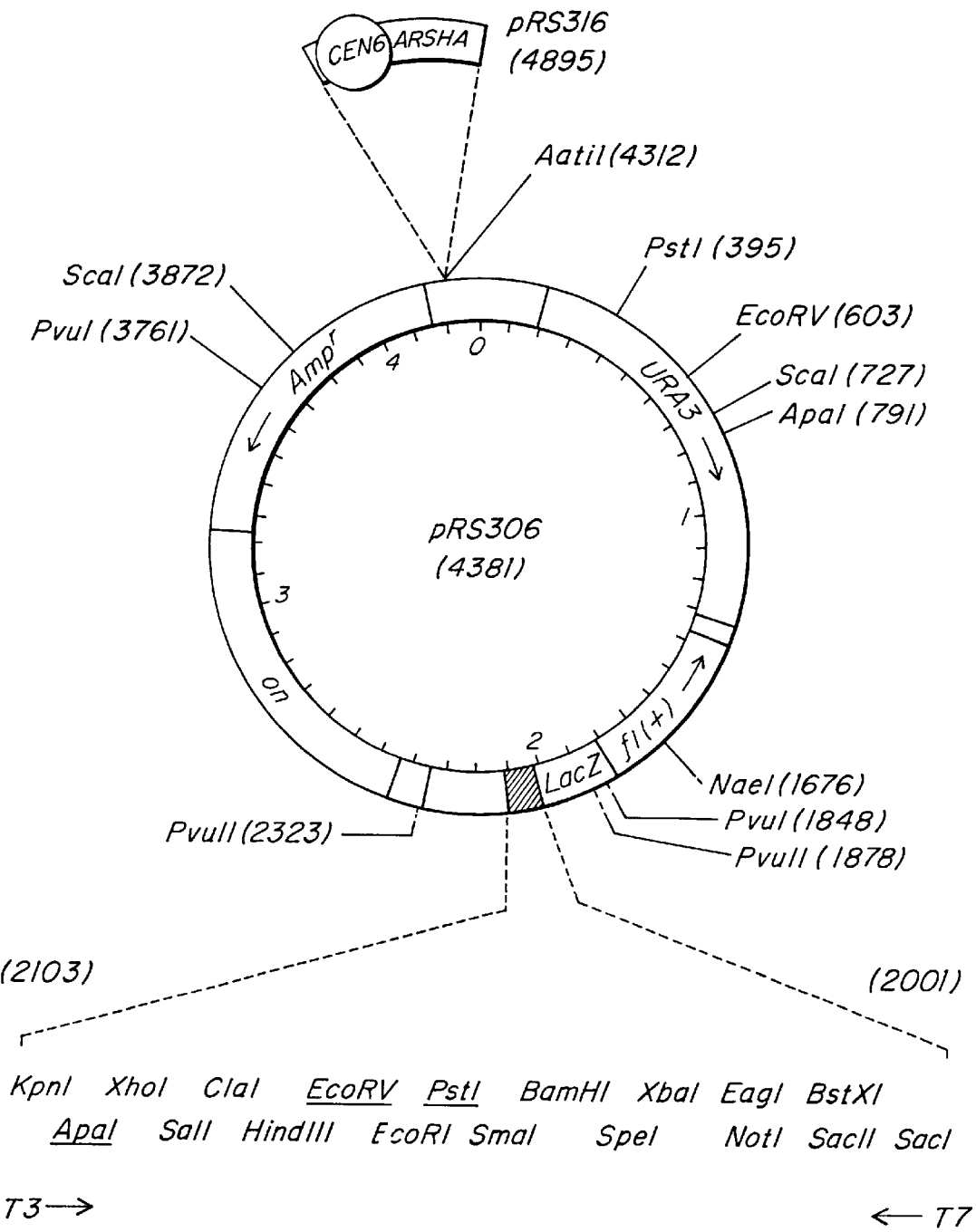
FIG. 1 is the general map of the pEJA plasmid used to construct the VP 16/cDNA fusion gene for expression in a two hybrid assay.

The papillomaviruses (PV) are infectious agents that can cause benign epithelial tumors, or warts, in their natural hosts. Infection with specific human papillomaviruses (HPV) is also associated with human epithelial malignancies, including malignancies of the uterine cervix, genitalia, skin and less frequently, other sites.

The analysis of the temporal expression of mRNAs and the nucleotide sequence of human and animal papillomavirus (PV) genomes has revealed overall structural similarities in their genetic organization. There are at least seven open reading frames (ORFs) in all PVs, and differential RNA splicing provides the capability to produce several additional proteins. The genes that are required for viral replication are typically designated with the prefix "E" (for "early"), being expressed before the "L" or "late" genes. The products of the papillomavirus E2 open reading frame play a key role in the regulation of the viral cycle, affecting both transcription and replication. For instance, E2 proteins can activate or repress viral promoters apparently by several distinct mechanisms, though binding to conserved DNA motifs in the viral genome is a common requirement. The E2 protein appears to provide both positive and negative feedback loops for viral gene expression, and appears to be part of a necessary mechanism for achieving long-term persistence of infection.

Although amino acid sequence homology among E2 proteins of various papillomaviruses is low (typically about 35 percent), the E2 proteins share conserved motifs that constitute unique structural domains having distinct functions. In particular, the C-terminal domain of the E2 protein is responsible for recognition of E2 binding sites on viral DNA. The N-terminal domain of the E2 protein is responsible for transcriptional activation following binding of homodimers of the E2 protein to viral DNA. However, the large size of the N-terminal transactivation domain has led us to predict that this domain defines multiple interactions with other cellular proteins, e.g. transcriptional factors, the interplay with which is a prerequisite for physiological responses, persistence, and cellular specificity of papillomavirus infections. In work described herein, a two hybrid assay (an example of a two hybrid assay can be found in U.S. patent application Ser. No. 5,283,173) was used to identify human cellular proteins which interact with the viral E2 protein and which are candidate proteins participation in PV infectivity and/or transformation.

As described in the examples below, the two hybrid system used to screen cDNA libraries for E2 interactors includes an E2 responsive β-galactosidase (lac Z) reporter construct and an expression construct encoding a transactivation defective E2 protein. The transactivation defective E2 mutants used were derived by screening a library of mutants containing point mutations in the N-terminal portion of the protein. The E2 mutants isolated retained DNA binding activity despite an inability to activate transcription. Activation of the E2 responsive reporter occurred only when a protein containing a finctional transcriptional activation domain interacted with the defective E2 protein as a complex bound to the E2 responsive elements in the reporter gene. A yeast strain expressing the transcriptionally defective E2 and harboring the E2-responsive reporter construct was transformed with a library of yeast shuttle vector plasmid in which randomly primed HeLa cell cDNA was inserted C-terminal to the strong VP 16 transcription activation domain. Interaction of VP 16/cDNA fusion proteins with the defective E2 protein recruits the VP 16 transcriptional activation domain to the E2 binding sites and activates expression of the lacZ gene.

This assay was used to isolate a number of human genes which encode proteins that specifically interact with E2. Embodiments of the invention, as described below, derive, in part, from the discovery that in addition to other viral proteins such as E1, the papillomavirus protein E2 can also associate with several cellular proteins (hereinafter termed "cellular E2 binding protein" or "E2-BPs"), which association appears to be important to the pathogenesis of papillomavirus infection and papillomavirus-mediated disease states. For example, association of an E2-binding protein with E2 could be important for regulating expression of the viral oncogenes, e.g. E5, E6 or E7, or for providing a mechanism to ensure specificity of infection based on cell-type (e.g. epithelial) and stage of differentiation of infected tissue. Certain of the E2-binding proteins may also function in the regulation of E2 mediated replication of the viral genome. Consequently, the interaction of E2 with one or more E2-binding proteins may be significant in the modulation of cellular homeostasis of infection and/or neoplastic transformation. Thus, embodiments of the invention provide diagnostic and therapeutic assays and reagents for detecting and treating papillomavirusinfected cells.

For example, E2-BP's of the invention can be used as the basis of assays to identify agents which alter, e.g. decrease, the ability of a particular E2-binding protein to bind a papillomavirus E2 protein and thereby, through modulation, e.g., inhibition, of E2-BP/E2 complexes, modulate, e.g., inhibit papillomavirus infection, transformation and/or immortalization. Such agents can be of use therapeutically to prevent E2-BP/E2 complexes in cells infected by, for example, human papillomaviruses, e.g. HPV-1, HPV-2, HPV-3, HPV-4, HPV-5, HPV-6, HPV-7, HPV-8, HPV-9, HPV-10, HPV-11, HPV-12, HPV-14, HPV-13, HPV-15, HPV-16, HPV-17 or HPV-18, particularly high-risk HPVs, such as HPV-16, HPV-18, HPV-31 and HPV-33. In similar fashion, agents can be identified which inhibit formation of E2-BP/E2 complexes in other PVs, such as bovine papillomaviruses (BPVs), e.g. BPV-1, or cottontail rabbit papillomaviruses (CRPVs). Contacting cells with agents that alter the formation of one or more E2-BP/E2 complexes can inhibit pathological progression of papillomavirus infection, such as preventing or reversing the formation of warts, e.g. Plantar warts (verruca plantaris), common warts (verruca plana), Butcher's common warts, flat warts, genital warts (condyloma acuminaturn), or epidermodysplasia verruciformis; as well as treating papillomavirus cells which have become, or are at risk of becoming, transformed and/or immortalized, e.g. cancerous, e.g. a laryngeal papilloma, a focal epithelial, a cervical carcinoma.

As used herein, the term "gene" or "recombinant gene" refers to a nucleic acid including an open reading frame encoding an E2-binding polypeptide, including both exon and (optionally) intron sequences. Exemplary recombinant genes encoding the subject E2 binding proteins are represented by any one of SEQ ID NOS:1–4. Moreover, recombinant genes encoding each of the subject E2-binding proteins can be isolated from ATCC deposit No:75915, as described below. The term "intron" refers to a DNA sequence present in a given E2-BP gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of the E2-binding protein of the present invention or where antisense expression occurs from the transferred gene, the expression of a naturally-occurring form of the E2-binding protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto. "Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant E2-BP gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the E2-binding protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a epithelial lineage, e.g. cervical squamous cells. In the illustrative embodiment of epithelial-specific promoters, gene constructs can be used as a part of gene therapy to deliver, for example, an E2-BP antagonist in order to modulate levels of E2/E2-BP complexes comprising one of the subject E2-binding proteins in papillomavirus-mediated disorders, e.g. papillomas, or to direct expression of an antisense construct of one of the subject E2-binding proteins in only epithelial tissue. The term also covers so-called "leaky" promoters, which regulate expression of a selected DNA primarily in one tissue, but cause expression in other tissues as well.

A purified preparation of cells refers to, in the case of plant or animal cells, an in vitro preparation of cells and not an entire intact plant or animal. In the case of cultured cells or microbial cell, it consists of a preparation of at least 10% or more preferably 50% of the subject cells.

As used herein, a "transgenic animal" is any animal, preferably a non-human mammal, e.g. a rat, a mouse or pig, in which one or more of the cells of the animal includes a transgene. The transgene can be introduced into a cell, directly or indirectly by introduction into a precursor of the cell, by way of deliberate genetic manipulation, such as by microinjection or by infection with a recombinant virus. This transgene can be integrated within a chromosome, or can be extrachromosomally replicating DNA. In transgenic animals described herein, the transgene, e.g., causes cells to express a recombinant form of one or more of the subject E2-binding proteins, or alternatively, disrupts expression of one or more of the naturally-occurring forms of the E2-BP genes.

As used herein, the term "transgene" means a nucleic acid sequence (encoding, e.g., one or more E2-BP's), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

Genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an E2-binding protein" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity. "Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of an acid sequence encoding one of the subject E2-binding proteins with an amino acid sequence defining a domain foreign to and not substantially homologous with any domain of the subject E2-BP. A chimeric protein may present a foreign domain which is found (albeit in a different protein) in an organism which also expresses the first protein, or it may be an "interspecies", "intergenic", etc. fusion of protein structures expressed by different kinds of organisms.

The term "evolutionarily related to", with respect to nucleic acid sequences encoding E2-binding protein, refers to nucleic acid sequences which have arisen naturally in an organism, including naturally occurring mutants. The term also refers to nucleic acid sequences which, while derived from a naturally occurring E2-BP, have been altered by mutagenesis, as for example, combinatorial mutagenesis described below, yet still encode polypeptides which have at least one activity of an E2-binding protein. Such evolutionarily derived E2-binding proteins preferred by the present invention are at least 60% homologous, more preferably 70% homologous and most preferably 80% homologous with an amino acid sequence shown in either SEQ ID NO:5, SEQ ID NO:6, SEQ ID NO:7, or SEQ ID NO:8. Polypeptides having at least about 90%, more preferably at least about 95%, and most preferably at least about 98–99% homology with a sequence shown in any of SEQ ID NOS:5–8 are also within the scope of the invention.

As described herein, one aspect of the invention features an isolated (or recombinant) nucleic acid which includes a nucleotide sequence encoding one of the subject E2-binding proteins, and/or equivalents of such nucleic acids. The term nucleic acid as used herein can include fragments and equivalents. The term equivalent refers to nucleotide sequences encoding finctionally equivalent E2-binding proteins or finctionally equivalent peptides which, for example, retain the ability to bind to E2. Equivalent nucleotide sequences will include sequences that differ by one or more nucleotide substitutions, additions or deletions, such as allelic variants, and will, therefore, include sequences that differ from the nucleotide sequence of E2-binding proteins shown in any of SEQ ID NOS: 1–4 due to the degeneracy of the genetic code. Equivalents will also include nucleotide sequences that hybridize under stringent conditions (i.e., equivalent to about 20°–27° C. below the melting temperature (T'") of the DNA duplex formed in about 1M salt) to the nucleotide sequence of E2-binding proteins represented in SEQ ID NOS: 1–4, or to the nucleotide sequence of an E2-binding protein from the pRS306-E2BP library (ATCC accession No:75915). In one embodiment, equivalents will further include nucleic acid sequences derived from and evolutionarily related to, a nucleotide sequences shown in any of SEQ ID NOS: 1–4.

The terms "isolated" or "substantially pure" as used herein with respect to nucleic acids, such as DNA or RNA, refers to molecules separated from other DNAs, or RNAs, respectively, that are present in the natural source of the macromolecule. An isolated or substantially pure nucleic acid protein preferably includes no more than 10 kilobases (kb) of nucleic acid sequence which naturally immediately flanks that sequence in genomic DNA, more preferably no more than 5 kb of such naturally occurring flanking sequences, and most preferably less than 1.5 kb of such naturally occurring flanking sequence. The term isolated or substantially pure as used herein also refers to a nucleic acid that is substantially free of cellular material, viral material, or culture medium when produced by recombinant DNA techniques, or chemical precursors or other chemicals when chemically synthesized. An "isolated or substantially pure nucleic acid" is meant to include nucleic acid fragments which are not naturally occurring as fragments and would not be found in the natural state.

In one embodiment, the nucleic acid is a cDNA encoding a peptide having at least one activity of a subject E2-binding protein. Preferably, the nucleic acid is a cDNA molecule comprising at least a portion of the nucleotide sequence represented in one of SEQ ID NOS: 1–4. A preferred portion of these cDNA molecules includes the coding region of the gene.

It may be advantageous to provide homologs of the subject E2-binding proteins which function in a limited capacity as one of either an E2-BP agonists or an E2-BP antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of an E2-binding proteins biological activities. For instance, E2-BP homologs can be generated, as described below, which interfere with the function of the viral E2 protein but which do not substantially interfere with the normal cellular function of the wild-type E2-binding protein.

The terms protein, peptide, and polypeptide are used interchangeably herein.

Homologs of the subject E2-binding proteins can be generated by mutagenesis, such as by discrete point mutation(s), or by truncation of a nucleic acid encoding a naturally occurring form of the protein. For instance, mutation can give rise to homologs which retain substantially the same, or merely a subset, of the biological activity of the E2-BP from which it was derived. Alternatively, antagonistic forms of the protein can be generated which are able to inhibit the fuiction of the naturally occurring form of the protein, such as by competitively binding to E2.

A protein has E2-BP biological activity if it has one or more of the following properties: the ability to modulate gene expression, e.g., expression of a PV gene, or replication, e.g., of a PV genome; the ability to modulate the efficacy of papillomavirus infection, e.g., human papillomaviruses, e.g., infection by HPV-16, HPV-18, HPV-31 or HPV-33; the ability to affect the efficacy of cell transformation, e.g., PV-mediated transformation, e.g., PV-mediated transformation, e.g., high risk HPV-mediated transformation; the ability to affect the efficacy of cellular immortalization, e.g., PV-mediated transformation, e.g., HPV-mediated transformation, e.g., high risk HPV-mediated immortalization; or the ability to bind a PV E2 protein, e.g., an HPV E2 protein, e.g., a high risk HPV E2 protein. A protein also has biological activity if it is a specific agonist or antagonist of one of the above recited properties.

Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. The degree of homology between sequences is a function of the number of matching or homologous positions shared by the sequences.

Some of the nucleotide sequences shown in the appended sequence listing encode portions of the E2-binding proteins. Therefore, in a further embodiment of the invention, the recombinant E2-BP genes can include, in addition to nucleotides encoding the amino acid sequences shown in SEQ ID NOS:1–4, additional nucleotide sequences which encode amino acids at the C-terminus and N-terminus of each protein. For instance, a recombinant E2-BP gene can include nucleotide sequences of a PCR fragment generated by amplifying one of the coding sequences for one of the E2-BP clones of ATCC deposit No:75915 using sets of primers derived from Table 1 below.

Another aspect of the invention provides a nucleic acid which hybridizes under high or low stringency conditions to a nucleic acid which encodes a peptide having all or a portion of an amino acid sequence shown in SEQ ID NO:5, SEQ ID NO:6, SEQ ID NO:7 or SEQ ID NO:8. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequence shown any of SEQ ID NOS: 1–4 due to degeneracy in the genetic code are also within the scope of the invention. Such nucleic acids encode finctionally equivalent peptides (i.e., a peptide having a biological activity of an E2-binding protein) but differ in sequence from the sequence shown in said sequence listings due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the E2-binding protein. However, it is expected that DNA sequence polymorphisms that do lead to changes in the amino acid sequences of the subject E2-binding proteins will exist among vertebrates. One skilled in the art will appreciate that these variations in one or more nucleotides (up to e.g., about 3–5% of the nucleotides) of the nucleic acids encoding polypeptides having an activity of an E2-binding protein may exist among individuals of a given species due to natural allelic variation. Any and all such nucleotide variations and resulting amino acid polymorphisms are within the scope of this invention.

Fragments of the nucleic acids encoding an active portion of the presently claimed E2-binding proteins are also within the scope of the invention. As used herein, a fragment of the nucleic acid encoding the active portion of an E2-binding protein refers to a nucleic acid having fewer nucleotides than the nucleotide sequence encoding the entire amino acid sequence of an E2-binding protein but which nevertheless encodes a peptide having an E2BP biological activity, e.g. the fragment retains the ability to bind to E2. Nucleic acid fragments within the scope of the present invention include those capable of hybridizing under high or low stringency conditions with nucleic acids from other species for use in screening protocols to detect E2-BP homologs, as well as those capable of hybridizing with nucleic acids from human specimens for use in detecting the presence of a nucleic acid encoding one of the subject E2-BPs, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject E2-binding proteins.

As indicated by the examples set out below, a nucleic acid encoding a peptide having an activity of an E2-binding protein may be obtained from MRNA present in eukaryotic cells.

It should also be possible to obtain nucleic acids encoding E2-binding proteins of the present invention from genomic DNA obtained from both adults and embryos. For example, a gene encoding an E2-binding protein can be cloned from either a cDNA or a genomic library in accordance with protocols herein described, as well as those known to persons skilled in the art. A cDNA encoding one of the subject E2-binding proteins can be obtained by isolating total mRNA from a cell, e.g. a mammalian cell, e.g. a human cell, including tumor cells. Double stranded cDNAs can then be prepared from the total mRNA, and subsequently inserted into a suitable plasmid or bacteriophage vector using techniques known to those skilled in the art. The gene encoding the E2-binding protein can also be cloned using established polymerase chain reaction techniques in accordance with the nucleotide sequence information provided by the invention. The nucleic acid of the invention can be DNA or RNA. A preferred nucleic acid is a cDNA represented by the sequence shown in SEQ ID NO:1. Another nucleic acid is a cDNA represented by the sequence shown in SEQ ID NO: 2. Other preferred nucleic acids include cDNA molecules represented by the sequences shown in one of SEQ ID NOS:3–4. A preferred nucleic acid is a cDNA derived from the pRS306-E2BP library (ATCC deposit No:75915).

This invention also provides expression vectors containing a nucleic acid encoding a peptide having an activity of an E2-binding protein, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of an E2-binding protein. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the E2-binding proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast alpha -mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. The vector's copy number, the ability to control that copy number and the expression of any other proteins encoded by the vector, such as antibiotic markers, should also be considered. In one embodiment, the expression vector includes a recombinant gene encoding a peptide having an activity of a subject E2-binding protein, or alternatively, encoding a peptide which is an antagonistic form of the subject E2-binding protein. Such expression vectors can be used to transfect cells and thereby produce proteins or peptides, including fusion proteins or peptides, encoded by nucleic acids as described herein.

GENE THERAPY

The gene constructs of the invention can also be used as a part of a gene therapy protocol to deliver nucleic acids encoding either an agonistic or antagonistic form of one of the E2-binding proteins. Thus, another aspect of the invention features expression vectors for in vivo transfection and expression of an E2-binding protein in particular cell types so as to reconstitute the function of, or alternatively, abrogate the function of one of the subject E2-binding proteins in a cell in which that E2-BP is misexpressed, or to deliver a form of the protein which inhibits PV-infection by interfering with the biological function of E2. Expression constructs of the subject E2-binding proteins, and mutants thereof, may be administered in any biologically effective carrier, e.g. any formulation or composition capable of effectively delivering the E2-BP gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or $CaPO_4$ precipitation carried out in vivo. Because transduction of appropriate target cells represents the critical first step in gene therapy, choice of the particular gene delivery system will depend on such factors as the phenotype of the intended target and the route of administration, e.g., locally or systemically. Furthermore, it will be recognized that the particular gene construct provided for in vivo transduction of E2-BP expression may also be useful for in vitro transduction of cells, such as for use in the diagnostic assays described above.

A preferred approach for in vivo introduction of nucleic acid into a cell is by use of a viral vector containing nucleic acid, e.g., a cDNA, encoding the E2-binding protein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψcre, ψ2 and ψAm. Retroviruses have been used to introduce a variety of genes into many different cell types, including epithelial cells, in vitro and/or in vivo (see for example Eglitis, et al. (1985) Science 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject E2-BP gene, it is important to note that a prerequisite for the successful infection of target cells by most retroviruses, and therefore of stable introduction of the recombinant E2-BP gene, is that the target cells must be dividing. With certain exceptions, such as lymphatic cancers, such a requirement will not be a hindrance to use of retroviral vectors. In fact, where gene therapy constructs of the present invention, such as antagonistic forms of E2-BP$^{424}$, are intended to be delivered to papillomavirus-transformed cells, such limitation on infection can be beneficial in that the tissue (e.g., nontransformed cells) surrounding the target cells do not likely undergo as extensive cell division and is therefore somewhat refractory to infection with retroviral vectors.

It is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, can also be used to convert an ecotropic vector in to an amphotropic vector.

The use of retroviral gene delivery can be further enhanced by the use of tissue- or cell-specific transcriptional regulatory sequences which control expression of the E2-BP gene of the retroviral vector.

Another viral gene delivery system useful in the present invention used adenovirusderived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host 5 genome (e.g., retroviral DNA). The carrying capacity of the adenoviral genome for foreign DNA is large (up to 8 kilobases) relative to other gene delivery vectors (Berkner et al. cited supra; Haj-Ahmand and Graham (1986) *J. ViroL* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp.

109–127). Expression of the inserted E2-BP gene can be under control of, for example, the E1A promoter, the major late promoter (MLP) and associated leader sequences, the E3 promoter, or exogenously added promoter sequences.

Another viral vector system useful for delivery of the subject E2-BP gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and ImmunoL* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *a Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *MoL Cell. Biol.* 4:2072–2081; Wondisford et al. (1988) Mol. EndocrinoL 2:32–39; Tratschin et al. (1984) *J. Virol.* 51:611–619; and Flotte et al. (1993) *J. BioL Chem.* 268:3781–3790).

In addition to viral transfer methods, such as those illustrated above, non-viral methods can also be employed to cause expression of an E2-binding protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject E2-BP gene by the targeted cell. Exemplary gene delivery systems of this type include liposomal derived systems, poly-lysine conjugates, and artificial viral envelopes.

In a representative embodiment, a gene encoding one of the subject E2-binding proteins can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A43075). For example, lipofection of papilloma-virus infected epithelial cells can be carried out using liposomes tagged with monoclonal antibodies against, for example, squamous cells.

In clinical settings, the gene delivery systems for the therapeutic E2-BP gene can be introduced into a patient by methods, known to those skilled in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054–3057). To illustrate, an antagonistic form of one of the subject E2-binding proteins, such as the fragment of the 42A clone described in the examples below, can be delivered in a gene therapy construct to PV-infected squamous cells by electroporation using techniques described, for example, by Dev et al. ((1994) *Cancer Treat Rev* 20:105–115.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Antisense Therapy

Another aspect of the invention relates to the use of the isolated nucleic acid in "antisense" therapy. As used herein, "antisense" therapy refers to administration or in situ generation of oligonucleotides or their derivatives which specifically hybridizes (e.g. binds) under cellular conditions, with the cellular mRNA and/or genomic DNA encoding one of an E2-binding proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular MRNA which encodes an E2-binding protein. Alternatively, the antisense construct is an oligonucleotide probe which is generated ex vivo and which, when introduced into the cell causes inhibition of expression by hybridizing with the mRNA and/or genomic sequences of an E2-BP gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

The compounds can be administered orally, or by transmucosal or transdermal means. For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as known in the art.

In addition to use in therapy, the oligomers of the invention may be used as diagnostic reagents to detect the presence or absence of the target DNA or RNA sequences to which they specifically bind. Such diagnostic tests are described in further detail herein.

The antisense constructs of the present invention, by antagonizing the normal biological activity of E2-BP, can be used in the manipulation of tissue, both in vivo and in ex vivo tissue cultures.

Transgenic Animals

The invention includes transgenic animals which include cells (of that animal) which contain an E2-BP transgene and which preferably (though optionally) express (or misexpress) an endogenous or exogenous E2-binding protein in one or more cells in the animal. The E2-BP transgene can encode the wild-type form of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. In the present invention, such mosaic expression of the subject E2-BP polypeptide can provide a means to assess the effects of, for example, lack of E2-BP expression which might have an affect on transcriptional pattern of the HPV's. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject E2-BP polypeptide. For example, excision of a target sequence which interferes with the expression of a recombinant E2-BP gene, such as one which encodes an antagonistic homolog, can be designed to activate expression of that gene. This interference with expression of the protein can result from a variety of mechanisms, such as spatial separation of the E2-BP gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant E2-binding protein can be regulated via control of recombinase expression.

Use of the crelloxP recombinase system to regulate expression of a recombinant E2-binding protein requires the construction of a transgenic animal containing transgenes encoding both the Cre recombinase and the subject E2-BP protein. Animals containing both the Cre recombinase and a recombinant E2-BP gene can be provided through the construction of "double" transgenic animals. A convenient method for providing such animals is to mate two transgenic animals each containing a transgene, e.g., an E2-BP gene and recombinase gene.

One advantage derived from initially constructing transgenic animals containing a E2-BP transgene in a recombinase-mediated expressible format, particularly derives from the likelihood that the subject protein will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic E2-BP transgene is silent will allow the study of progeny from that founder in which disruption of E2-BP mediated induction in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the E2-BP transgene could remain silent into adulthood until "turned on" by the introduction of the trans-activator.

In an exemplary embodiment, the "transgenic non-human animals" of the invention are produced by introducing transgenes into the germline of the non-human animal. Embryonic target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germn line of the resulting chimeric animal. For review see Jaenisch, R. (1988) *Science* 240:1468–1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous E2-BP gene, such that tissue specific and/or temporal control of inactivation of an E2-BP allele can be controlled as above.

E2-BP Polypeptides

The invention includes recombinant E2-binding polypeptides which are encoded by genes derived from eukaryotic organisms, e.g. mammals, e.g., primates, e.g. humans. The term "recombinant protein" refers to a protein of the present invention which is produced by recombinant DNA techniques, wherein generally DNA encoding the subject E2-binding protein is inserted into a suitable expression vector which is in turn used to transform a host cell to produce the heterologous protein. The phrase "derived from", with respect to a recombinant gene encoding the recombinant E2-BP, is meant to include within the meaning of "recombinant protein" those proteins having an amino acid sequence of a native E2-BP of the present invention, or an amino acid sequence similar thereto which is generated by mutations including substitutions and deletions (including truncation) of a naturally occurring E2-binding protein of a organism. Recombinant proteins preferred by the present invention, in addition to native E2-binding proteins, are at least 60% homologous, more preferably 70% homologous and most preferably 80% homologous with an amino acid sequence shown in one of SEQ ID NOS:5–8. Polypeptides having an activity of the subject E2-binding proteins (i.e. either agonistic or antagonistic) and having at least about 90%, more preferably at least about 95%, and most preferably at least about 98–99% homology with a sequence of either in SEQ ID NO:5–8 are also within the scope of the invention.

The invention includes recombinant forms of the subject E2-binding proteins which are encoded by genes derived from a organism and which have amino acid sequences evolutionarily related to an E2-binding protein of either SEQ ID NO:5–8. Such recombinant E2-binding proteins preferably are capable of functioning in one of either role of an agonist or antagonist of at least one biological activity of the present E2-BPs.

The E2-BP produced by expression of the nucleic acids of the invention can be obtained from cell culture using conventional techniques, e.g., by inserting the nucleic acid into a cell, culturing the cell, and obtaining the protein from the culture, e.g., from the cultured cell or from the medium in which the cell grows. The invention also includes methods of producing the subject E2-binding proteins. For example, a host cell transfected with a nucleic acid vector directing expression of a nucleotide sequence encoding the subject E2-binding protein can be cultured under appropriate conditions to allow expression of the peptide to occur. The peptide may be secreted and isolated from a mixture of cells and medium containing the recombinant E2-BP. Alternatively, the peptide may be retained cytoplasmically and the cells harvested, lysed and the protein isolated. A cell culture includes host cells, media and other byproducts.

Suitable media for cell culture are well known in the art. The recombinant E2-BP peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant E2-binding protein is a fusion protein containing a domain which facilitates its purification, such as an E2-BP/GST fusion protein.

The invention includes a host cell transfected to express a recombinant form of at least one of the subject E2-binding proteins. The host cell may be any prokaryotic or eukaryotic cell. Thus, a nucleotide sequence derived from the cloning of the E2-binding proteins of the present invention, encoding all or a selected portion of a protein, can be used to produce a recombinant form of an E2-BP via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant E2-binding proteins, or portions thereof, by microbial means or tissue-culture technology in accord with the subject invention.

The recombinant E2-binding gene can be produced by ligating nucleic acid encoding a subject E2-binding protein, or a portion thereof, into a vector suitable for expression in either prokaryotic cells, eukaryotic cells, or both. Expression vectors for production of recombinant forms of the subject E2-binding proteins include plasmids and other vectors. For instance, suitable vectors for the expression of an E2-BP include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye cademic Press, p. 83, incorporated by reference herein). These vectors can replicate in E. coli due the presence of the pBR322 ori, and in S. cerevisiae due to the replication eterminant of the yeast 2 micron plasmid. In addition, drug resistance markers such as ampicillin can be used. In an illustrative embodiment, an E2-binding protein is produced recombinantly utilizing an expression vector generated by sub-cloning a gene encoding the protein from pRS306-E2BP library (ATCC accession No:75915) using, for example, primers based on SEQ ID NO:1–4 and/or primers based on the flanking plasmid sequence (e.g. the primers represented by SEQ ID NOS: 13–15).

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17. In some instances, it may be desirable to express the recombinant E2-BP by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of one of the subject E2-binding protein is desired, i.e. a truncation mutant, it may be necessary to add a start codon (ATG) to the oligonucleotide fragment containing the desired sequence to be expressed. It is known in the art that a methionine at the N-terminal position can be enzymatically cleaved by the use of the enzyme methionine aminopeptidase (MAP). MAP has been cloned from E. coli (Ben-Bassat et al. (1987) J. Bacteriol 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing E2-BP-derived polypeptides in a host which produces MAP (e.g., E. coli or CM89 or S. cerevisiae), or in vitro by use of purified MAP (e.g., procedure of Miller et al., supra).

The coding sequences for polypeptides of the invention can be incorporated as a part of a fusion gene including a nucleotide sequence encoding a different polypeptide. This type of expression system can be useful under conditions where it is desirable to produce an immunogenic fragment of an E2-binding protein. For example, the VP6 capsid protein of rotavirus can be used as an immunologic carrier protein for portions of the E2-BP polypeptide, either in the monomeric form or in the form of a viral particle. The nucleic acid sequences corresponding to the portion of a subject E2-binding protein to which antibodies are to be raised can be incorporated into a fusion gene construct which includes coding sequences for a late vaccinia virus structural protein to produce a set of recombinant viruses expressing fusion proteins comprising a portion of the protein E2-BP as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an E2-binding protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a subject E2-binding protein is obtained directly from organo-chemical synthesis of the peptide onto an oligomeric branching lysine core (see, for example, Posnett et al. (1988) JBC 263:1719 and Nardelli et al. (1992) *J. ImmunoL* 148:914). Antigenic determinants of the subject E2-binding proteins can also be expressed and presented by bacterial cells.

In addition to using fusion proteins to enhance immunogenicity, it is widely appreciated that fusion proteins can also facilitate the expression of proteins, such as any one of the E2-binding protein of the present invention. For example, an E2-binding protein of the present invention can be generated as a glutathione-S-transferase (GST- fusion protein). Such GST fusion proteins can enable easy purification of the E2-binding protein, such as by the use of glutathione-derivatized matrices (see, for example, *Current Protocols in Molecular Biology*, eds. Ausabel et al. (N.Y.: John Wiley & Sons, 1991)). In another embodiment, a fusion gene coding for a purification leader sequence, such as a poly-(His)/enterokinase cleavage site sequence at the N-terminus of the desired portion of the E2-binding protein, can allow purification of the poly(His)- expressed E2-BP- fusion protein by affinity chromatography using a $Ni^{2+}$ metal resin. The purification leader sequence can then be subsequently removed by treatment with enterokinase (e.g., see Hochuli et al. (1987) J. *Chromatography* 411:177; and Janknecht et al. *PNAS* 88:8972).

Techniques for making fusion genes are known to those skilled in the art. For example, the joining of various DNA fragments coding for different polypeptide sequences is performed in accordance with conventional techniques, employing blunt-ended or stagger ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

The invention also includes isolated E2-binding polypeptides which are isolated from, or otherwise substantially free of other cellular or viral proteins, especially papillomavirus proteins, normally associated with the E2-binding protein. When referring to polypeptides of the invention, the term "substantially pure or purified preparations" are defined as E2-BP preparations which are substantially free of at least one polypeptide, polysaccharide, or lipid with which the E2-BP protein naturally occurs with in the cell. Preparations which are "substantially free of other cellular or viral proteins" (also referred to herein as "contaminating proteins") have less than 20% (by dry weight) contaminating protein, and preferably having less than 5% contaminating protein. Functional forms of the subject E2-binding proteins can be prepared, for the first time, as purified preparations by using a cloned gene as described herein. Alternatively, the subject E2-binding proteins can be isolated by affinity purification using, for example, E2-derivatized matrices.

Isolated peptidyl portions of the subject E2-binding proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an E2-binding protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of an E2-binding protein activity, such as by microinjection assays.

The structure of E2-binding proteins can be modified, e.g., to enhance therapeutic or prophylactic efficacy, or stability (e.g., ex vivo shelf life and resistance to proteolytic degradation in vivo). Such modified peptides, when designed to retain at least one activity of the naturally-occurring form of the protein, are considered finctional equivalents of the E2-binding protein described in more detail herein. Such modified peptide can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur -containing=cysteine and methionine. (see, for example, *Biochemistry*, 2nd ed., Ed. by L. Stryer, WH Freeman and Co.: 1981). Whether a change in the amino acid sequence of a peptide results in a functional E2-BP homolog can be readily determined by assessing the ability of the variant peptide to produce a response in cells in a fashion similar to the wild-type E2-BP or to another E2-BP polypeptide of the invention. Peptides in which more than one replacement has taken place can be tested in the same manner.

The invention includes a method of generating sets of combinatorial mutants of the subject E2-binding proteins, as well as truncation and fragmentation mutants, and is especially useful for identifying potential variant sequences which are finctional in binding to a PV E2 protein, especially an E2 protein of a high risk HPV. One purpose for screening such combinatorial libraries is, for example, to isolate novel E2-BP homologs which function as one of either an agonist or antagonist of the biological activities of the wild-type ("authentic") protein, or alternatively, possess novel activities all together. To illustrate, E2-BP homologs can be engineered by the present method to provide proteins which bind E2and which block E2-mediated gene transcription in order to inhibit papillomavirus infection, transformation and/or immortalization. Such proteins, when expressed from recombinant DNA constructs, can be used in gene therapy protocols.

Mutagenesis can give rise to E2-BP homologs which have intracellular half-lives significantly different than the corresponding wild-type protein. For example, the altered protein can be rendered either more stable or less stable to proteolytic degradation or other cellular process which result in destruction of, or otherwise inactivation of, an E2-binding protein. Such E2-BP homologs, and the genes which encode them, can be utilized to alter the envelope of expression for the particular recombinant E2binding protein by modulating the half-life of the recombinant protein. For instance, a short half-life can give rise to more transient biological effects associated with a particular recombinant E2-BP and, when part of an inducible expression system, can allow tighter control of recombinant protein levels within the cell. As above, such proteins, and particularly their recombinant nucleic acid constructs, can be used in gene therapy protocols.

In an illustrative embodiment of this method, the amino acid sequences for a population of E2-BP homologs or other related proteins are aligned, preferably to promote the highest homology possible. Such a population of variants can include, for example, E2-BP homologs from one or more species, or E2-BP homologs from the same species but which differ due to mutation. Amino acids which appear at each position of the aligned sequences are selected to create a degenerate set of combinatorial sequences.

In a preferred embodiment, the combinatorial E2-BP library is produced by way of a degenerate library of genes encoding a library of polypeptides which each include at least a portion of potential E2-BP sequences. A mixture of synthetic oligonucleotides can be enzymatically ligated into gene sequences such that the degenerate set of potential E2-BP sequences are expressible as individual polypeptides, or alternatively, as a set of larger fusion proteins (e.g. for phage display) containing the set of E2-BP sequences therein.

There are many ways by which the library of potential E2-BP homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential E2-BP sequences. The synthesis of degenerate oligonucleotides is well known in the art (see for example, Narang, SA (1983) *Tetrahedron* 39:3; Itakura et al. (1981) *Recombinant DNA, Proc* 3rd Cleveland Sympos. Macromolecules, ed. AG Walton, Amsterdam: Elsevier pp. 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Techniques for screening gene products of combinatorial libraries made by point mutations, and for screening cDNA libraries for gene products having a preselected property are known in the art. Such techniques will be generally adaptable for rapid screening of the gene libraries generated by the combinatorial mutagenesis of E2-BP homologs. The most widely used techniques for screening large gene libraries typically includes cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate E2-BP sequences created by combinatorial mutagenesis techniques.

In one screening assay, the candidate E2-BP gene products are displayed on the surface of a cell or viral particle, and the ability of particular cells or viral particles to bind an E2 protein, such HPV-16 E2, via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled E2can be used to score for potentially functional E2-BP homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affmity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J.* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27–9400–01) can be easily modified for use in expressing and screening E2-BP combinatorial libraries. For instance, the pCANTAB 5 phagemid of the RPAS kit contains the gene which encodes the phage gII coat protein. The E2-BP combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13K07 helper phage to rescue the phagemid and its candidate E2-BP gene insert. The resulting recombinant phage contain phagemid DNA encoding a specific candidate E2-BP, and display one or more copies of the corresponding fusion coat protein. Those phage-displayed candidate E2-BPs which are capable of binding a E2 are selected or enriched by panning with E2. For instance, the phage library can be panned on glutathione immobilized E2-GST fusion proteins, and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for E2-BP homologs, which can retain an ability to bind E2 which can subsequently be screened for further biological activities in order to differentiate agonists and antagonists.

In light of the present disclosure, other forms of mutagenesis generally applicable will be apparent to those skilled in the art in addition to the aforementioned combinatorial mutagenesis approach. For example, E2-BP homologs (both agonist and antagonist forms) can be generated and screened using, for example, alanine scanning mutagenesis and the like (Rufet al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); or by saturation mutagenesis (Meyers et al. (1986) *Science* 232:613).

Peptide Mimetics

The invention also provides for reduction of the E2-binding domains of the subject E2-binding proteins to generate mimetics, e.g., peptide or non-peptide agents, which are able to disrupt binding of an E2-BP of the present invention with a papillomavirus E2 protein. Thus, such mutagenic techniques are particularly useful to map the determinants of the E2-BP which participate in protein-protein interactions involved in, for example, binding of the subject E2-binding protein to a PV E2 protein. To illustrate, the critical residues of a subject E2-binding protein which are involved in molecular recognition of E2 can be determined and used to generate E2-BP-derived peptidomimetics which competitively inhibit binding of the E2-BP with E2(see, for example, "Peptide inhibitors of human papillomavirus protein binding to retinoblastoma gene protein" European patent applications EP-412,762A and EPB31,080A). By employing, for example, scanning mutagenesis to map the amino acid residues of a particular E2-binding protein involved in binding E2, peptidomimetic compounds (e.g., diazepine or isoquinoline derivatives) can be generated which mimic those residues in binding to E2, and which therefore can inhibit binding of the E2-BP to E2 and thereby interfere with the function of E2 in PV infection. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J. Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J. Chem Soc Perkin Trans* 1:1231), and β-aminoalcohols (Gordon et al. (1985) *Biochem Biophys Res Commun*126:419; and Dann et al. (1986) *Biochem Biophys Res Commun* 134:71).

Antibodies

The invention also includes antibodies specifically reactive with one of the subject E2-binding proteins. For example, by using inmunogens derived from the present activity E2-binding proteins, based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide (e.g., E2-binding protein or an antigenic fragment which is capable of eliciting an antibody response). Techniques for conferring immunogenicity on a protein or peptide include conjugation to carriers or other techniques well known in the art. An immunogenic portion of the subject E2-binding proteins can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the E2-binding proteins of the present invention, e.g. antigenic determinants of a protein represented by one of SEQ ID NOS:5–8 or a closely related human or non-human mammalian homolog (e.g. 90 percent homologous, more preferably at least 95 percent homologous). In yet a further preferred embodiment of the present invention, the anti-E2-BP antibodies do not substantially cross react (i.e. react specifically) with a protein which is: e.g., less than 90 percent homologous to one of SEQ ID NOS:5–8; e.g. less than 95 percent homologous with one of SEQ ID NOS: 5–8; e.g. less than 98–99 percent homologous with one of SEQ ID NOS:5–8. By "not substantially cross react", it is meant that the antibody has a binding affinity for a non-homologous protein (e.g., E2) which is less than 10 percent, more preferably less than 5 percent, and even more preferably less than 1 percent, of the binding affinity for a protein of SEQ ID NOS:5–8.

Following immunization, anti-E2-BP antisera can be obtained and, if desired, polyclonal anti-E2-BP antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with an E2-binding protein of the present invention and monoclonal antibodies isolated from a culture comprising such hybridoma cells.

The term antibody as used herein is intended to include fragments thereof which are also specifically reactive with one of the subject E2-binding protein. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab fragments. The antibody of the present invention is furter intended to include bispecific and chimeric molecules having an anti-E2-BP portion.

Both monoclonal and polyclonal antibodies (Ab) directed against E2-BP or E2-BP variants, and antibody fragments such as Fab' and $F(ab')_2$, can be used to block the action of E2-BP and allow the study of the role of a particular E2binding protein of the present invention in papillomavirus infection, transformation and/or immortalization, as well as the normal cellular function of the E2-binding protein, e.g. by microinjection of anti-E2-BP antibodies of the present invention.

Antibodies which specifically bind E2-BP epitopes can also be used in immunohistochemical staining of tissue samples in order to evaluate the abundance and pattern of expression of each of the subject E2-binding proteins. Anti-E2-BP antibodies can be used diagnostically in immuno-precipitation and immuno-blotting to detect and evaluate E2-BP levels in tissue or bodily fluid as part of a clinical testing procedure. For instance, such measurements as the level of E2-BP/E2complexes can be useful in predictive valuations of the onset or progression of HPV infection. Likewise, the ability to monitor E2-BP levels in an individual can allow determination of the efficacy of a given treatment regimen for an individual afflicted with such a disorder. The level of an E2-binding protein can be measured in cells found in bodily fluid, such as in samples of cerebral spinal fluid, or can be measured in tissue, such as produced by biopsy. Diagnostic assays using anti-E2-BP antibodies can include, for example, immunoassays designed to aid in early diagnosis of a neoplastic or hyperplastic disorder, e.g., the presence of cancerous cells in the sample, e.g., PV-infected cells, e.g., PV-transformed cells, e.g., PV-immortalized cells, e.g., to detect cells in which a lesion of the E2-BP gene has occurred.

Another application of anti-E2-BP antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject E2-BP can then be detected with antibodies, as, for example, reacting nitro-cellulose filters lifted from infected plates with anti-E2-BP antibodies. Phage, scored by this assay, can then be isolated from the infected plate. Thus, the presence of E2-BP homologs can be detected and cloned from other animals, and alternate isoforms (including splicing variants) can be detected and cloned from human sources.

E2-BP Nucleic Acids

The nucleotide sequence determined from the cloning of the subject E2-binding proteins from a human cell line will further allow for the generation of probes designed for use in identifying E2-BP homologs in other human cell types, as well as E2-BP homologs from other animals. For instance, the present invention also provides a probe/primer including a substantially purified oligonucleotide, wherein the oligonucleotide includes a region of nucleotide sequence which hybridizes under stringent conditions to at least 10 consecutive nucleotides of sense or anti-sense sequence of one of SEQ ID NOS: 1–4, or naturally occurring mutants thereof. In preferred embodiments, the probe/primer further comprises a label group attached thereto and able to be detected, e.g. the label group is selected from the group consisting of radioisotopes, fluorescent compounds, enzymes, and enzyme co-factors. Such probes can also be used as a part of a diagnostic test kit for identifying transformed cells, such as for measuring a level of an E2-BP nucleic acid in a sample of cells from a patient; e.g. measuring an E2-BP mRNA level; e.g. determining whether a genomic E2-BP gene has been mutated or deleted.

Nucleotide probes can be generated from the cloned sequence of the subject E2-binding proteins which allow for histological screening of intact tissue and tissue samples for the presence of an E2-BP MRNA. Similar to the diagnostic uses of anti-E2-BP antibodies, the use of probes directed to E2-BP mRNAs, or to genomic E2-BP sequences, can be used for both predictive and therapeutic evaluation of allelic mutations which might be manifest in, for example, neoplastic or hyperplastic disorders (e.g. unwanted cell growth). Used in conjunction with anti-E2-BP antibody immunoassays, the nucleotide probes can help facilitate the determination of the molecular basis for a developmental disorder which may involve some abnormality associated with expression (or lack thereof) of an E2-binding protein. For instance, variation in E2-BP synthesis can be differentiated from a mutation in the E2-BP coding sequence.

Diagnostic Screens

The invention includes a method for determining if a subject is at risk for a disorder characterized by unwanted cell proliferation. In preferred embodiments, the subject method can be generally characterized as comprising detecting, in a tissue of the subject (e.g. a human patient), the presence or absence of a genetic lesion characterized by at least one of (i) a mutation of a gene encoding one of the subject E2-BPs or (ii) the misexpression of an E2-BP gene. To illustrate, such genetic lesions can be detected by ascertaining the existence of at least one of (i) a deletion of one or more nucleotides from a subject E2-BP gene, (ii) an addition of one or more nucleotides to such an E2-BP gene, (iii) a substitution of one or more nucleotides of an E2-BP gene, (iv) a gross chromosomal rearrangement of one of the subject E2-BP genes, (v) a gross alteration in the level of a messenger RNA transcript of an E2-BP gene, (vi) the presence of a non-wild type splicing pattern of a messenger RNA transcript of an E2-BP gene, and (vii) a non-wild type level of an E2-binding protein. In one aspect of the invention there is provided a probe/primer comprising an oligonucleotide containing a region of nucleotide sequence which is capable of hybridizing to a sense or antisense sequence of one of SEQ ID NOS: 1–4, or naturally occurring mutants thereof, or 5' or 3' flanking sequences or intronic sequences naturally associated with the subject E2-BP genes. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos. 4,683,195 and 4,683,202) or, alternatively, in a ligation chain reaction (LCR) (see, e.g., Landegran et al. (1988) *Science,* 241:1077–1080; and Nakazawa et al. (1944) *PNAS* 91:360–364) the later of which can be particularly useful for detecting point mutations in the E2-BP gene. Alternatively, the level of E2-binding protein can detected in an immunoassay.

Other E2-BP Screens

The use of anti-sense techniques (e.g. microinjection of antisense molecules, or transfection with plasmids whose transcripts are anti-sense with regard to an E2-BP MRNA or gene sequence) can be used to investigate role. of each of the subject E2-BP in HPV-mediated events (infection, transformation and/or immortalization), as well as the normal cellular function of each of the novel E2-BPs, e.g. in regulation of transcription and/or replication, by inhibiting endogenous production of a particular E2-binding protein. Such techniques can be utilized in cell culture, but can also be used in the creation of transgenic animals.

Drug Screening Assays

The invention includes assays which can be used to screen for drugs which are either agonists or antagonists of the normal cellular function of the subject E2-binding proteins, or of their role in papillomavirus infection. In one embodiment, the assay evaluates the ability of a compound to modulate binding between an E2-binding protein and an E2 protein, e.g., E2from a high risk HPV. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. The effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. In an exemplary screening assay of the present invention, the compound of interest is contacted with an isolated and purified E2-binding protein. The mixture of the compound and E2-binding protein is then added to a composition containing a papillomavirus E2 protein but which does not contain E2-BP. Detection and quantification of E2/E2-BP complexes provides a means for determining the compound's efficacy at inhibiting (or potentiating) complex formation between the E2 protein and the E2-binding protein. The efficacy of the compound can be assessed by generating dose response curves from data obtained using various concentrations of the test compound. A control assay can also be performed to provide a baseline for comparison. In the control assay, isolated and purified E2-BP is added to a composition containing the E2 protein, and the formation of E2/E2-BP complex is quantitated in the absence of the test compound.

Complex formation between the E2-binding protein and an E2 may be detected by a variety of techniques. For instance, modulation of the formation of complexes can be quantitated using, for example, defectably labeled proteins (e.g. radiolabeled, fluorescently labeled, or enzymatically labeled, by immunoassay, or by chromatographic detection.

Typically, it will be desirable to immobilize either the E2 protein or the E2-binding protein to facilitate separation of E2/E2-BP complexes from uncomplexed forms of one of the proteins, as well as to accommodate automation of the assay. In one embodiment, a fusion protein can be provided which adds a domain that allows the protein to be bound to a matrix. For example, glutathione-S-transferase/E2(GST/E2) fusion proteins, described below, can be adsorbed onto glutathione sepharose beads (Sigma Chemical, St. Louis, MO) or glutathione derivatized microtitre plates, which are then combined with the E2-binding protein, e.g. an $^{35}$S-labeled E2-binding protein, and the test compound and incubated under conditions conducive to complex formation, e.g., at 4° C. in a buffer of 2 mM Tris-HCl (pH 8), 1 nM EDTA, 0.5% Nonidet P-40, and 100 mM NaCl. Following incubation, the beads are washed to remove any unbound E2-BP, and the matrix bead-bound radiolabel determined directly (e.g. beads placed in scintilant), or in the supernantant after the E2/E2-BP complexes are dissociated. Alternatively, the complexes can dissociated from the bead, separated by SDS-PAGE gel, and the level of E2-BP found in the bead fraction quantitated from the gel using standard electrophoretic techniques.

Other techniques for immobilizing proteins on matrices are also available for use in the subject assay. For instance, the E2 protein can be immobilized utilizing conjugation of biotin and streptavidin. For instance, biotinylated E2 can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with E2 can be derivatized to the wells of the plate, and E2 tapped in the wells by antibody conjugation. As above, preparations of an E2-binding protein and a test compound are incubated in the E2-presenting wells of the plate, and the amount of E2/E2-BP complex trapped in the well can be quantitated. Exemplary methods for detecting such complexes, in addition to those described above for the GST-immobilized complexes, include immunodetection of complexes using antibodies reactive with the E2-binding protein, or which are reactive with the E2 protein and compete for binding with the E2-BP; as well as enzyme-linked assays which rely on detecting an enzymatic activity associated with the E2-binding protein. In the instance of the latter, the enzyme can be chemically conjugated or provided as a fusion protein with the E2-binding protein. To illustrate, the E2-binding protein can be chemically cross-linked with alkaline phosphatase, and the amount of E2-BP trapped in the complex can be assessed with a chromogenic substrate of the enzyme, e.g. paranitrophenyl phosphate. Likewise, a fusion protein comprising the E2-BP and glutathione-S-transferase can be provided, and complex formation quantitated by detecting the GST activity using 1-chloro-2,4-dinitrobenzene (Habig et al (1974) *J. Biol Chem* 249:7130).

For processes which rely on immunodetection for quantitating one of the proteins trapped in the complex, antibodies against the protein, such as the anti-E2-BP antibodies described herein, can be used. Alternatively, the protein to be detected in the complex can be "epitope tagged" in the form of a fusion protein which includes, in addition to the E2-BP or E2 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J. Biol Chem* 266:21150–21157) which includes a 10-residue sequence from c-myc, as well as the pFLAG system (International Biotechnologies, Inc.) or the pEZZ-protein A system (Pharamacia, N.J.).

In addition to the cell free systems, the present invention further contemplates cellbased and whole animal assays for identifying agents which affect the biological function of a PV E2 protein or an E2-binding protein. While these assay systems can certainly be used as primary screens for initial identification of compounds which alter the binding of the two proteins, the in vivo assays are more typically used as "secondary" screens for further accessing compounds identified in the primary screen (e.g., the "hits"). For example, secondary screens can be used to evaluate the ability of the agent to actually modulate the function of E2 in vivo, as well as to assess the cytotoxicity, bioavailability, and other pharmacokinetic parameters of the test compound. In an exemplary embodiment, the subject E2-binding proteins can be used to generate an interaction trap assay, as described in the examples below (see also, U.S. Pat. No. : 5,283,317; PCT publication WO94/10300; Zervos et al. (1993) *Cell* 72:223–232; Madura et al. (1993) *J. Biol Chem* 268:12046–12054; Bartel et al. (1993) *Biotechniques* 14:920–924; and Iwabuchi et al. (1993) *Oncogene* 8:1693–1696), which can be used to detect agents which disrupt or enhance binding of the E2-BP to an E2 protein. The interaction trap assay described for the isolation of clone 42A, as well as the LexA based assay described in the examples, are each forms of the interaction trap assay suitable for screening test compounds. In another exemplary embodiment, *Saccharomyces cerevisiae* YPB2 cells are transformed simultaneously with a plasmid encoding a $GAL4^{ad}$-E2fusion and with a plasmid encoding the $GAL4^{db}$ domain fused to subject E2-BP. Moreover, the strain is transformed such that the GAL4-responsive promoter drives expression of a phenotypic marker. For example, the ability to grow in the absence of histidine can depend on the expression of HIS3 gene. When the HIS3 gene is placed under the control of a GAL4-responsive promoter, relief of this auxotrophic phenotype indicates that a functional GAL4 activator has been reconstituted through the interaction of E2 and the E2-BP. Thus, agent able to inhibit E2-BP interaction with E2 will result in yeast cells unable to grow in the absence of histidine. Alternatively, the phenotypic marker (e.g. instead of the HIS3 gene) can be one which provides a negative selection when expressed, such that agents which disrupt E2/E2-BP interactions confer positive growth selection to the cells.

In instances wherein one of the subject E2-binding proteins possess an enzymatic activity, inhibitors of the enzymatic activity can be identified using assays derived from measuring the ability of an agent to inhibit catalytic conversion of a substrate by the subject enzyme.

In another aspect, the invention features an animal model for developmental diseases, which has an E2-BP allele which is misexpressed. For example, a mouse can be bred which has an E2-BP allele deleted, or in which all or part of one or more E2-BP exons are deleted. Such a mouse model can then be used to study disorders arising from misexpressed E2-BP genes.

E2 Mutants

In addition to providing a suitable bait protein for a two hybrid assay, the E2 mutants defective in transactivation are also useful in disrupting the biological activity of the wild-type E2 protein (Androphy et al., (1987) *Nature*, 324:70–73), and therefore can be used to alter the regulation of the papillomavirus viral cycle. For instance, each of the gene constructs described above, particularly those useful for gene therapy, can also be used to deliver a gene encoding one of the subject E2 transactivation-defective mutants to a papillomavirus infected cell. As described herein, these.E2 mutants can advantageously exert their anti-viral effect by interfering with transcriptional activation of viral genes by native E2 proteins in cells infected with papillomavirus. The E2 transactivation repressors of the present invention are characterized by an ability to bind to E2 responsive elements in the PV genome, but an inability to cause activation of transcription of PV genes ordinarily under the transcriptional control of E2. Accordingly, the mutant E2 proteins form complexes consisting of homodimers and heterodimers (e.g. includes a wild-type E2) which compete with homodimers of wild-type E2 for binding to E2 responsive elements in the PV genome.

Isolation of Transactivation Defective Mutants of BPV-1 E2 in Amino Acids 1 to 133

The mutagenesis and screening that resulted in the isolation of transactivation defective mutants in the first 133 amino acids of E2was done essentially as described herein for YEplac112GE2 87L, 131H. PCR misincorporation mutagenesis (using YEplac112GE2 as the template) was carried out with primers EA59 ($^{5'}$ CTCGGATCCATG-GAG ACAGCATG $^{3'}$)(SEQ ID NO:10) and EA18 ($^{5'}$ GCT-GCCAGCCGTCCTC $^{3'}$)(SEQ ID NO:11). The 448 nucleotide (nt.) PCR product was cleaved with either, restriction endonucleases BamH1and Bgl1 or Bgl1 and Acc1, and the cleavage products were gel purified. The purified fragments (BamH1/Bgpl1, nt 1 to 210 and Bgl1/Acc1, nt. 211 to 399) were used to construct separate mutant libraries in M13mp19E2-286. This vector contains a BamH1/Kpn1 fragment encoding the first 286 amino acids of E2, and was used here because, unlike YEplac112GE2, the Acc1 and Bgl1 sites in E2 are unique in this vector. Sequences encoding amino acids 1 to 286 for both mutant libraries in M13mp19E2-286 were transferred to Yeplac112GE2 as BamH1/Kpn1 fragments placing the mutations in the context of fill length E2. The two YEplac112GE2 mutant libraries spanning E2 amino acids 1 to 71 and 72 to 133 were used to isolate transactive defective mutants by screening in *Saccharomyces cerevesiae*.

In a similar manner, a misincorporation library of sequences encoding amino acids 134 to 215 was made using primers EA 37 (5' CCAGGGTGGTAGAGGTG 3')(SEQ ID NO:16) and EA 107 (5' CCTTCGCTAGCGACCCA-GACTC 3')(SEQ ID NO:17). The PCR product was cleaved with AccI and NheI, and after gel purification was used to construct a library in M13mp19E2-286$^N$. This vector is identical to M13mp19E2-286, except that silent changes at amino acids 215 and 216 have been made creating an NheI cleavage site. This library was transfeffed to the context of full length E2as was described for the others.

Mammalian Cell Transfections

Approximately 3–5×10$^6$ cells were grown to 50% confluence and electroporated with a Bio-Rad Gene Pulser. COS-7 cells were electroporated at 0.25 KV and 960 μFD. Electroporations into COS-7 cell lines introduced 20μg of reporter plasmid, 20μg of effector plasmid and 360 μg of salmon sperm DNA. These conditions and input DNA concentrations were determined to be optimal for COS-7 cell electroporations and are known in the art. Each COS-7 electroporation was plated and fed with fresh media at 24 hours post electroporation. Cell media was assayed for human growth hormone (hGH) concentration at 3 days post-electroporation. In the transcription activation assay used to test E2 mutants, hGH was connected to the E2 responsive promoter in the same manner as in the β-GAL assay described herein. Whole cell extracts were prepared from electroporated COS-7 cells by lysing directly in denaturing buffer. To confirm protein levels, western blots of all mutants reported were performed using the E2 antibody II-2 (EA).

Summary of N-Terminal E2 Mutations: Activation Data in Yeast and Cos-7 Cells

| REGION | POINT MUTANT | β-GAL ASSAY % of wildtype | hGH ASSAY % of wildtype |
|---|---|---|---|
| | Q 15 H | <1% | 0 |
| | D 24 A | 75% | 34% |
| | K 25 E | 67% | 77% |
| | E 39 G | <1% | 2% |
| | A 46 E | 88% | 112% |
| | F 87 S | <1% | 2% |
| | W 92 R | <1% | 2% |
| | W 99 C | <1% | 4% |
| | P 106 S | <1% | 5% |
| | N 127 Y | 14% | 44% |
| | Y 138 H | | 14% |
| | W 145 R | | 1% |
| | R 208 G | | 22% |

The position of the point mutation is indicated by the amino acid and its location in the ORF, e.g., R 208 G indicates Argenine at position 208 that has been substituted with Glycine at that position.
YES=absolutely conserved across PV's
YES=all but 1 or 2 exceptions are conserved across PV's
yes=Homologous aa (F,Y,W)
No=No conservation noted
Transcriptionally defective E2 point mutants are those that exhibit <50% activity of the wild type E2.

E2-Mediated Interaction Trap Assay

Another aspect of the present invention concerns a novel in vivo method for the isolation of genes encoding proteins which physically interact with a "bait" protein, e.g. a protein suspected or known to be a molecular target for therapeutic intervention or of diagnostic value. The method relies on detecting the reconstitution of a finctional transcriptional activator mediated by protein-protein interactions with the bait protein. In particular, the method makes use of chimeric genes which express hybrid proteins. The first hybrid comprises the DNA-binding domain of a papillomavirus E2 protein fused to the bait protein. The second hybrid protein contains a transcriptional activation domain fused to a "fish" protein, e.g. a test protein derived from a cDNA library. If the fish and bait proteins are able to interact, they bring into close proximity the DNA-binding and transcriptional activator domains. This proximity is sufficient to cause transcription of a reporter gene which is operably linked to an E2 transcriptional regulatory site (e.g. an E2 binding site), and expression of the marker gene can be detected and used to score for the interaction of the bait protein with another protein.

One advantage of this method is that a multiplicity of proteins can be simultaneously tested to determine whether any interact with the bait protein. For example, a DNA fragment encoding the E2 DNA-binding domain can be fused to a DNA fragment encoding the bait protein in order to provide one hybrid. This hybrid is introduced into the cells carrying the marker gene and the transfected cells caused to express the E2/bait fusion protein. For the second hybrid, a library of plasmids can be constructed which may include, for example, total mammalian complementary DNA (cDNA) fused to the DNA sequence encoding the activation domain. This library is introduced into the cells carrying the first hybrid. If any individual plasmid from the test library encodes a protein that is capable of interacting with the bait protein, a positive signal may be obtained by detecting expression of the reporter gene. In addition, when the interaction between the bait protein and a novel protein occurs, the gene for the newly identified protein is readily available.

Accordingly, the method comprises providing a host cell, preferably a yeast cell, more preferably Saccharomyces cerevisiae or Schizosaccharomyces pombe, containing gene constructs encoding each of the chimeric "bait" and "fish" proteins, as well as an E2 responsive reporter gene which, when expressed, causes a phenotypic change in the host cell. Expression of each of the chimeric proteins is induced (although constitutive expression of one or both of the proteins is also acceptable), and the host cells are isolated or otherwise selectively enriched based on the phenotypic characteristics conferred by the expression of the reporter gene in cells in which the bait and fish chimeras are capable of binding to one and other. For instance, the reporter gene can provide a protein which confers a drug resistant phenotype (e.g., resistance to chloroamphenicol or neomycin), an enzyme which provides for colorimetric or luminescence detection (e.g., GAL4 or luciferase), a gene product which rescues an auxotrophic phenotype (e.g., LEU2, HIS3, Ura3 or LYS2), or any cell surface antigen for which antibodies are available (e.g., for panning).

The method of the present invention, as described above, may be practiced using a kit for detecting interaction between a first test protein and a second test protein. The kit includes a container, two vectors, and a host cell. The first vector contains a promoter and may include a transcription termination signal functionally associated with the first chimeric gene in order to direct the transcription of the first gene. The first gene includes a DNA sequence that encodes an E2 DNA-binding domain and a unique restriction site(s) for inserting a DNA sequence encoding a first test protein (e.g., the "bait" protein) or protein fragment in such a manner that the first test protein is expressed as part of a hybrid protein with the E2 DNA-binding domain. The first vector also includes a means for replicating itself in the host cell and in bacteria. Also included on the first vector is a first marker gene, the expression of which in the host cell permits selection of cells containing the first marker gene from cells that do not contain the first marker gene. Preferably, the first vector is a plasmid.

The kit also includes a second vector which contains a second gene. The second gene also includes a promoter and a transcription termination signal to direct transcription. The second gene also includes a DNA sequence that encodes a transcriptional activation domain and a unique restriction site(s) to insert a DNA sequence encoding the second test protein (e.g., the fish proteins) or protein fragment into the vector, in such a manner that the second test protein is capable of being expressed as part of a hybrid protein with the transcriptional activation domain. Preferably, the transcriptional activation domain of the second hybrid protein is derived from transcriptional activators having separate DNA-binding and transcriptional activation domains. Such transcriptional activators are known to be found in the yeast GAL4 protein, and are also known to be found in the yeast GCN4 and ADR1 proteins. The viral VP16 protein is known to have a strong transcriptional activation domain. Many other proteins involved in transcription also have separable binding and transcriptional activation domains, the latter of which make them useful for the present invention. The second hybrid protein may be encoded on a library of plasmids that contain genomic, cDNA or synthetically generated DNA sequences fused to the DNA sequence encoding the transcriptional activation domain.

The second vector further includes a means for replicating itself in the host cell and in bacteria. The second vector also includes a second marker gene, the expression of which in the host cell permits selection of cells containing the second marker gene from cells that do not contain the second marker gene.

The kit includes a host cell, preferably a yeast strain of *Saccharomyces cerevisiae* or *Schizosaccharomyces pombe*. The host cell contains the detectable gene having a binding site for the E2 DNA-binding domain of the first hybrid protein, e.g., is under the transcriptional control of at least one E2-responsive element. The E2 binding sites are positioned so that the detectable gene expresses a detectable protein when the gene is activated by the transcriptional activation domain encoded by the second vector. Activation of the gene is possible when the transcriptional activation domain is in sufficient proximity to the detectable gene. The host cell, by itself, should be incapable of expressing a protein having a function of the first marker gene, the second marker gene, the DNA-binding domain of the E2 protein, or the transcriptional activation domain.

Accordingly in using the kit, the interaction of the bait protein and fish protein in the host cell causes a measurably greater expression of the detectable gene than when the E2 DNA-binding domain and the transcriptional activation domain are present but fail to interact. The detectable gene may encode an enzyme or other product that can be readily measured. Such measurable activity may include the ability of the cell to grow only when the marker gene is transcribed, or the presence of detectable enzyme activity only when the marker gene is transcribed. Various other markers are well known within the skill of workers in the art.

The cells containing the two hybrid proteins are incubated in an appropriate medium and the culture is monitored for the measurable activity. A positive test for this activity is an indication that the bait protein and the fish protein have interacted. Such interaction brings their respective DNA-binding and transcriptional activation domains into sufficiently close proximity to cause transcription of the marker gene.

Examples

The invention now being generally described, it will be more readily understood by reference to the following examples which are included merely for purposes of illustration of certain aspects and embodiments of the present invention, and are not intended to limit the invention.

Construction of Two Hybrid Assay System

To identify genes encoding proteins that associate with the papillomavirus E2 protein, we employed a modified two-hybrid system that utilizes a genetic selection for genes encoding interacting proteins (see, for example, Fields et al. (1989) *Nature* 340:245–246; Chien et al. (1991) *PNAS* 88:9578–9582; Morrissey et al. (1989) *J Virol* 63:4422–5; and Lamberti et al. (1990) *EMBO J* 9:1907–1913). We have adapted this "two-hybrid system" by starting with a yeast strain expressing a transactivation defective/bovine papillomavirus (BPV) E2 protein and a lacZ reporter driven by a promoter containing four E2 binding elements. The E2 mutant protein can bind the E2 binding sites but does not induce expression of the reporter gene. This strain was then transformed with a library of plasmids in which randomly primed HeLa cell cDNA were inserted C-terminal to the strong VP16 transcription activation domain (Dalton et al. (1992) *Cell* 68:597–612). VP16/cDNA fusion proteins that can interact with the E2 protein, or that can bind the reporter promoter directly, would recruit the VP16 activation domain to the E2 binding sites and activate expression of the lacZ gene, and these yeast cells would subsequently stain blue on x-gal plates.

Briefly, this assay used autonomously replicating yeast plasmids with selectable markers to maintain an E2 responsive β-galactosidase reporter (pL72, 2 micron, LEU2) and a BPV-1 E2 expression construct (URA3). In pKpE2 the expression of the E2 ORF is controlled by the galactose induced GAL4 promoter (pGAL4) (West et al. (1984) *Mol Cell Biol* 4: 2467–2478). The reporter construct contains the *E. coli* β-galactosidase (lacZ) gene under control of a minimal yeast CYC1 promoter to which E2 binding sites (E2RE) were added (Androphy et al. (1987) *Nature* 325:70–73). The lacZ gene is transcribed when E2 inds the E2RE in the promoter and activates transcription, and can be detected as blue color ormation in colonies grown on yeast minimal medium (YMM) containing galactose to induce synthesis of E2 and 5-bromo-4-chloro-3-indolyl-beta-D-galactopyranoside (XGAL) which is the substrate for lacZ. (Guarente (1983) *Meth Enzymol* 101:181–191).

To permit maintenance of the VP16-HeLa cDNA library as well as the E2 and reporter plasmids, it was necessary to modify the yeast strain (BGW1-7a: MATa leu2,2-leu2- , 11; his4-his519,ade1-ade100,ura3-ura52) previously described (Guarente and Mason, (1983) *Cell* 32:1279–1286). To allow maintenance of a third autonomously replicating plasmid, the TRP 1 gene of BGW1-7a was inactivated by one step gene replacement (Alani et al. (1987) *Genetics* 116:541–545). The inactivation vector, pNKY1009 was cleaved with EcoRI, and, following phenol: chloroform extraction and ethanol precipitation, was transformed into BGW1-7a using the lithium acetate method (Ito et al. (1983) *J Bacteriol* 153:163–168). Transformants which grew on YMM 2% glucose, minus uracil were screened for ability to grow in the absence of tryptophan. Colonies which, unlike BGW1-7a demonstrated a requirement for tryptophan were transferred to YMM glucose with tryptophan and 5-fluoro-orotic acid to select for loss of the pNKY1009 encoded URA3 gene (Boeke et al. (1987) *Mol Gen Genet* 197:345). Colonies which grew on this medium were tested for ability to grow on YMM glucose lacking: tryptophan, leucine, or uracil. One isolate which demonstrated a requirement for all three (DBY1) was selected for further study.

To confirm activation of the TRP 1 gene, DBY1 was transformed with YEplac112 which contains the TRP 1 gene and the 2 micron replicon (Gietz and Sugino (1988) *Gene* 74: 527–534). The ability of YEplac112 transformants of DBY1 to grow on YMM glucose minus tryptophan, but not those receiving YEplac181 (LEU2, 2 micron) DNA confirmed that the TRP1 gene of DBY1 was inactivated.

The availability of DBY1 allows the simultaneous presence of the three extrachromosomal replicons required for screening the cDNA library: VP16-HeLa cDNA library, URA3; pL72 LacZ reporter, LEU 2; and YEplac112GE2, TRP1. The YEplac112GE2 construct contains the same pGAL4-BPV1 E2 cassette as does pKpE2. Success of the two hybrid screen requires an E2 molecule with is capable of site specific DNA binding, but unable to activate transcription when bound to the E2RE in the promoter of pL72. As wild type E2 transactivates the pL72 reporter it was necessary to construct mutants of E2 which have these properties.

Similar to other transactivators the transcriptional activation and DNA binding domains of E2can be separated into modular functional units. A carboxy terminal 85 amino acid (325 to 410) of E2 is capable of site specific DNA binding, and when fused to the LexA DNA binding domain, the amino terminal 300 amino acids of E2 are able to activate transcription of a reporter containing LexA DNA binding sites in yeast. The transcriptional activation domain of E2 is less well characterized, but is thought to comprise some or all of amino acids 1 to 161. For this reason we have used region specific mutagenesis to isolate transactivation defective mutants in the amino terminal 161 amino acids of E2.

A library of mutations affecting amino acids 1 to 150 of E2 was prepared by performing the polymerase chain reaction on YEplac112GE2 using primers: EA-59 (5'-, CTCGGATCCCATGGAGACAGCATG-3')(SEQ ID NO:10) and EA-18 (5'-GCTG CCAGCCGTCCTC-3')(SEQ ID NO:11) under conditions favoring misincorporation at adenine residues (Leung et al. (1989) *Method Cell Mol Biol* 1:11–19). The PCR product was cleaved with Acc 1 and Bgl1 and the 186 nt. fragment spanning E2 amino acids 69 to 133 was resolved by electrophoresis in a 1% Tris-acetate-EDTA agarose minigel, cut out of the gel and purified using a Quiex Kit (Quiagen Corp.).

Introduction of the Bgl1/Acc I mutant pool into a wild-type E2 background was done in two steps, since these restriction endonucleases are not unique in YEplac112GE2. The Bgl I/Acc I fragment was first inserted into M13mp129E2–286, which is a bacteriophage M13 vector into which the Bam HI/Kpn I fragment encoding amino acids 1 to 300 from YEplac112GE2 was cloned. The Acc 1 site in the M13 multiple cloning site was destroyed by Acc 1 digestion, Klenow treatment, ligation and transformation prior to insertion of the E2 fragment. The purified fragment was ligated to M13mp19E2–286 which had been cleaved with Acc 1 and Bgl1 and purified as described above. The ligation reaction was reintroduced into *E. coli* MV1190 by electroporation (Dower et al. (1988) *Nucleic Acids Res* 16:6127–6145). Virus extracted from the top agar of the transformation plates was pooled and used to infect MV1190 from which double stranded replicative form DNA (RF DNA) was prepared using a Quiagen Tip100 column (Quiagen Corp.).

The mutant RF DNA was cleaved with Bam HI and Kpn I, and the E2 1 to 286 amino acid fragment was gel purified, and ligated to the YEplac112GE2 fragment containing E2amino acids 287 to 410. The ligation reaction was introduced into *E. coli* DH5α by electroporation, generating library of approximately 30,000 transformants. Colonies were scraped off transformation plates with a glass spreader and combined in a volume of 50 ml of terrific broth (TB) with 50µg/ml ampicillin. After 2 hr. of incubation at 37° C. with shaking, YEplac112GE2 DNA was prepared from the culture with a Quiagen Tip 100 kit.

The YEplac112GE2 mutant library was transformed into DBY1 containing pBsy72, an E2 responsive LacZ reporter identical to pL72, except that it contains an intact URA3 gene (Morrissey and Androphy (1989) *J Virol* 63:4422–4425). Transformants were selected on YMM glucose minus tryptophan and uracil, and replica plated to the same medium and YMM GAL/XGAL minus tryptophan and uracil. After 48 hr. at 30° C. colonies were scored for color formation, and white and light blue colonies were picked off the glucose replica plate into 5 ml. of YMM glucose minus tryptophan and uracil. The next day 2.5 ml. of the culture was pelleted at 1000×g for 5 min. at room temperature, and resuspended in 2.5 ml. of YMM 4% galactose minus tryptophan and uracil. After 12 hr. of incubation at 30° C. with shaking, the cells were pelleted resuspended in an equal volume of 2×SDS/PAGE sample buffer and incubated in a boiling water for 3 minutes.

Mutant yeast extracts were resolved by SDS/PAGE on a 12% gel, and electroblotted to Immobilon P (Millipore). The presence of full length E2 was determined by probing Western blots first with a rabbit anti-BPV1-E2 polyclonal serum, and second with a sheep anti-rabbit alkaline phosphatase conjugate (Sigma) (Prakash et al. (1992) *Genes Dev* 6:105–116). After visualization of E2 bands with a BIORAD alkaline phosphatase kit, mutant extracts were scored for the presence of full length BPV1 E2.

Putative mutant E2 plasmids were then recovered from isolates which scored positive for the presence of full length E2. The remaining 2.5 ml. of the original culture was pelleted and DNA was extracted. as described by Hoffinan and Winston ((1987) *Gene* 57: 262–272), except that after phenol/chloroform extraction DNA was precipitated, washed twice with 70% ethanol, and resuspended in 50 µl of TE (50 mM Tris pH8.0, 10 mM EDTA). Five microliters of each DNA sample was used to transform *E. coli* DH5α as described by Hanahan 1983. Transformation reactions were plated on LB with 50 µg/ml ampicillin and 0.4% XGAL. On this medium the reporter construct (pBsy72) forms blue colonies, while transformants containing YEplac112GE2 are white.

Putative YEplac112GE2 transformants were picked in to 2.5 ml of TB (50µg/ml ampicillin) and incubated overnight at 37° C. with shaking. Plasmid DNA was isolated using the alkaline lysis method, and the identity of plasmid was confirmed by restriction endonuclease digestion (Birnboim and Doly (1979) *Nucleic Acids Res* 7:1513). Isolates were also reintroduced into DBY1 with pBsy72 and tested on GAL/XGAL plates for activation of the reporter. Any putative mutants which activated transcription of the reporter to wild type levels when retested were discarded. The transactivation potential of defective mutants was further characterized by quantitative β-galactosidase assay. Colonies used for the GAL/XGAL plate assay were also inoculated into YMM 2% raffinose (minus tryptophan and uracil) and incubated 12 hr. at 30° C. with shaking. Cells were pelleted at 1000×g for 5 minutes at room temperature, washed with sterile distilled water, and resuspended in YMM 4% High purity galactose (Sigma) minus tryptophan and uracil and incubated as above. After 12 hr. of incubation β-galactosidase activity was determined using the semi-permeabilized cells assay (Guarente (1983) *Meth Enzymol* 101:181–191).

Mutants which scored positive for synthesis of full length E2 in the Western blot, and which failed to transactivate the reporter when retested were characterized by DNA sequence analysis. DNA sequence analysis of the mutants was performed with a Sequenase 2.0 kit (US Biochemicals) and was limited by the use of primers EA-18 (5'-GCT GCC AGC CGT CCT C-3')(SEQ ID No;11) and EA-23 (5'-TCG TCA CCA AAG CGA G-3')(SEQ ID NO:12).

One mutant YEplac112GE2 (87S,131H) was chosen for screening of the HeLa cDNA library. The activation of the LacZ reporter by this was indistinguishable from back ground in a quantitative µ-galactosidase assay and it appeared to have wild type steady state levels of E2 protein as measured by Western blot.

Screening Hela Cell cDNA Library

The VP16-cDNA library and YElpac112GE2 (87S, 131H) were co-transformed into DBYl(pL72) and plated on YMM glucose minus tryptophan, leucine, and uracil. After 72 hr. of incubation at 30° C. colonies were replicated to YMM GAL/XGAL minus tryptophan, leucine, and uracil.

Approximately 1,000,000 transformants were screened, and colonies which showed significant blue color formation after 36 hours at 30° C. were selected for further study.

Approximately 1,000,000 transformants were screen and colonies which showed blue color formation significantly above background were selected. These colonies were struck out of YMM glucose minus tryptophan, leucine, and uracil, and individual colonies were retested on GAL/XGAL for color formation.

The cDNA plasmid was then recovered from colonies which were positive when retested. The vector used to construct the cDNA library (pRS306) has a low copy yeast replicon, but the YEplac112GE2 and pL72 vectors have high copy replicons making it necessary to cure the yeast of the high copy plasmid prior to isolation of cDNA plasmid.

This was done by growing the yeast several generations while selecting only for the low copy replicon. The colonies were inoculated into 2.5 ml. of YMM glucose minus uracil medium, and incubated overnight at 30° C. with shaking. The overnight was diluted 1 to 50 in the same medium and incubated over night. After this process was repeated 5 times a portion of the last overnight culture was plated on YMM glucose minus uracil, and individual colonies were picked to a master plate, which was replica plated to YMM glucose plates with the following amino acid deficiencies: uracil, uracil and leucine, and uracil and tryptophan.

Colonies which grew only on the minus uracil plated no longer contained YEplac112GE2 and pL72. Total DNA was prepared from these isolates and transformed into E. coli as described previously. Plasmid DNA was prepared by the alkaline lysis method and digested with restriction endonucleases to confirm the identity of the plasmid. The plasmid DNA was also transformed into DBY1 (pL72, YElpac112GE2 87S, 131H) and replica plated to GAL/XGAL plates to determine if the plasmid recovered was responsible for the color formation in the original screen. The activation of the reporter plasmid was also quantitated, essentially as was described for the E2 mutants, except that YMM minus tryptophan, leucine, and uracil was used for growth and galactose induction. From the original colonies isolated in the screen, only colonies which retested positive after repeat isolation of the cDNA plasmid were retained.

The cDNA plasmids that specifically interacted with E2 were subjected to DNA sequence analysis using a primer initiating within the VP16 coding sequence. This provides information on the reading frame at the fusion point with the cDNA. In general using this primer we have determined about 200–300 nucleotides of DNA sequence. Provided in Table 1 below is a guide to the sequence listings for each of these clones.

Furthermore, a deposit of each of these clones as a library of pEJA plasmids (designated "pRS306-E2BP") containing the 4 different novel clones isolated in the E2 interaction trap has been made with the American Type Culture Collection (Rockville, Md.) on Oct. 19, 1994, under the terms of the Budapest Treaty. ATCC Accession number 75915 has been assigned to the deposit. With this deposit in hand, one of ordinary skill in the art can generate the subject recombinant E2-BP genes and express recombinant forms of the subject E2-binding proteins. For instance, each of the E2-binding proteins of the present invention can be amplified from ATCC deposit No:75915 by PCR using the following primers:

5'-TAC ATT AGG TCC TTT GTA GC-3'(SEQ ID NO:14)
5'-GGC GTG AAT GTA AGC GTG AC-3'(SEQ ID NO:15)

which prime amplification of the cDNA insert by hybridizing upstream of the VP-16 gene and downstream of the cDNA insert, respectively. The primer

5'G CAG ATG TTT ACC GAT GCC C-3'(SEQ ID NO:13)

which primes within the VP 16 gene and near the VP16/cDNA boundary, can also be used to isolate the clones of the ATCC deposit.

Moreover, it will be immediately evident to those skilled in the art that, in light of the guide to the 5' (and in some instances the 3' ends) to each of the clones provided in Table 1, each individual clone of the ATCC deposit can be isolated using primers based on the nucleotide sequences provided by SEQ ID Nos. 1–4, or a combination of such primers and the primers based on flanking plasmid sequences.

Isolated clones can be subcloned into expression vectors in order to produce a recombinant protein, or can be used to generate anti-sense constructs, or can be used to generate oligonucleotide probes. In an illustrative embodiment, oligonucleotide probes have been generated using the coding sequences for each of the clones of the subject ATCC deposit, and used in Southern hybridization and in situ hybridization assays to detect the pattern and abundance of expression of each of the E2-binding proteins.

Moreover, because each member of the ATCC deposit is a plasmid encoding a fusion protein identified from an interaction trap assay, the clone can be utilized directly from the deposit in a similar ITS employed as, for example, a drug screening assay, or alternatively, a mutagenesis assay for mapping E2 binding epitopes.

TABLE 1

Guide to pRS306-E2BP

| Clone | Nucleotide Sequence | Peptide Sequence | Name |
| --- | --- | --- | --- |
| 42A | SEQ ID NO: 1 | SEQ ID NO: 5 | E2-BP$^{42A}$ |
| SD2-7 | SEQ ID NO: 2 | SEQ ID NO: 6 | E2-BP$^{SD2-7}$ |
| SD-23 | SEQ ID NO: 3 | SEQ ID NO: 7 | E2-BP$^{SD-23}$ |
| SD24 | SEQ ID NO: 4 | SEQ ID NO: 8 | E2-BP$^{SD-24}$ |

The 42A clone represented an insert of about 1000 bases, encoding an open reading frame of 357 amino acid residues. Internally within the reading frame is an exact copy of a brain expressed sequence tag (EST) previously described in Adams et al. ((1993) *Nat Genet* 4:256–267, although the homology ends at the 3' end of the EST sequence and the 42A clone continues on for several hundred additional nucleotides. Northern blot analyses under high stringency conditions with the 42A sequence reveals that it hybridizes to a transcript of about 2,000 nucleotides in size that is expressed in both cultured human keratinocytes and HeLa cells.

In Vitro Association Assay

An in vitro protein binding assay was developed for characterization of the association between the E2 and E2-binding proteins. This assay is based on the binding of a protein to glutathione S-transferase (GST) E2 translational fusions which are immobilized on Sepharose CL-4B glutathione beads (Pharmacia) (Smith et al. (1988) *Gene* 67:31). Soluble protein associating with the E2 moiety can be purified with the beads.

A series of GST E2 fusions were constructed in pGEX2T (Pharmacia). In addition, a fusion of GST and the VP16 transactivation domain from the original 42A isolate was made in pGEX2T for use as a negative control. The GST fusion plasmids were transformed into E. coli BL21(DE3)

pLysS and synthesis of recombinant protein was induced by addition of 1 mM isopropyl-β-D-thiogalactopyranoside (IPTG) (Studier et al. (1990) *Meth Enzymol* 185:60–89). Fusion proteins were extracted from frozen cell pellets, bound to glutathione beads, and visualized by Coomassie staining after SDS/PAGE.

An in frame initiation codon (ATG) was fused to the 42A open reading frame (ORF), and this fusion was transferred to PSP65 for in vitro synthesis of RNA. $^{35}$S-labeled 42A protein was synthesized by translation of the in vitro transcribed RNA in rabbit reticulocyte lysate.

Binding reactions contained about 5μg of E2 fusion protein (as determined by BCA protein assay, Pierce Scientific) and 100,000 cpm of $^{35}$S-labeled 42A protein in a total volume of 250μl of NETN (20 mM tris pH 8.0, 100 mM NaCl, 1 mM EDTA, 0.5% Nonident P-40) with protease inhibitors. Reactions were incubated for 3 to 5 hr. at 4° C. with shaking, and the beads were pelleted. The pellets were washed five times with 1 ml of ice cold NETN, and an additional three times with NETN with 500 mM NaCl. After the last wash, samples were resuspended in sample buffer and resolved by SDS/PAGE using a 12% gels. Proteins were visualized by autoradiography.

Initially, an inframe translational fusion of BPV1E2 amino acids 1 to 286 was tested for ability to associate with 42A in vitro. As shown in FIG. 2, 42A copurified with GST E2-286, but not with GST alone, or a GST VP16 transactivation domain fusion (VP16 amino acids 410–490). Furthermore, 42A associated equally well with GST E2-286 (87L, 131H). These mutations, in the context of full length E2 (amino acids 1 to 410) were used in the two hybrid screen to isolate 42A.

The interaction of E2 and 42A was further characterized in vitro using a series of truncations of E2 amino acids 1 to 286 fused to GST. In addition, the deletions (with an in frame ATG added) were fused to E2 amino acids 287 to 410, and assayed in the two hybrid system (in yeast) with VP1642A and the E2 dependent LacZ reporter, pL72. These experiments, summarized in FIG. 2 show that constructs lacking E2 amino acids 1 to 52 (GST E2 53–286, E2 53–410), 1 to 113 (GST E2 113–286, E2 113–410), and 1 to 134 (GST E2 134–286, E2 134–286) are able to associate with 42A in vitro and in vivo. However, deletion of E2 amino acids 1 to 161 (GST E2 162–286, E2 162–410) abolished interaction with 42A in both assays.

Currently, only one carboxy-terminal deletion of the first 286 amino acids of E2 has been tested as a GST fusion for 42A association. Removal of E2 amino acids 216 to 286 (see FIG. 2, GST E2 113–215) does not diminish the binding of 42A. An analogous in frame deletion of E2 amino acids 218 to 284 (FIG. 2, E2 Hinge Deletion) was also found to interact with VP1642A in the two hybrid assay.

The physical association of E2 with 42A in the in vitro binding assay confirms that using the two hybrid assay, we have isolated an E2 binding protein. The similar behavior of E2 deletions in the context of E2 and as GST fusions indicates that the in vitro binding assay accurately reflects 42A-E2 interactions characterized using the two hybrid assay. Taken together, these data indicate that a domain for binding 42A lies between E2 amino acids 134 and 215. It is noteworthy that the lesions of the E2 mutant used to isolate 42A (E2 87L, 131 H) in the two hybrid assay lie outside this interval. We conclude that these mutations inactivate a domain of E2 required for transcriptional activation, but do not affect a second domain of E2 required for binding 42A. Consistent with this conclusion, there were no differences in the ability of GST E2 286 and GST E2–286 (87L, 131H) to bind 42A in vitro.

Using a coimmunoprecipation assay we have shown that the 42A ORF is able to associate with an intact (ie amino acids 1 to 410), wild type E2 molecule. For this experiment E2, E2R (amino acids 162 to 410), and 42A were synthesized in rabbit reticulocyte lysate. Full length E2 or E2R was mixed with 42A in 50 μl of NETN with protease inhibitors. After 1 hour on a rotator at 4° C. an additional 200 μl of NETN was added along with PAS (protein a sepharose beads, Pharmacia) bound to an monoclonal antibody (B202) recognizing an epitope in the DNA binding domain of E2. As expected, after the PAS beads were pelleted, washed, and resolved by SDS/PAGE (essentially as described for the GST fusion experiments above) both E2 and E2R were immunoprecipitated by the E2 specific B202 antibody. The 42A protein was also precipitated along with E2 but not E2R, and in control experiments it was shown that B202 was unable to immunoprecipitate 42A in the absence of E2. This experiment shows that the 42A ORF is able to physically interact with a wild type, full length E2 molecule.

Validation of E2 Association Binding Activity

The two hybrid system has been exploited to further validate and analyze the interaction, using both plate x-gal assays and, in limited studies, quantitative experiments (Table 2). No cooperative activation was seen with the 112-G vector (No E2) or with the 125 amino acid binding domain (data not shown). In addition to the E2 mutant used to isolate 42A (112GE2 87L, 131H), a second mutant (112GE2 15H) was found to cooperate with VP 16-42A as shown in Table 2. Interestingly, a truncated stable E2 product that does not include the amino terminal 112 residues of E2 was active with VP16-42A. However, deletion of amino acids 1 to 161 (E2-TR, which is also stable) was not activated by VP 16-42A (data not shown). In all cases transcriptional stimulation was dependent on the VP16 transactivation domain (TAD) in the 42A hybrid (compare columns 3 and 4). Interestingly, co-expression of VP 16-42A with WT E2 produced an approximate 3 fold increase in transactivation (column 3). In yeast that expressed WT E2 on a low copy CEN/ARS plasmid, the induction by pSD10 VP16-42A was 5 times E2 alone and reduced 75% when the entire 42A open reading frame (ORF) lacking the VP16 TAD was used (data not shown). This inhibiting effect was also seen with high copy WT E2 and the 42A ORF (column 4). These results provide evidence for the specificity of the interaction between 42A and E2, and imply that amino acids 113–161 of E2 are necessary for the interaction. The inhibiting effect, if confirmed, of expressing the 42A ORF (without VP16) suggests that it may represent a domain that alone interferes with E2 function.

TABLE 2

β-gal expression in *S. Cerevisiae* with E2 and 42A.

| E2 construct or vector control | SD10 VP16 control | SD10 VP16/42A | SD10 42A (no VP16) |
|---|---|---|---|
| 112G-E2 | 210 | 619 | 120 |
| 112G-E2 87L,131H | 2.8 | 12.5 | 1.2 |
| 112G-E2 15H | 1.7 | 21 | 0.4 |
| 112G-E2 113–410 | 1.6 | 16 | 1.0 |
| 112-G | 1.2 | 1.3 | 1.2 |

TABLE 2-continued

β-gal expression in S. Cerevisiae with E2 and 42A.

| E2 construct or vector control | SD10 VP16 control | SD10 VP16/42A | SD10 42A (no VP16) |
|---|---|---|---|

Column 1: E2 expression vector or control
112G = 2μ replicon with the GAL 1–10 UAS, TRP1. 112G-E2 87L, 131H (used in the screen that isolated the 42A cDNA) and 112G-E2 15H are TAD mutants expressed at wt levels in S. cerevisiae. 112G-E2 113–410 begins with amino acid 113 of BPV E2 (i.e. deletion of AA 1–113)
Column 2: Random isolate from the SD10 VP16 cDNA library used as a negative control.
Column 3: SD10 42A isolate (hybrid includes VP16 TAD)
Column 4: SD10 42A isolate with in frame deletion of the VP16 transactivation domain.

The two hybrid system used to isolate the 42A open reading frame (ORF) employed a mutation of BPV-1 E2 with a very low level of intrinsic transactivation potential. In this assay, when wild type (WT) E2 is used in place of the mutant, transcriptional activation (transactivation) of the reporter is stimulated by the VP 16-42A fusion as compared with a randomly chosen ORF fused to VP16. This finding suggested that the 42A ORF physically interacts with WT E2 bound to the E2 response elements in the promoter. The VP16 moiety presumably stimulates initiation of transcription of the reporter independently of the transactivation domain of E2. The inability of the 42A ORF or the VP16 transactivation domain to cause this effect individually (see columns 3 and 4) is consistent with this model.

Figure 3:
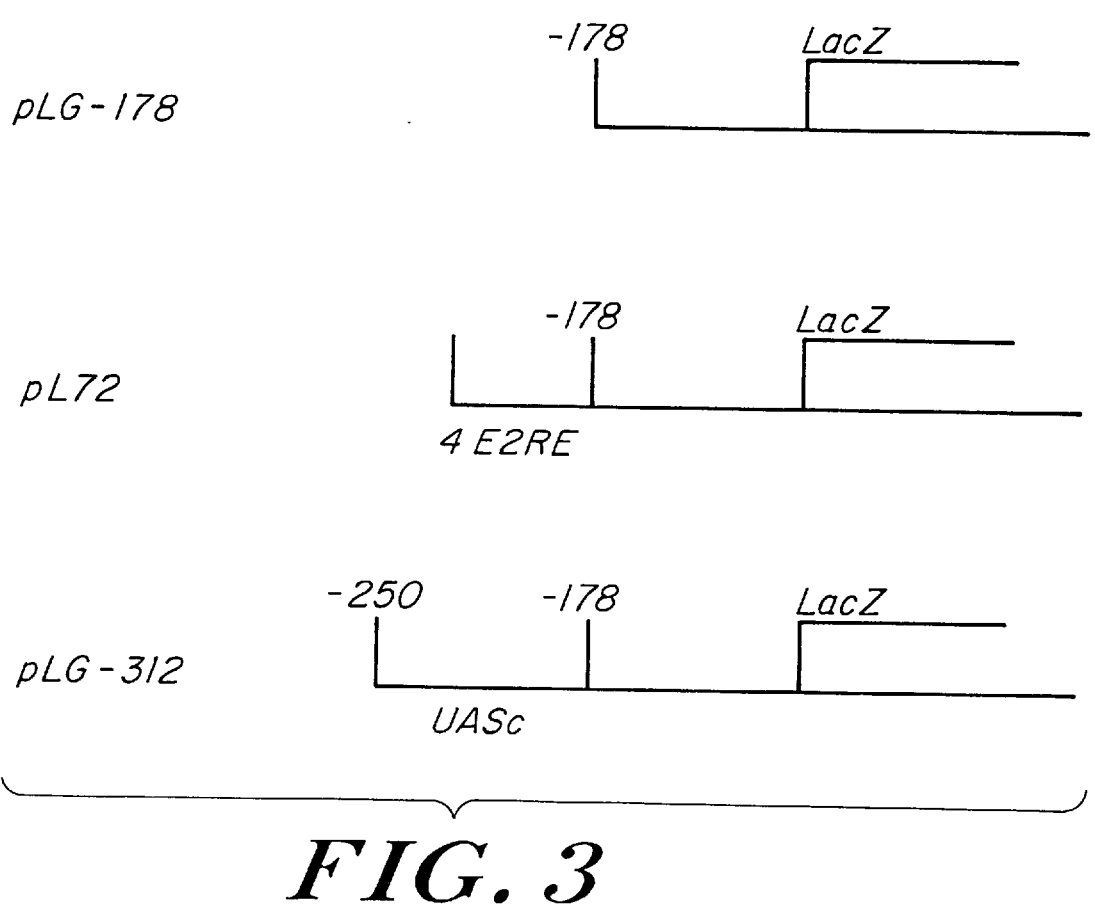
FIG. 3 is a schematic diagram of the β-galactosidase reporters pLG-178, pL72 and pLg-312.

The two hybrid system used to isolate 42A was further characterized to examine possible effects of 42A on the promoter which are independent of E2. We determined if E2RE in the promoter are required for the effect seen with WT E2 and VP1642A in the original two hybrid assay (Table 2) using pLG -178, which lacks E2 response elements (FIG. 3). Construction of the pL72 reporter originally used involved deletion of nucleotides -250 to -178 of pLG -250 (a chimeric yeast pCYC1/LacZ reporter) and insertion of 4 copies of E2 response elements (E2RE) at position -178 (FIG. 3) (Morissey et al. (1989) Supra,Guarente and Mason (1983), Supra).

As shown in Table 3, reporter pLG -178, which is otherwise identical to pL72, is not activated by WT E2 (line 1). Furthermore, VP1642A does not effect this reporter either in the presence or absence of E2 (column 2). These results indicate that the effects of VP1642A on transactivation of pL72 by various E2 constructs (Table 2) requires E2 bound to the promoter. Consistent with this observation E2 340R, a mutant defective for binding to E2RE, fails stimulate transcription of pL72 plus or minus VP1642A (data not shown).

TABLE 3

Characterization of the Promoter Specificity of 42A by Quantitative β-Galactosidase Assay

|  | VP16 | VP16 42A | VP16 SD7 | VP16 SD8 | 112GE2 WT |
|---|---|---|---|---|---|
| pLG-178 | 0 | 0 | 0 | 0 | 0 |
| pLG-178 + 112GE2 | 0 | 0 | 0 | 0 | ND |
| pLG-250 | 252 | 175 | 197 | 200 | 157 |

VP1642A could be acting in a promoter specific manner, but only when transcription is activated through an upstream DNA binding element (ie. E2RE or UASc) In this case it would be expected that VP1642A has no effect of pLG -178, but response elements for other transcriptional activators (such as HAP) could substitute for those of E2. The pLG -250 reporter lacks E2RE and contains additional native pCYC1 sequence with an UASc element (FIG. 3). Characterizing the effect of VP1642A on this reporter should indicate whether it is able to affect another transcriptional activator (yeast HAP activator) as it does E2. The transcription of pLG -312 is activated by endogenous yeast HAP (Table 3 line 3). The level activation is not increased in the presence of VP1642A or by two other V16 fusions to previously unidentified ORFS from the VP16-cDNA library. These results further confirm the VP1642A acts in an E2 rather than a promoter specific manner in the original two hybrid assay.

An additional test was performed to determine if the E2 specificity of VP1642A is a result of modulation of E2 levels. It is possible that VP1642A affects pGAL4 (promoter used to drive expression of E2 in yeast) enhancing the steady state level of E2 present by increasing the activity of pGAL4, possibly acting through an upstream response element. Increasing the protein level of WT E2 or a mutant with very low intrinsic activation potential could mimic physical interaction in the two hybrid assay, resulting in a false positive.

When the expression of WT E2 was driven with pADH, a constitutive yeast promoter unrelated to the galactose inducible GAL4 promoter, VP1642A enhanced the level of transactivation of the E2 dependent pL72 reporter by E2 (data not shown). Thus, the effect of VP1642A is not dependent of the promoter used to drive E2 expression. We consider it unlikely that VP1642A would similarly affect two unrelated yeast promoters.

Alternative Two Hybrid Assay: LexA Fusion

Further confirmation of physical interaction of the 42A ORF and E2 was sought using an alternative two hybrid assay, in which 42A is tethered to the promoter via the LexA DNA binding domain (DBD), and serves to recruit E2. The 42A ORF was translationally fused to the LexA DBD by inserting the Bam HI/Not I fragment from pVL1393G42-6 into Bam HI/Not I cleaved pEG202 (Gyuris et al. (1993) Cell 75:791–803). The LexA-42A fusion was then transferred as a MluI/SalI fragment to YEplac181GLexA202; placing the fusion under control of the galactose inducible GAL4 promoter.

The LexA-42A construct (YEplac181GLexA42A) and YEplac112G were introduced into DBY1 containing LexA/ LacZ reporter pSH18–34 (Gyuris et al., supra). When synthesis of LexA-42A was induced on GAL/XGAL plates, colonies remained white after extended incubation, suggesting the 42A fusion bound LexA operators in pSH18–34, but was unable to activate transcription of the LacZ gene (Table 4, column 1). Similar results were obtained when, in place of YEplac181GLexA42A construct, YEplac181GLexA202 (LexA DBD alone), or YEplac181GLexASD22 (fusion to a previously unidentified ORF from VP16-cDNA library) were used. As expected a fusion of the transcriptional activation domain of the yeast GAL4 gene to the LexA DBD (YEplac181GLexAGAL4) activated transcription of pSH18–34 strongly, resulting in blue color formation.

TABLE 4

Alternative Two Hybrid Assay

|  | YEplac181G LexA42A | YEplac181G LexA202 | YEplac181G LexASD22 | YEplac181G LexAGal4 |
|---|---|---|---|---|
| Yeplac112GE2 | blue[48 hr.1] | white[72 hr.] | white[72 hr.] | ND |
| Yeplac112GE2-340R[2] | blue[48 hr.] | white[72 hr.] | white[72 hr.] | ND |
| Yeplac112GE2-87L, 131H | white[72 hr.] | white[72 hr.] | white[72 hr.] | ND |
| Yeplac112G | white[72 hr.] | white[72hr.] | white[72 hr.] | blue[24 hr.] |

[1]4 colonies inoculated to YMM (minus tryptophan, leucine, uracil)GAL/XGAL plate, which were incubated an 30° C. for the times indicated. In all cases the reporter was pSH18-34.
[2]YEplac112GE2 340R is a mutant of E2 which is unable to bind E2 elements, and is defective for transactivation when assayed with the E2 dependent reporter pL72 (Prakash et al. Supra). ND, not done.

Activation of pSH18–34 was also observed when the LexA42A fusion (YEplac181GLexA42A) and either wild type E2 (YEplac112GE2) or E2 340R (YEplac112GE2 340R, defective for binding E2RE were coexpressed. This activation did not occur when YEplac181GLexA202 or YEplac181GLexASD22 were used in place of the LexA42A fusion. These results show that the 42A ORF, when localized to the promoter of pSH18–34 by the LexA DBD is able to recruit E2, which activates transcription. The transactivation defective mutant of E2 (YEplac112GE2, 87L, 131H) used to isolate 42A in the original two hybrid screen was unable to activate the LexA reporter in the presence of LexA42A. This mutant E2 protein presumably associates with the 42A moiety of the LEexA42A fusion, but is unable to activate transcription due to the presence of mutations in its transactivation domain.

Interaction ofDeletions of42A with BPV-1 E2*in S. Cervisiae*

Figure 4:
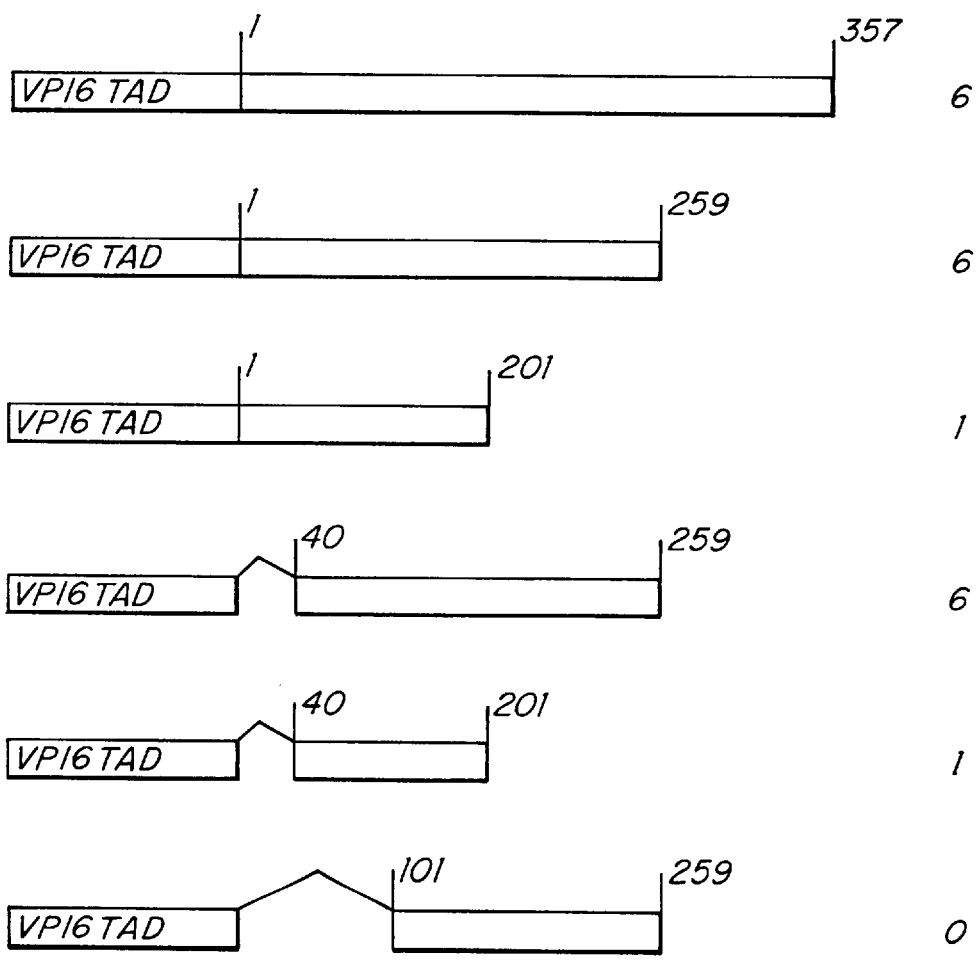
FIG. 4 is a schematic diagram illustrating the interaction of 42A deletions with BPV-1 E2 in *S. cervisiae*.

Truncations of the 42A ORF were translationally fused to the VP16 transactivation domain (TAD) in the SD10 vector. The constructs were transformed in DBY1 along with YEplac112GE2 87L, 131H and the β-galactosidase reporter pL72, described previously in this application. Blue color formation was scored on a scale of 0 (white) to 6 (intense blue) after colonies were transferred to GAL/XGAL medium. In this assay the minimal portion of the 42A ORF required for full activity was determined to lie between amino acid residues 40 to 259 (FIG. 4).

E2. 42a Transcriptional Activation Data in Mammalian Cells

Figure 5:
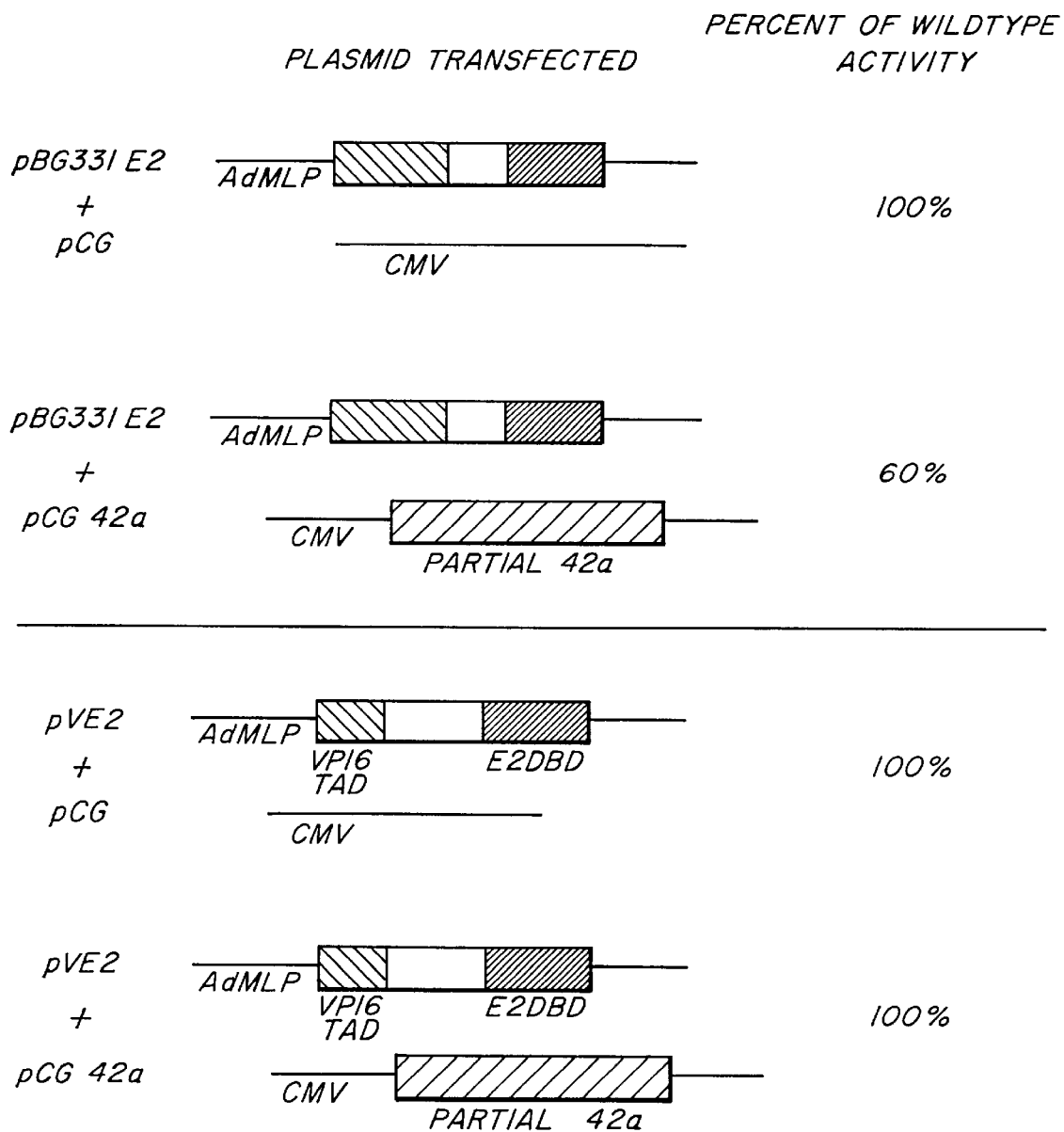
FIG. 5 is a schematic diagram illustrating E2, 42*a* transcriptional activation data in *S. cervisiae*.

This experiment was performed using a transient expression assay in COS-7 cells essentially as described for characterization of E2 mutants in mammalian cells. Expression of the 42A ORF (pCG42A, 42A ORF driven by pCMV) inhibits activation by wild type E2 (pBG331E20) by 40% (FIG. 5). This effect required expression of the 42A ORF, since cotransfection of pCG (pCMV 42A ORF deleted) with pBG331E2 did not significantly reduce transcriptional activation by E2. The presence of the 42A ORF did not reduce activation in this assay by a hybrid VP16E2 protein (VP16E2-125), which lacked the region of the E2 protein required for the interaction with 42A. This hybrid protein consists of the VP16 transcriptional activation domain fused to the C-terminal 125 amino acids of E2, which comprises the E2 DNA binding domain. As discussed previously, the region of E2 required for interaction with 42A lies between amino acids 134 and 162, which are absent in the VP16E2-125 protein. One explanation for these results is that overexpression of the 42A ORF saturates the 42A association domain on E2 molecules, preventing association of E2 with the endogenous 42A protein which is required for transcriptional activation by E2 in mammalian cells. This assumption is not unreasonable, because the 42A ORF isolated in the two hybrid screen is only a portion of a larger molecule.

42A Antibody

Antisera specific for 42A was generated in a rabbit using recombinant 42A protein made in *Escherichia coli*. A bacterial expression construct (pET8c42/10) was made by transferring the 42A ORF to pET8c, creating an amino terminal translational fusion to the first 10 amino acids of the bacteriophage T7 gene 10 present in this vector.(Studier et al. (1990) *Meth. Enzymol.* 185:60–89) The gene 10–42A fusion protein (10/42A) could be detected in extracts of *Escherichia coli* BL21 pLysS, pET8c42/10 resolved using SDSPAGE by Coomasie blue staining one hour after induction of synthesis with isopropyl-β-Dthiogalactopyranoside (IPTG). (Studier at al. (1990) *Meth. Enzymol.* 185:60–89) In Fractionation experiments most 10/42. A protein was present in an insoluble form in cell pellets, even when induction was carried out at 30° C. This protein could be solubilized by urea at concentrations of 4 molar or greater.

The inability to extract 10/42A. from bacteria with out using urea at concentrations of greater than 4 molar was the basis for the first step in the purification scheme used. *Escherichia coli* BL21 pLysS, pET42/10 were grown at 37° C. until the $A_{600}$ was between 0.5 to 0.6, at which time IPTG was added to 1 mM. Two hours after IPTG induction the culture was chilled to 4° C., and cells were pelleted by centrifugation at 4500×G for 10 min. at 4° C. The cell pellet was resuspended in ice cold phosphate buffered saline, and the cells were pelleted as previously.

Cell pellets from 500 ml of culture were resuspended in 20 ml of NETN (20 mM tris pH 8.0, 100 mM NaCl, lmM EDTA, 0.5% Nonidet P-40) with protease inhibitors (Phenylmethylsulfonylfluoride, leupeptin, pepstatin), and sonicated for 10 sec. at a setting of 7. After sonication, triton X-100 was added to 1%, and the extract was centrifuged for 30 min. at 12,000×G for 30 min at 4° C. After centrifugation the pellet was suspended in the same volume of NETN with protease inhibitors and centrifuged as before, except that the time was reduced to 10 minutes.

The pellet was extracted twice with 20 ml. of 1.5% n-octylglucosid, lmM EDTA, 150 mM NaCl, 0.25M $KPO_4$, pH 8.0. After each extraction the pellet was recovered by centrifugation as before for 15 min. The 10/42A in the pellet was then solubilized in 8M urea, and subjected to ion exchange chromatography using SP Sepharose Fast Flow (Pharmacia), which was monitored by Coomasie blue staining of fractions resolved by SDS/.PAGE. The 10/42A 8M urea fraction was adjusted to 50 mM Hepes pH 7.1, and loaded on a column equilibrated with 8M urea, 50 mM Hepes pH 7.1. After the column was washed with loading buffer, protein on the column was eluted by increasing the NaCl concentration in 100 mM steps. Most of 10/42A was eluted from the column at the 200 mM NaCl step, and this fraction was used for immunization of a rabbit.

For the initial injection and first boost two weeks afterward, approximately 2 mg of the 10/42A 200 mM eluate was emulsified with Hunters Titer Max (Sigma) after the urea concentration was reduced to 1M. A third injection was done after a additional two week interval using eluate emulsified with Freunds incomplete adjuvant (Sigma) without reducing the urea concentration.

The presence of antibodies specific for the 10/42A protein was monitored by probing western blots of IPTG induced Escherichia coli BL21 pLysS, pET8c42/10 with sera from the immunized rabbit. Detection of specific interaction was done as described previously with an alkaline phosphatase assay. Two weeks after the third injection serum from the immunized rabbit was found to specifically detect 10/42A at dilutions of up to 1:5000 in this assay.

The presence of 42A-specific antibodies in this serum was further demonstrated using an immunoprecipitation assay. This serum was found to immunoprecipitate $^{35}$S-labeled 42A protein synthesized in rabbit reticulocyte lysate, but not an unrelated protein (TATA binding protein, from *Saccharomyces cerevisiae*) also synthesized in reticulocute lysate.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for evaluating the ability of a test compound to interact with an E2-binding protein (E2-BP), or fragment thereof which binds to a papillomavirus E2 protein said E2-BP selected from the group consisting of E2-BP$^{42A}$ (SEQ ID NO:5), E2-BP$^{SD2-7}$ (SEQ ID:6), E2-BP$^{SD-23}$ (SEQ ID NO:7), and E2-BP$^{SD-24}$ (SEQ ID NO:8) comprising: contacting said E2-BP with said test compound and determining whether said test compound interacts with said E2-BP.

2. The method of claim 1, wherein said E2-BP is E2-BP$^{42A}$ (SEQ ID NO:5).

3. The method of claim 1, wherein said E2-BP is E2-BP$^{SD2-7}$ (SEQ ID NO:6).

4. The method of claim 1, wherein said E2-BP is E2-BP$^{SD-23}$ (SEQ ID NO:7).

5. The method of claim 1, wherein said E2-BP is E2-BP$^{SD-24}$ (SEQ ID NO:8).

6. The method of claim 1, wherein the interaction comprises binding.

7. The method of claim 1, wherein said E2-BP and said test compound are contacted in a cell-free system.

8. The method of claim 7, wherein the cell free system is selected from the group consisting of a cell lysate and a reconstituted protein mixture.

9. The method of claim 1 wherein said E2-BP is a fusion protein.

10. The method of claim 9 wherein said fusion protein is a Glutathione-S-transferase fusion protein.

11. The method of claim 1, wherein said E2-BP is a purified preparation.

12. The method of claim 1, wherein said E2-BP is immobilized.

13. The method of claim 1, wherein said E2 protein is a human papillomavirus (HPV) E2 protein.

14. The method of claim 13, wherein said HPV is a high risk HPV.

15. The method of claim 14, wherein said HPV selected from a group consisting of HPV-16, HPV-18, HPV-31 and HPV-33.

16. The method of claim 1 wherein said E2 protein is bovine papilloimavirus (BPV) E2 protein.

17. A method for evaluating the ability a test compound to modulale an interaction of an E2-binding protein (E2-BP) to a papillomavirus E2 protein, comprising:

i) combining an E2 protein or fragment thereof which binds to lE2-BP, an E2-BP or fragmnent thereof which binds to said E2 protein, and a test compound, said E2-BP selected from the group consisting of E2-BP$^{42A}$ (SEQ NO:5), E2-BP$^{SD2-7}$ (SEQ ID NO:6), E2-BP$^{SD-23}$ (SEQ ID NO:7), and E2-BP$^{SD-24}$ (SEQ NO:8), under conditions wherein in the absence of said test compound said E2 protein and E2-BP are able to interact; and ii) detecting the interaction between said E2-BP and E2 protein in the absence and the presence of said test compound, wherein a decrease in the level of interaction in the presence of said test compound is indicative of a compound that inhibits the interaction of a papillomavirus E2 protein with an E2-BP.

18. The method of claim 17, wherein said E2-BP is E2-BP$^{42A}$ (SEQ ID NO:5).

19. The method of claim 17, wherein said E2-BP is E2-BP$^{SD2-7}$ (SEQ ID NO:6).

20. The method of claim 17, wherein said E2-BP is E2-BP$^{SD-23}$ (SEQ ID NO:7).

21. The method of claim 17, wherein said E2-BP is E2-BP$^{SD-24}$ (SEQ ID NO:8).

22. The method of claim 17, wherein said interaction comprises binding.

23. The method of claim 17, wherein said E2-BP, E2 protein and test compound are combined in a cell-free system.

24. The method of claim 23, wherein the cell-free system is selected from the group consisting of a cell lysate and a reconstituted protein mixture.

25. The method of claim 17, wherein said E2-BP is a fusion protein.

26. The method of claim 25, wherein said ftusion protein is a Glutathlionc-S-transferase fusion protein.

27. The method of claim 17, wherein said E2-BP is a purified preparation.

28. The method of claim 17, wherein said E2-BP is immobilized.

29. The method of claim 17, wherein at least one of said E2 and E2-BP comprises a detectable label for detecting the interaction between said E2 and E2-BP.

30. The method of claim 17, wherein said E2-BP and E2 protein are simultaneously expressed in a cell and said cell is contacted with a test compound.

31. The method of claim 17, wherein said E2-BP and E2 protein conmprise a two-hybrid assay system.

32. The method of claim 31, wherein said two-hybrid assay system comprise a reporter construct which includes a transcriptional control element responsive to one of an E2 protein, a Gal4 protein, or a LexA protein, a first fusion protein comnprising said E2 protein, and a second fusion protein comprising said E2-BP, wherein one of said first fusion protein or second fusion protein includes a portion which binds to said transcriptional control element.

33. The method of claim 17, wherein said E2 protein is a human papillomavirus (HPV) E2 protein.

34. The method of claim 33, wherein said HPV is a high risk HPV.

35. The method of claim 34, wherein said HPV is selected from a group consisting of HPV-16, HPV-18, HPV-31 and HPV-33.

36. The method of claim 17, wherein said E2protein is bovine papillomavirus (BPV) E2protein.

37. A two phase method for evaluating the ability of a test compound disrupt the binding of an E2-binding protein (E2-BP) with a papillormavirus E2 protein comprising:

(i) combining in vitro an E2 protein or fragmnent thereof which binds to an E2-BP, an E2-BP or fragrment thereof which binds to said E2 protein, and a test compound, said E2-BP selected from the group consisting of E2-BP$^{42A}$ (SEQ ID NO:5), E2-BP$^{SD2-7}$ (SEQ ID NO:6), E2-BP$^{SD-23}$ (SEQ ID NO:7), and E2-BP$^{SD-24}$ (SEQ ID NO:8) under conditions wherein in the absence of test compound said E2 protein and the E2-BP are able to interact;

(ii) detecting an interaction between said E2 protein and said E2-BP in the presence and absence of said test compound, wherein a change in the interaction relative to the interaction detected in the absence of said test compound is indicative of a modulation of the interaction between said E2 protein and said E2-BP;

(iii) determining if said test compound changes the interaction between said E2 protein and said E2-BP;

(iv) administering to a cell or animal a test compound which changes the interaction between said E2 protein and said E2-BP; and (v) evaluating the in vivo effect of the test compound.

38. The method of claim 37, wherein the effect of said test compound is detected by at least one of changes in cell growth, or expression of a papillomavirus (PV) gene or a reporter gene.

39. The method of claim 37, wherein said E2-BP is E2-BP$^{42A}$ (SEQ ID N0: 5).

40. The method of claim 37, wherein said E2-BP is E2-BP$^{SD2-7}$ (SEQ ID NO:6).

41. The method of claim 37, wherein said E2-BP is E2-BP$^{SD-23}$ (SEQ ID NO:7).

42. The method of claim 37, wherein said E2-BP is E2-BP$^{SD-24}$ (SEQ ID NO:8).

* * * * *